US00RE49583E

(19) United States
(12) Reissued Patent
Berkhout et al.

(10) Patent Number: US RE49,583 E
(45) Date of Reissued Patent: Jul. 18, 2023

(54) INDUCIBLE EXPRESSION SYSTEMS

(71) Applicant: TET Systems GmbH & Co. KG, Heidelberg (DE)

(72) Inventors: Benjamin Berkhout, Naarden (NL); Atze T. Das, Amsterdam (NL)

(73) Assignee: TET Systems GmbH & Co. KG, Heidelberg (DE)

(21) Appl. No.: 17/166,090

(22) Filed: Feb. 3, 2021

Related U.S. Patent Documents

Reissue of:
(64) Patent No.: 8,383,364
Issued: Feb. 26, 2013
Appl. No.: 12/085,107
Filed: Oct. 21, 2009

(30) Foreign Application Priority Data

Nov. 17, 2005 (EP) ..... 05077623

(51) Int. Cl.
*C12N 7/00* (2006.01)
*A61K 39/12* (2006.01)
*A61K 39/21* (2006.01)
*C12N 15/63* (2006.01)
*A61K 39/00* (2006.01)

(52) U.S. Cl.
CPC ..... *C12N 7/00* (2013.01); *A61K 39/12* (2013.01); *A61K 39/21* (2013.01); *C12N 15/635* (2013.01); *A61K 2039/5254* (2013.01); *C12N 2740/16034* (2013.01); *C12N 2740/16061* (2013.01); *C12N 2830/003* (2013.01)

(58) Field of Classification Search
CPC ..... A61P 37/04; C12N 7/00; A61K 39/12
See application file for complete search history.

(56) References Cited

U.S. PATENT DOCUMENTS

| | | | |
|---|---|---|---|
| 4,997,764 | A | 3/1991 | Dalla Favera |
| 5,684,147 | A | 11/1997 | Agrawal et al. |
| 5,866,757 | A | 2/1999 | Reisner et al. |
| 6,001,558 | A | 12/1999 | Backus et al. |
| 7,541,446 | B2 | 6/2009 | Hillen et al. |
| 2003/0152559 | A1 | 8/2003 | Yang et al. |
| 2003/0158131 | A1 | 8/2003 | Aldovini |
| 2005/0009180 | A1 | 1/2005 | Yang et al. |
| 2005/0037335 | A1 | 2/2005 | Hillen |

FOREIGN PATENT DOCUMENTS

| | | | |
|---|---|---|---|
| EP | 1 627 563 | | 2/2006 |
| GB | 2 398 783 | | 9/2004 |
| WO | WO 89/08146 | | 9/1989 |
| WO | WO 94/08004 | | 4/1994 |
| WO | WO 95/06409 | | 3/1995 |
| WO | 96/01313 | A1 | 1/1996 |
| WO | WO 96/01313 | A | 1/1996 |
| WO | 01/20013 | A2 | 3/2001 |
| WO | WO 01/20013 | A | 3/2001 |
| WO | WO 03/050262 | | 6/2003 |
| WO | WO 03/052083 | | 6/2003 |
| WO | WO 03/070193 | | 8/2003 |
| WO | WO 03/079757 | | 10/2003 |
| WO | 2005/052164 | A1 | 6/2005 |
| WO | WO 2005/052164 | A | 6/2005 |
| WO | 2005093075 | A1 | 10/2005 |
| WO | WO 2005/102383 | | 11/2005 |
| WO | 2005/123923 | A2 | 12/2005 |
| WO | WO 2005/123923 | A | 12/2005 |
| WO | 2006084695 | A2 | 8/2006 |
| WO | WO 2006/132524 | | 12/2006 |
| WO | WO 2007/058527 | A2 | 5/2007 |

OTHER PUBLICATIONS

Urlinger et al., "Exploring the sequence space for tetracycline-dependent transcriptional activators: Novel mutations yield expanded range and sensitivity," Proc Natl Acad Sci U S A. Jul. 5, 2000;97(14):7963-8.

Das et al., "Viral evolution as a tool to improve the tetracycline-regulated gene expression system," J Biol Chem. Apr. 30, 2004;279(18):18776-82. Epub Feb. 2, 2004.

Zhou et al., "Optimization of the Tet-On system for regulated gene expression through viral evolution," Gene Ther. Oct. 2006;13(19):1382-90. Epub May 25, 2006.

Berens et al., "The role of the N terminus in Tet repressor for tet operator binding determined by a mutational analysis," J Biol Chem. Jan. 25, 1992;267(3):1945-52.

Hecht et al., "Noninducible Tet repressor mutations map from the operator binding motif to the C terminus," J Bacteriol. Feb. 1993;175(4):1206-10.

Müller et al., "Characterization of non-inducible Tet repressor mutants suggests conformational changes necessary for induction," Nat Struct Biol. Aug. 1995;2(8):693-703.

Bertram et al., "Phenotypes of combined tet repressor mutants for effector and operator recognition and allostery," J Mol Microbiol Biotechnol. 2004;8(2):104-10.

Scholz et al., "Activity reversal of Tet repressor caused by single amino acid exchanges," Mol Microbiol. Aug. 2004;53(3):777-89.

The International Search Report and Written Opinion, dated Jul. 27, 2007, in PCT Appl. No. PCT/NL2006/000575.

Krueger C et al: "Single-chain Tet transregulators" Nucleic Acids Research, Oxford University Press, Surrey, GB, vol. 31, No. 12, Jun. 15, 2003 (Jun. 15, 2003), pp. 3050-3056, XP002317267.

Knott A et al: "Tetracycline-Dependent Gene Regulation: Combinations of Transregulators Yield of a Variety of Expression Windows" Biotechniques, Informa Life Sciences Publishing, Westborough, MA, US, vol. 32, No. 4, 2002, pp. 796-806, XP008044173.

(Continued)

*Primary Examiner* — Padmashri Ponnaluri
*Assistant Examiner* — Jean C Witz

(57) ABSTRACT

Provided is an rtTA and single chain rtTA variants and uses thereof for inducible expression of a nucleic acid of interest. Nucleic acid molecules comprising an improved rtTA and/or sc rtTA sequence according to the invention are also provided, as well as vectors, replicons and cells comprising such nucleic acid molecules.

83 Claims, 25 Drawing Sheets

Specification includes a Sequence Listing.

(56) References Cited

OTHER PUBLICATIONS

Zhou Xue et al: "The genetic stability of a conditional live HIV-1 variant can be improved by mutations in the Tet-On regulatory system that restrain evolution." The Journal of Biological Chemistry Jun. 23, 2006, vol. 281, No. 25, Jun. 23, 2006 (Jun. 23, 2006), pp. 17084-17091.
Zhou Xue et al: "Modification of the Tet-On regulatory system prevents the conditional-live HIV-1 variant from losing doxycycline-control." Retrovirology 2006, vol. 3, 2006, p. 82, XP002434298.
Zhou Xue et al: "Improved single-chain transactivators of the Tet-On gene expression system." BMC Biotechnology 2007, vol. 7, 2007, p. 6, XP002434300.
Gossen M et al: "Transcriptional Activation by Tetracyclines in Mammalian Cells" Science, American Association for the Advancement of Science US, vol. 268, Jun. 23, 1995 (Jun. 23, 1995), pp. 1766-1769.
Atze Das et al: "A Conditionally Replicating Virus as a Novel Approach Toward an HIV Vaccine" Methods in Enzymology, San Diego, Academic Press, US, vol. vol. 388, 2004, pp. 359-379, XP008061959.
Salucci V et al: "Tight control of gene expression by a helper-dependent adenovirus vector carying the rtTA2S-M2 tetracycline transactivator and repressor system" Gene Therapy, MacMillan Press Ltd., Basingstoke, GB, vol. 9, 2002, pp. 1415-1421, XP002320614.
Koff, Vaccine vol. 30 (2012) pp. 4310-4315.*
VanRegenmortel, Arch. Virol. vol. 157 (2012) pp. 1-20.*
Gossen et al., Transcriptional Activation by Tetracyclines in Mammalian Cells, Science, Jun. 23, 1995, pp. 1766-1769, vol. 268, American Association for the Advancement of Science, US.
Krueger et al., Single-chain Tet transregulators, Nucleic Acids Research, Jun. 15, 2003, pp. 3050-3056, vol. 31, No. 12, Oxford University Press, Surrey, GB.
Urlinger et al., Exploring the sequence space for tetracycline-dependent transcriptional activators: novel mutations yield expanded range and sensitivity, Proceedings of the National Academy of Sciences of USA, pp. 7963-7968, Jun. 5, 2000, vol. 97, No. 14, National Academy of Science, Washington, DC, US.
Das Atze et al., Viral evolution as a tool to improve the tetracycline-regulated gene expression system, The Journal of Biological Chemistry, Apr. 30, 2004, pp. 18776-18782, vol. 279, No. 18.
Das Atze et al., A Conditionally Replicating Virus as a Novel Approach Toward an HIV Vaccine, Methods in Enzymology, 2004, pp. 359-379, vol. 388, Academic Press, San Diego, US.
Salucci et al., Tight control of gene expression by a helper-dependent adenovirus vector carrying the rtTA2S-M2 tetracycline transactivator and repressor system, Gene Therapy, 2002, pp. 1415-1421, vol. 9, Macmillan Press Ltd., Basingstoke, GB.
Knott et al., Tetracycline-dependent Gene Regulation: Combinations of Transregulators Yield of a Variety of Expression Windows, Biotechniques, 2002, pp. 796-806, vol. 32, No. 4, Informs Life Sciences Publishing, Westborough, MA, US.
Zhou et al., Optimization of the Tet-On system for regulated gene expression through viral evolution, Gene Therapy, Oct. 2006, pp. 1382-1390, vol. 13, No. 19.
PCT International Search Report, PCT/NL2006/000575, dated Jul. 27, 2007.
Alajez, et al., Therapeutic potential of a tumor-specific, MHC-unrestricted T-cell receptor expressed on effector cells of the innate and the adaptive immune system through bone marrow transduction and immune reconstitution; Blood, Jun. 15, 2005, vol. 105, No. 12; pp. 4583-4589.
Chlewicki, et al., High-affinity, Peptide-specific T Cell Receptors can be Generated by Mutations in CDR1, CDR2 or CDR3; J. Mol. Biol.; 2005; 346, 223-239.
Clay, et al., Efficient Transfer of a Tumor Antigen-Reactive TCR to Human Peripheral Blood Lymphocytes Confers Anti-Tumor Reactivity, Journal of Immunology, 1999, pp. 507-513, vol. 163, The Williams and Wilkins Co. Baltimore, MD, US.
Clay,e t al. Potential Use of T Cell Receptor Genese to Modify Hematopoietic Stem Cells for the Gene Therapy of Cancer, Pathology Oncology Research, 1999, pp. 3-15, vol. 5, No. 1, Budapest, Hungary.
Gimeno, et al. Monitoring the effect of gene silencing by RNA interference in human DC34 <+> cells injected into newborn RAG2 <–/–> |gamma|c <–/–> mice: Functional inactivation of p53 in developing T cells, Blood Dec. 15, 2004 United States, vol. 104 No. 13, pp. 3886-3893, XP002317351, ISSN: 0006-4971, the whole document.
Goldman, et al., Enhanced human cell engraftment in mice deficient in RAG2 and the common cytokine receptor gamma chain, British Journal of Haematology, Oxford, GB, vol. 103, No. 2, Nov. 1998, pp. 335-342, XP002249529; ISSN: 0007-1048, the whole document.
Kang, et al. Long-term expression of a T-cell receptor beta-chain gene in mice reconstituted with retrovirus-infected hematopoietic stem cells, Proc. Natl. Acad. Sci., Dec. 1990, pp. 9803-9807, vol. 87, National Academy of Science, Washington, DC, US.
Knodel, et al., Abstract, Blimp-1 over-expression abrogates IL-4- and CD40-mediated suppression of terminal B cell differentiation but arrests isotype switching, European Journal of Immunology, 2001, pp. 1972-1980, vol. 31, No. 7.
Kobayashi, et al., Abstract, Prevention of acute liver failure in rats with reversibly immortalized human hepatocytes; Science (Washington, DC). vol. 287, No. 5456, Feb. 18, 2000, pp. 1258-1262, XP002159501, ISSN: 0036-8075. the whole document.
Kyba, et al. Enhanced hcmatopietic differentiation of embryonic stem cells conditionally expressing Stat5; PNAS, 2003, vol. 100, pp. 1-12.
Mathas, et al., Abstract, Intrinsic inhibition of transcription factor E2A by HLH proteins ABF-1 and Id2 mediates reprogramming of neplastic B cells in Hodgkin lymphoma, Nature Immunology, Feb. 2006, pp. 207-215, vol. 7, No. 2.
Menta, et al.. IL-21 induces the apoptosis of resting and activated primary B cells, Journal of Immunology. Apr. 15, 2003, pp. 4111-4118, vol. 170, No. 8, The Williams and Wilkins Co., Baltimore, US.
Mulloy, et al. Maintaining the self-renewal and differentiation potential of human CD34+ hematopoietic cells using a single genetic element, Blood, vol. 102, No. 13, Dec. 15, 2003, pp. 4369-4376, XP002317905, ISSN: 0006-4971, the whole document.
OZAK1, et al., Regulation of B cell differentiation and plasma cell generation by IL-21, a novel inducer of Blimp-1 and Bcl-6, Journal of Immunology, Nov. 1, 2004, pp. 5361-5371, vol. 173, No. 9.
PCT International Search Report, PCT.NL2006/00625, dated Apr. 10, 2007.
PCT International Search Report, PCT/NL2005/000581, dated Jul. 4, 2006.
PCT International Search Report, PCT/NL2005/000739, dated Nov. 29, 2006.
PCT International Search Report, PCT/NL2005/000848, dated Jul. 10, 2006.
PCT International Search Report, PCT/NL2006/000277, dated Sep. 1, 2006.
Petrie, et al., T Cell Receptor Gene Recombination Patterns, and Mechanisms: Cell Death, Rescue, and T Cell Production, J Exp Med 1995; 182: 121-7.
Schuringa, et al., Constitutive activation of STAT5A promotes human hematopoietic stem cell self-renewal and erythroid differentiation, Journal of Experimental Medicine, vol. 200, No. 5, Sep. 6, 2004, pp. 623-635, XP002317907, ISSN: 0022-1007.
Schuringa, et al.; Enforced Activation of STAT5A Facilitates the Generation of Embryonic Stem-Derived Hematopoietic Stem Cells That Contrinbute to Hematopoiesis In Vivo; Stem Cells 2004; 22:1191-1204.
Schvarts, et al., A senescence rescue screen identifies BCL6 as an inhibitor of anti-proliferative p19ARF-p53 signaling, Genes and Development, Mar. 15, 2002, pp. 681-686, vol. 16, No. 6.
Shaffer, et al.. Blimp-1 orchestrates plasma cell differentiation by extinguishing the mature B cell gene expression program, Immunity, Jul. 2002, pp. 51-62, vol. 17, No. 1.

(56) References Cited

OTHER PUBLICATIONS

Shapiro-Shelef, et al., Blimp-1 is required for maintenance of long-lived plasma cells in the bone marrow, The Journal of Experimental Medicine, Dec. 5, 2005, pp. 1471-1476, vol. 202, No. 11.
Shen Chun-Pyn, et al., B-cell-specific DNA binding by an E47 homodimer, Molecular and Cellular Biology, 1995, pp. 4518-4524, vol. 15, No. 8.
Stier, et al.. Notch1 activation increases hematopoietic stem cell self-renewal in vivo and favors lymphoid over myeloid lineage out-come, Blood, vol. 99, No. 7, Apr. 1, 2002, pp. 2369-2378, XP002317904, ISSN: 006-4971, p. 2375, left-hand column.
Traggiai, et al., Abstract; An efficient method to make human monoclonal antibodies from memory B cells: potent neutralization of SARS conoranavirus. Nature Medicine, Aug. 2004, pp. 871-875, vol. 10, No. 8.
Traggiai, et al., Abstract; Development of a human adaptive immune system in cord blood cell-transplanted mice; Science (Washington, DC) vol. 304, No. 5667, Apr. 2, 2004, pp. 104-107, XP002356076, ISSN: 0036-8075, the whole document.
Vickers, et al., Efficient reduction of target RNAs by small interfering RNA and RNase H-dependent antisense agents, 2003, The Journal of Biological Chemistry, vol. 278, pp. 7108-7118.
Weijer, et al., Intrathymic and extrathymic development of human plasmacytoid dendritic cell precursors in vivo: Blood, 2002; 99; 2752-2759.
Yamochi, et al. Adenovirus-mediated high expression of BCL-6 CV-1 cells induces apoptotic cell death accompanied by down-regulation of BCL-2 and BCL-XL, Oncogene, Jan. 14, 1999, pp. 487-494, vol. 18, No. 2.
Yang, et al. Generation of Functional antigen-specific T Cells in defined genetic backgrounds by retrovirus-mediated expression of TCR cDNAs in hematopoietic precursor cells, Proceedings of the National Academy of Sciences of USA, Apr. 30, 2002, pp. 6204-6209, vol. 99, No. 9, National Academy of Science, Washington, DC, US.
Yang, et al., Long-term in vivo provision of antigen-specific T cell immunity by programming hematopoietic stem cells, Proceedings of the National Academy of Sciences of USA, Mar. 22, 2005, pp. 4518-4523, vol. 102, National Academy of Science, Washington, DC, US.
Office Action for US. Appl. No. 10/097,542 dated Feb. 9, 2009.
Office Action for U.S. Appl. No. 11/665,510 dated Mar. 11, 2009.
Markusic et al., Comparison of single regulated lentiviral vectors with rtTA expression driven by an autoregulatory loop or a constitutive promoter, Nucleic Acids Research, 2005, pp. e63 (8 pages) (listed in the Notice of Reasons for Rejection for copending Japanese application (JP 2008-541096).
Notice of Reasons for Rejection for copending Japanese application (JP 2008-541096), Jul. 17, 2012.

* cited by examiner

D

| Culture | Day | Mutation observed in rtTA |
|---|---|---|
| B3 | 50 | E37K |
| B4 | 48 | G19E |
| B5 | 50 | E37K |
| B6 | 46 | E37K R179Q |
| C1 | 48 | E37K |
| C5 | 50 | E37K |
| C6 | 50 | G19E E156K |
| D1 | 48 | E37K |

A

| rtTA | | basal activity | max activity | fold sensitivity | dox(ng/ml) |
|---|---|---|---|---|---|
| wt | | 0 | 100 | 1 | 1000 |
| F86Y | | 0.1 | 253 | 3.2 | 314.3 |
| F86Y A209T | | 0 | 250 | 3.2 | 308.2 |

B

| | | | | | |
|---|---|---|---|---|---|
| F67S | + F86Y A209T | 0 | 482 | 16.7 | 59.8 |
| G138D | + F86Y A209T | 0 | 429 | 6.8 | 147.5 |
| E157K | + F86Y A209T | 0 | 414 | 4.4 | 228.5 |
| R171K | + F86Y A209T | 0 | 421 | 4.4 | 225.9 |
| V9I G138D | + F86Y A209T | 0 | 621 | 18.2 | 54.9 |
| V9I E157K | + F86Y A209T | 0 | 560 | 14.9 | 67.3 |
| V9I R171K | + F86Y A209T | 0 | 624 | 14.9 | 67.3 |
| F177L | + F86Y A209T | 0 | 358 | 4 | 249 |
| F67S F177L | + F86Y A209T | 0 | 485 | 17.5 | 57.2 |
| C195S | + F86Y A209T | 0 | 242 | 3.2 | 314.6 |
| G138S | + F86Y A209T | 0 | 39 | 4.9 | 206.1 |
| C68R | + F86Y A209T | 0 | 379 | 5.2 | 193 |
| V9I F67S | + F86Y A209T | 0.3 | 646 | 44.6 | 22.4 |
| F67S G138D | + F86Y A209T | 0 | 644 | 28 | 35.7 |
| F67S E157K | + F86Y A209T | 0 | 615 | 26.1 | 38.4 |
| F67S R171K | + F86Y A209T | 0 | 663 | 22.7 | 44 |
| V9I F67S G138D | + F86Y A209T | 0.7 | 715 | 113.9 | 8.8 |
| V9I F67S E157K | + F86Y A209T | 0.3 | 711 | 102.8 | 9.7 |
| V9I F67S R171K | + F86Y A209T | 0.1 | 730 | 107 | 9.3 |
| V9I G138D E157K | + F86Y A209T | 0.5 | 471 | 26 | 38.5 |
| V9I G138D R171K | + F86Y A209T | 0.2 | 582 | 30 | 33.4 |
| S12G F67S | + F86Y A209T | 0 | 641 | 45.5 | 22 |
| G19M F67S | + F86Y A209T | 0 | 758 | 56.2 | 17.8 |
| E37Q F67S | + F86Y A209T | 0.3 | 647 | 112.4 | 8.9 |
| C68R G138D | + F86Y A209T | 0.3 | 626 | 23.6 | 42.3 |
| G19M G138D | + F86Y A209T | 0.4 | 744 | 34.2 | 29.2 |
| E37Q G138D | + F86Y A209T | 0.7 | 635 | 34.2 | 29.2 |
| V9I C68R G138D | + F86Y A209T | 0.5 | 525 | 106.4 | 9.4 |
| V9I G19M G138D | + F86Y A209T | 1.1 | 751 | 128.2 | 7.8 |
| V9I E37Q G138D | + F86Y A209T | 2.7 | 689 | 135.1 | 7.4 |

Figure 14 A and B

| | | |
|---|---|---|
| F67S | F67S F86Y | F67S A209T |
| G138D | G138D F86Y | G138D A209T |
| E157K | E157K F86Y | E157K A209T |
| R171K | R171K F86Y | R171K A209T |
| V9I G138D | V9I G138D F86Y | V9I G138D A209T |
| V9I E157K | V9I E157K F86Y | V9I E157K A209T |
| V9I R171K | V9I R171K F86Y | V9I R171K A209T |
| F177L | F177L F86Y | F177L A209T |
| F67S F177L | F67S F177L F86Y | F67S F177L A209T |
| C195S | C195S F86Y | C195S A209T |
| G138S | G138S F86Y | G138S A209T |
| C68R | C68R F86Y | C68R A209T |
| V9I F67S | V9I F67S F86Y | V9I F67S A209T |
| F67S G138D | F67S G138D F86Y | F67S G138D A209T |
| F67S E157K | F67S E157K F86Y | F67S E157K A209T |
| F67S R171K | F67S R171K F86Y | F67S R171K A209T |
| V9I F67S G138D | V9I F67S G138D F86Y | V9I F67S G138D A209T |
| V9I F67S E157K | V9I F67S E157K F86Y | V9I F67S E157K A209T |
| V9I F67S R171K | V9I F67S R171K F86Y | V9I F67S R171K A209T |
| V9I G138D E157K | V9I G138D E157K F86Y | V9I G138D E157K A209T |
| V9I G138D R171K | V9I G138D R171K F86Y | V9I G138D R171K A209T |
| S12G F67S | S12G F67S F86Y | S12G F67S A209T |
| G19M F67S | G19M F67S F86Y | G19M F67S A209T |
| E37Q F67S | E37Q F67S F86Y | E37Q F67S A209T |
| C68R G138D | C68R G138D F86Y | C68R G138D A209T |
| G19M G138D | G19M G138D F86Y | G19M G138D A209T |
| E37Q G138D | E37Q G138D F86Y | E37Q G138D A209T |
| V9I C68R G138D | V9I C68R G138D F86Y | V9I C68R G138D A209T |
| V9I G19M G138D | V9I G19M G138D F86Y | V9I G19M G138D A209T |
| V9I E37Q G138D | V9I E37Q G138D F86Y | V9I E37Q G138D A209T |
| V9I G19M F67S G138D | V9I G19M F67S G138D F86Y | V9I G19M F67S G138D A209T |
| V9I S12G F67S G138D | V9I S12G F67S G138D F86Y | V9I S12G F67S G138D A209T |
| V9I F67S C68R G138D | V9I F67S C68R G138D F86Y | V9I F67S C68R G138D A209T |

Figure 14 C

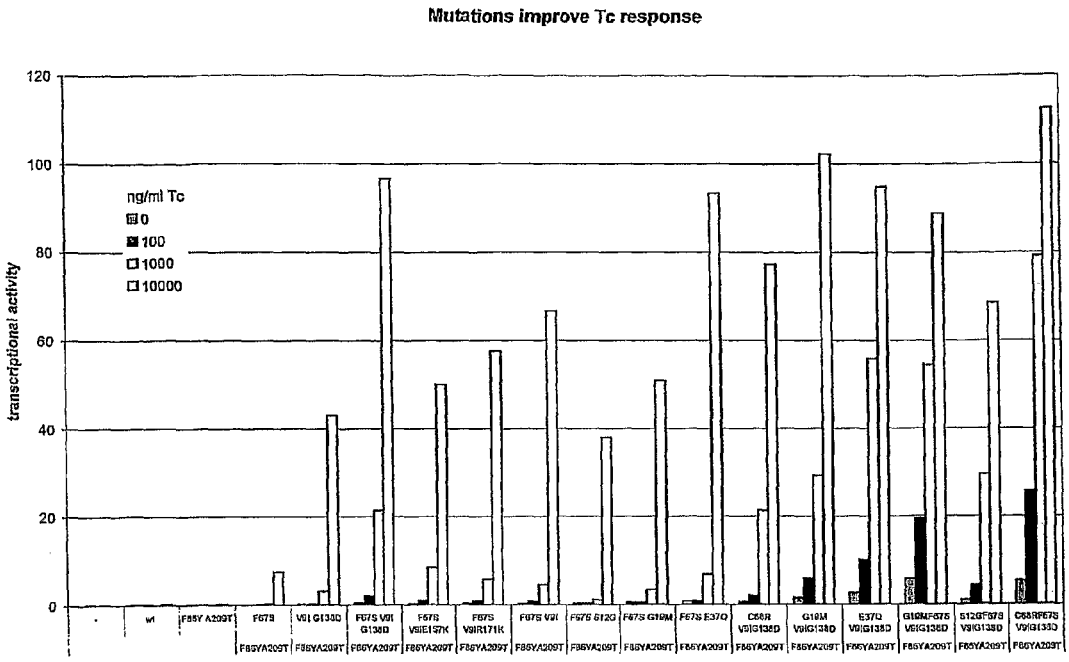
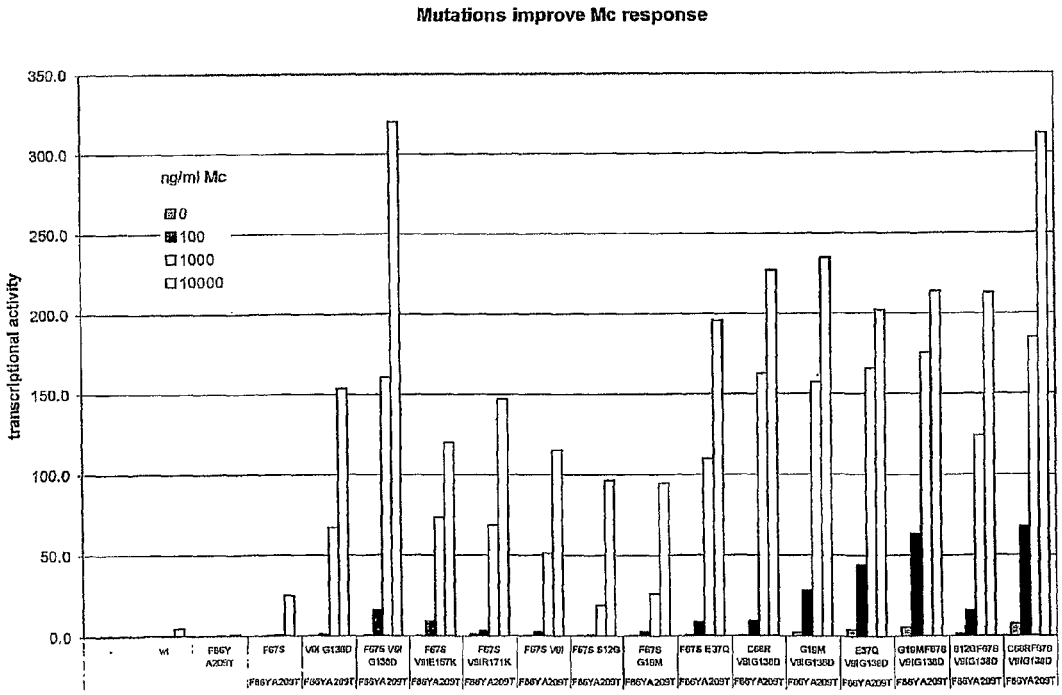
Figure 15

A
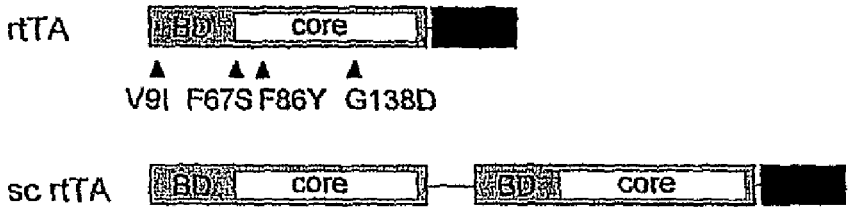
B
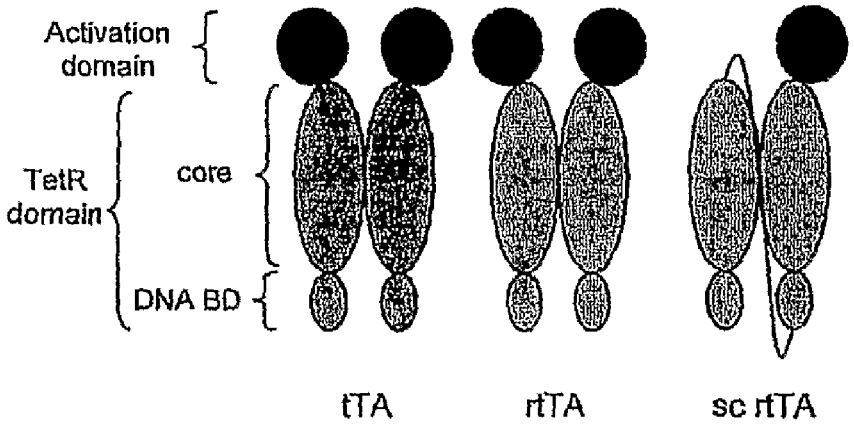
Figure 16

Figure 19: Nucleotide and amino acid sequence of rtTA

```
1      ATGTCTAGACTGGACAAGAGCAAAGTCATAAACTCTGCTCTGGAATTACTCAATGGAGTC
1       M  S  R  L  D  K  S  K  V  I  N  S  A  L  E  L  L  N  G  V

61     GGTATCGAAGGCCTGACGACAAGGAAACTCGCTCAAAAGCTGGGAGTTGAGCAGCCTACC
21      G  I  E  G  L  T  T  R  K  L  A  Q  K  L  G  V  E  Q  P  T

121    CTGTACTGGCACGTGAAGAACAAGCGGGCCCTGCTCGATGCCCTGCCAATCGAGATGCTG
41      L  Y  W  H  V  K  N  K  R  A  L  L  D  A  L  P  I  E  M  L

181    GACAGGCATCATACCCACTTCTGCCCCCTGGAAGGCGAGTCATGGCAAGACTTTCTGCGG
61      D  R  H  H  T  H  F  C  P  L  E  G  E  S  W  Q  D  F  L  R

241    AACAACGCCAAGTCATTCCGCTGTGCTCTCCTCTCACATCGCGACGGGGCTAAAGTGCAT
81      N  N  A  K  S  F  R  C  A  L  L  S  H  R  D  G  A  K  V  H

301    CTCGGCACCCGCCCAACAGAGAAACAGTACGAAACCCTGGAAAATCAGCTCGCGTTCCTG
101     L  G  T  R  P  T  E  K  Q  Y  E  T  L  E  N  Q  L  A  F  L

361    TGTCAGCAAGGCTTCTCCCTGGAGAACGCACTGTACGCTCTGTCCGCCGTGGGCCACTTT
121     C  Q  Q  G  F  S  L  E  N  A  L  Y  A  L  S  A  V  G  H  F

421    ACACTGGGCTGCGTATTGGAGGAACAGGAGCATCAAGTAGCAAAAGAGGAAAGAGAGACA
141     T  L  G  C  V  L  E  E  Q  E  H  Q  V  A  K  E  E  R  E  T

481    CCTACCACCGATTCTATGCCCCCACTTCTGAGACAAGCAATTGAGCTGTTCGACCGGCAG
161     P  T  T  D  S  M  P  P  L  L  R  Q  A  I  E  L  F  D  R  Q

541    GGAGCCGAACCTGCCTTCCTTTTCGGCCTGGAACTAATCATATGTGGCCTGGAGAAACAG
181     G  A  E  P  A  F  L  F  G  L  E  L  I  I  C  G  L  E  K  Q

601    CTAAAGTGCGAAAGCGGCGGGCCGGCCGACGCCCTTGACGATTTTGACTTAGACATGCTC
201     L  K  C  E  S  G  G  P  A  D  A  L  D  D  F  D  L  D  M  L

661    CCAGCCGATGCCCTTGACGACTTTGACCTTGATATGCTGCCTGCTGACGCTCTTGACGAT
221     P  A  D  A  L  D  D  F  D  L  D  M  L  P  A  D  A  L  D  D

721    TTTGACCTTGACATGCTCCCCGGGTAA
241     F  D  L  D  M  L  P  G  *
```

A
rtTA$_{G19F\ E37L}$ variants with all possible amino acids at position 56
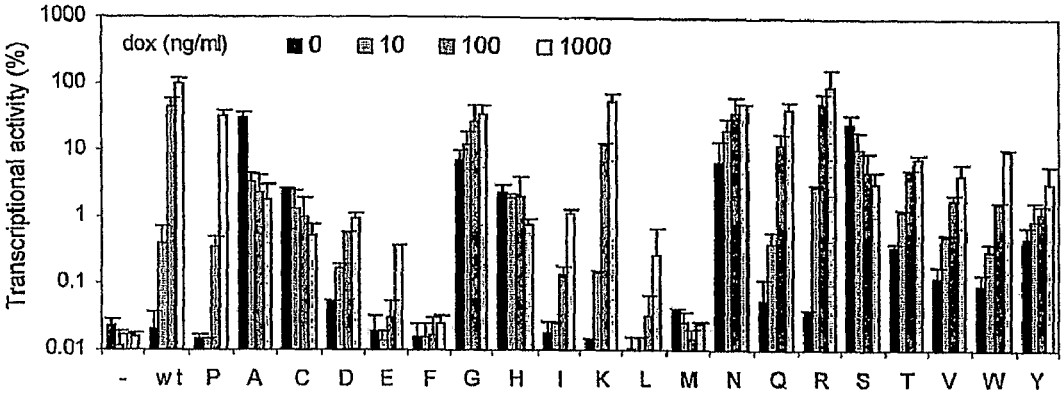
B
rtTA position 56 codon
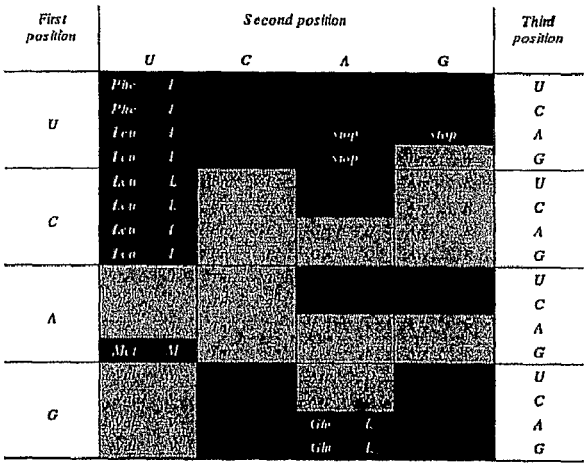
Figure 22

INDUCIBLE EXPRESSION SYSTEMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The invention relates to molecular biology, in particular to improved expression systems of nucleic acids.

BACKGROUND

Systems to modulate nucleic acid expression are important for a wide variety of basic and applied biological research areas, including functional genomics, gene therapy, vaccination, animal models for human diseases and biopharmaceutical protein production. In these applications, expression of a nucleic acid(s) of interest is preferably controlled in a quantitative and temporal way. Several artificial gene expression systems that are regulated by non-toxic effector molecules in a dose-dependent and reversible manner are currently available. The Tet system, in which gene expression is stringently controlled by tetracycline (Tc) or its derivative doxycycline (dox), is the most widely-used regulatory circuit (Baron et al. 2000; Gossen et al. 2001; Berens et al. 2003). This system is based on the sequence-specific, high-affinity binding of the Escherichia coli Tet repressor protein (TetR) to the tet operator (tetO) DNA sequence. Tc or dox binds to TetR and triggers a conformational change that prevents the repressor protein from binding to tetO. Fusion of the VP16 activation domain of herpes simplex virus to TetR resulted in the transcriptional activator tTA, which induces nucleic acid expression from tetO-containing promoters ($P_{tet}$) in eukaryotic cells (Gossen et al. 1992). The presence of Tc or dox abolishes tTA-tetO interaction and switches off gene expression (Tet-off system). A tTA variant with four amino acid substitutions in the TetR moiety was identified, which exhibits a reverse phenotype (Gossen et al. 1995). This reverse tTA (called rtTA) binds to $P_{tet}$ exclusively in the presence of dox, but not in its absence (Tet-on system). Both Tet systems are now widely applied to control nucleic acid expression in eukaryotes, including mammals, plants and insects (reviewed in (Gossen et al. 2001)). Because long-term exposure to effectors is often undesirable, the Tet-on system is preferred in applications in which nucleic acid expression is to be sustained in a switched-off state for long periods, or when rapid induction of nucleic acid expression is required.

Unfortunately, the amino acid substitutions in rtTA that confer the reverse phenotype also affect its binding affinity for effectors. As a consequence, rtTA has lost the ability to be activated by Tc and other Tc-like compounds, and it requires 100-fold more dox for maximal induction than that is needed for tTA inhibition. These characteristics severely limit the in vivo use of the Tet-on system. For example, to activate Tet-on controlled transgene expression in the rat brain, the animals have to be fed with high doses of dox that are nearly toxic (Baronet al. 1997). Therefore, the Tet-on system, particularly its effector-sensitivity, has to be improved.

Previously, the Tet system has been optimized by introduction of rationally designed mutations (Baron et al. 1997; Baron et al. 1999), and by directed evolution in which random mutagenesis of the components of the Tet system was followed by functional screening of the mutants in bacterial or yeast assay systems (Gossen et al. 1995; Urlinger et al. 2000). However, these approaches are labor intensive, and mutations selected in bacterial or yeast assay systems are not necessarily improvements in higher eukaryotes.

Another disadvantage of current rtTA systems is the risk of reduced dox-dependence after multiple rounds of replication. This problem, for instance, arises during vaccination applications where replication of at least part of a pathogen is under control of an rtTA system. In such vaccination applications, protection against the pathogen is acquired by controlled, inducible replication of the at least part of a pathogen, preferably during a restrained time span. If, however, the rtTA system loses its dox-dependence, the at least part of a pathogen will constitutively replicate, resulting in too much pathogenic nucleic acid and/or proteins, involving a safety problem. The same kind of problem arises during other applications involving repeated rounds of amplification of rtTA. It is therefore desired to improve the genetic stability of current rtTA systems.

DISCLOSURE

Provided are rtTA and single chain rtTA variants. Preferably, rtTA and single chain rtTA variants are provided with at least one improved property.

The invention provides a method for inducibly expressing a nucleic acid sequence of interest, the method comprising:

- providing a nucleic acid construct comprising the nucleic acid sequence of interest operably linked to an inducible gene expression system which comprises an rtTA encoding nucleic acid sequence and/or a single chain rtTA encoding nucleic acid sequence, the rtTA encoding nucleic acid sequence and/or single chain rtTA encoding nucleic acid sequence comprising a mutation in a codon at rtTA amino acid position 9, and/or 19, and/or 37, and/or 56, and/or 67, and/or 68, and/or 138, and/or 157, and/or 171, and/or 177, and/or 195;
- introducing the nucleic acid construct to a suitable expression system; and
- allowing for inducible expression of the nucleic acid sequence of interest.

In one embodiment, a mutation in at least one of the above mentioned codons of an rtTA nucleic acid or a single chain rtTA (sc rtTA) nucleic acid results in an improved rtTA or sc rtTA activator as compared to currently used Tet-on systems, such as described in (Gossen et al. 1995), (Urlinger et al. 2000) and (Krueger et al. 2003). Using an rtTA or sc rtTA variant, an improved rtTA or sc rtTA system is provided which has a higher transcriptional activity, a higher dox-sensitivity, a higher genetic stability and/or a lower level of transcription in the absence of an inducer, as compared to currently used rtTA or sc rtTA systems. The level of transcription in the absence of an inducer is called herein basal activity. Furthermore, rtTA and sc rtTA systems are provided which are inducible by antibiotics other than doxycycline. Hence, in some embodiments, the use of an rtTA and/or sc rtTA for inducibly expressing a nucleic acid sequence of interest is disclosed.

Some embodiments provide a method according to the invention wherein the rtTA encoding nucleic acid sequence and/or single chain rtTA encoding nucleic acid sequence further comprises a mutation in a codon at rtTA amino acid position 12, and/or 86, and/or 209. It has been shown that such additional mutations result in improved characteristics of the resulting rtTA and sc rtTA systems.

A single chain rtTA (sc rtTA) is a monomer comprising the same transregulating properties as the rtTA dimer in kind, not necessarily in amount. The sc rtTA preferably comprises two TetR moieties and one eukaryotic regulatory domain. The two TetR moieties are preferably connected to each other by a linker, the linker preferably comprising a sequence encoding an $(SG_4)_5$ linker, which is long and flexible enough to allow intramolecular assembly of the two TetR proteins. Non-limiting examples of single-chain Tet transregulators are described in (Krueger et al. 2003). The methods described therein on page 3050, last paragraph and page 3051 for generating a single chain tTA and/or a single chain rtTA are incorporated herein by reference. These methods are non-limiting examples of generating sc rtTA.

In one aspect, a mutation in a sc rtTA which corresponds to a mutation in an rtTA dimer transregulator results in an improved sc rtTA. A mutation in a sc rtTA corresponds to a mutation in an rtTA dimer when a mutation in a sc rtTA is present in a codon encoding an amino acid residue at a position within the sc rtTA which is comparable to rtTA amino acid position 9, 12, 19, 37, 56, 67, 68, 86, 138, 157, 171, 177, 195 and/or 209.

By inducibly expressing a nucleic acid sequence of interest is meant herein that expression of a nucleic acid of interest is at least in part influenced by at least one inducer. Hence, by regulating the amount of inducer that is administered to the expression system, one may regulate the amount of expression of the nucleic acid sequence of interest. The inducer may comprise an exogenous compound, meaning that the compound is not naturally present within the expression system. Preferably, expression of a nucleic acid sequence of interest is dependent on the presence of an inducer. This means that the nucleic acid is expressed in the presence of an inducer, while it is expressed to a significantly lesser extent in the absence of the inducer. Preferably, the nucleic acid sequence is essentially not expressed in absence of the inducer.

A nucleic acid sequence of interest is operably linked to an inducible nucleic acid expression system when the inducible nucleic acid expression system is capable of expressing the nucleic acid sequence of interest. In embodiments, the nucleic acid sequence of interest is under control of a tetO-containing promoter. Expression of the nucleic acid of interest is at least in part inhibited in the absence of an inducer, since rtTA and/or sc rtTA does not activate tetO-driven expression when an inducer is absent. In the presence of an inducer, rtTA and/or sc rtTA are able to activate tetO-driven expression of the nucleic acid of interest.

In embodiments, an rtTA or sc rtTA nucleic acid sequence is defined as an rtTA or sc rtTA nucleic acid sequence derived from an rtTA or sc rtTA sequence (Urlinger et al. 2000; Das et al. 2004; Krueger et al. 2003), which rtTA or sc rtTA sequence has been provided with at least one mutation as described herein. In some embodiments, at least one mutation according to the invention is introduced into the rtTA sequence depicted in FIG. 19. In certain embodiments, a method is provided wherein the rtTA encoding nucleic acid sequence and/or single chain rtTA encoding nucleic acid sequence comprises at least one mutation or combination of mutations according to the invention as compared to an rtTA encoding nucleic acid sequence depicted in FIG. 19.

In embodiments, an rtTA nucleic acid and/or a sc rtTA nucleic acid may be mutated in a variety of ways. It is, for instance, possible to artificially introduce at least one mutation in an rtTA or sc rtTA nucleic acid via site directed mutagenesis. Various methods for artificially introducing a specific mutation are known in the art and do not require further explanation here. Once a mutation or a combination of mutations is introduced, an rtTA or sc rtTA nucleic acid of the invention may be further amplified. Amplified rtTA or sc rtTA comprising a mutation is thus also herewith provided. It is clear that it is no longer necessary to artificially introduce a mutation once an rtTA or sc rtTA nucleic acid sequence of the invention is available, since a mutation in some embodiments of the invention is retained during amplification.

In some embodiments, an rtTA and/or sc rtTA with at least one mutation may be selected from a collection of rtTA/sc rtTA nucleic acids. For instance, non-specific mutations may be introduced into a collection of rtTA/sc rtTA nucleic acids, and a nucleic acid molecule comprising at least one mutation is selected (optionally after amplification). In an embodiment, rtTA or sc rtTA nucleic acid of the invention is selected from a collection of amplified rtTA or sc rtTA via an evolution and selection method. Since a mutation may provide at least one advantage to an rtTA/sc rtTA nucleic acid, it is possible to select a nucleic acid with a mutation of the invention on the basis of such advantage. For instance, a mutation resulting in enhanced sensitivity for dox may be selected using very small amounts of dox. An inducible gene expression system may, for example, be incubated with a very small amount of dox, and sensitive systems selected. As another example, a mutation resulting in diminished basal activity may be selected by selecting an inducible nucleic acid expression system with very little, if any, activity in the absence of an inducer.

In one embodiment, forced evolution is used in order to generate and select an rtTA and/or sc rtTA nucleic acid with at least one mutation. In such a method, amplification of rtTA or sc rtTA may be performed using a method which involves the introduction of mismatches. This is preferably performed using a genome of a virus comprising RNA, because the error-prone nature of its replication machinery (e.g., the reverse transcriptase (RT) enzyme or RNA polymerase enzyme) allows for the generation of modified nucleic acid sequences. This way, altered rtTA/sc rtTA nucleic acid molecules are produced. If such altered nucleic acid sequences comprise a mutation, the nucleic acid will have an advantage over nucleic acid sequences without a mutation. As a result, nucleic acid molecules comprising at least one mutation will outgrow nucleic acid molecules without a mutation. As a result, an rtTA and/or sc rtTA nucleic acid comprising at least one mutation may be easily selected.

In one embodiment, a forced evolution method is used with help of a Human Immunodeficiency Virus-1 (HIV-1) genome, as described in WO 01/20013 page 21, lines 5-28, incorporated herein by reference.

As used herein, an rtTA or sc rtTA variant is represented by the term "X[number]Y", wherein X represents the kind of amino acid residue present in a currently used rtTA activator, [number] represents the position of the amino acid residue in the rtTA, and Y represents the amino acid residue that is currently present at the position in the variant. For instance, V9I means a variant which comprises at rtTA amino acid position 9 an isoleucine residue instead of a valine residue. Variants comprising multiple mutations are represented by multiple X[number]Y indications. Hence, variant V9I F67S R171K F86Y means a variant which comprises at rtTA amino acid position 9 an isoleucine instead of a valine and which comprises at rtTA amino acid position 67 a serine instead of a phenylalanine and which comprises at rtTA amino acid position 171 a lysine instead of an arginine and which comprises at rtTA amino acid position 86 a tyrosine instead of a phenylalanine.

Which mutation, or which combination of mutations, is used in a specific application is for instance dependent on the kind of advantage(s) that is desired. For instance, for inducible in vivo transgene expression in a brain, a sensitive rtTA and/or sc rtTA nucleic acid is particularly desired, since only a small amount of inducer is capable of passing the blood brain barrier. For such applications, an rtTA/sc rtTA nucleic acid with a mutation at least resulting in improved sensitivity is preferred. In that case, variant V9I F67S G138D F86Y, V9I F67S G138D F86Y A209T, V9I F67S E157K F86Y, V9I F67S E157K F86Y A209T, V9I F67S R171K F86Y, V9I F67S R171K F86Y A209T, E37Q F67S F86Y, E37Q F67S F86Y A209T, V9I C68R G138D F86Y, V9I C68R G138D F86Y A209T, V9I G19M G138D F86Y, V9I G19M G138D F86Y A209T, V9I E37Q G138D F86Y, V9I E37Q G138D F86Y A209T, V9I G19M F67S G138D F86Y, V9I G19M F67S G138D F86Y A209T, V9I S12G F67S G138D F86Y, V9I S12G F67S G138D F86Y A209T, V9I F67S C68R G138D F86Y and/or V9I F67S C68R G138D F86Y A209T are preferred because these variants have more than 100-fold doxycyclin sensitivity as compared to rtTA, with no or low basal activity in the absence of inducer (as indicated in FIG. 14B). If some level of basal activity in the absence of inducer is not a problem, a V9I G19M F67S G138D F86Y and/or V9I G19M F67S G138D F86Y A209T rtTA variant is particularly preferred, which is more than 300 times more sensitive for doxycyclin induction as compared to rtTA (indicated in FIG. 14).

Furthermore, an rtTA or sc rtTA variant comprising an alanine, cysteine, aspartate, phenylalanine, histidine, isoleucine, lysine, leucine, methionine, asparagine, glutamine, arginine, serine, threonine valine or tyrosine residue at rtTA amino acid position 19 has an improved transcriptional activity as compared to currently known rtTA. The variants have an increased transcriptional activity at a low doxycycline concentration (between 10 and 100 ng/ml) and/or an increased transcriptional activity at a high doxycycline concentration (between 100 and 1000 ng/ml), as compared to currently known rtTA. One embodiment therefore provides an isolated, synthetic or recombinant amino acid sequence comprising an rtTA sequence and/or a sc rtTA sequence, which rtTA sequence and/or sc rtTA sequence comprises an alanine, cysteine, aspartate, phenylalanine, histidine, isoleucine, lysine, leucine, methionine, asparagine, glutamine, arginine, serine, threonine, valine or tyrosine at rtTA amino acid position 19. An isolated, synthetic or recombinant nucleic acid sequence comprising a sequence encoding an rtTA sequence and/or a sc rtTA sequence, which rtTA sequence and/or sc rtTA sequence comprises an alanine, cysteine, aspartate, phenylalanine, histidine, isoleucine, lysine, leucine, methionine, asparagine, glutamine, arginine, serine, threonine valine or tyrosine at rtTA amino acid position 19 is also provided, as well as a use of the nucleic acid sequence in a method for inducible expression of a nucleic acid sequence of interest.

An rtTA or sc rtTA variant comprising a cysteine, methionine, glutamine, arginine or threonine residue at rtTA amino acid position 37 has an improved transcriptional activity as compared to currently known rtTA. The variants have increased transcriptional activity at a low doxycycline concentration (between 10 and 100 ng/ml) and/or increased transcriptional activity at a high doxycycline concentration (between 100 and 1000 ng/ml), as compared to currently known rtTA. One embodiment therefore provides an isolated, synthetic or recombinant amino acid sequence comprising an rtTA sequence and/or a sc rtTA sequence, which rtTA sequence and/or sc rtTA sequence comprises a cysteine, methionine, glutamine, arginine or threonine residue at rtTA amino acid position 37. An isolated, synthetic or recombinant nucleic acid sequence comprising a sequence encoding an rtTA sequence and/or a sc rtTA sequence, which rtTA sequence and/or sc rtTA sequence comprises a cysteine, methionine, glutamine, arginine or threonine residue at rtTA amino acid position 37 is also herewith provided, as well as the use of the nucleic acid sequence in a method according to the invention for inducibly expressing a nucleic acid sequence of interest.

If an rtTA and/or sc rtTA nucleic acid is used for vaccination purposes involving controlled expression of a (pathogen-derived) nucleic acid sequence of interest, it is important that basal activity is minimal. Expression of a pathogenic nucleic acid of interest in the absence of an inducer is undesired, because it would result in the continuous presence of the pathogenic nucleic acid of interest. In that case, an organism would be challenged too much with pathogenic nucleic acid, which could result in disease and/or tolerance of the immune system for the pathogenic nucleic acid of interest. If tolerance is induced, protection against a subsequent challenge with the pathogen is diminished. Avoiding this type of basal activity is particularly important if the replication of a viable pathogen is inducibly controlled by an rtTA and/or sc rtTA system. Continuous replication of the pathogen involves the risk of spreading and outgrowth of too many pathogenic organisms, resulting in disease. For vaccination purposes, an rtTA and/or sc rtTA variant with a very low basal activity, if any, is therefore preferred in some embodiments. In such cases, variant F67S F86Y, F67S F86Y A209T, G138D F86Y, G138D F86Y A209T, E157K F86Y, E157K F86Y A209T, R171K F86Y, R171K F86Y A209T, V9I G138D F86Y, V9I G138D F86Y A209T, V9I E157K F86Y, V9I E157K F86Y A209T, V9I R171K F86Y, V9I R171K F86Y A209T, F177L F86Y, F177L F86Y A209T, F67S F177L F86Y, F67S F177L F86Y A209T, C195S F86Y, C195S F86Y A209T, G138S F86Y, G138S F86Y A209T, C68R F86Y, C68R F86Y A209T, F67S G138D F86Y, F67S G138D F86Y A209T, F67S E157K F86Y, F67S E157K F86Y A209T, F67S R171K F86Y, F67S R171K F86Y A209T, V9I F67S R171K F86Y, V9I F67S R171K F86Y A209T, S12G F67S F86Y, S12G F67S F86Y A209T, G19M F67S F86Y and/or G19M F67S F86Y A209T may be used. These variants have a very low basal activity of 0.1 percent or less. A V9I F67S R171K F86Y and/or V9I F67S R171K F86Y A209T rtTA variant may preferably be used. These variants have a very low basal activity and are very sensitive, because they have a more than 100-fold doxycyclin sensitivity as compared to rtTA (indicated in FIG. 14).

The invention furthermore provides rtTA and sc rtTA variants with altered inducer-specificities. rtTA and sc rtTA variants are provided that are inducible by antibiotics other than doxycycline. Hence, although other dox-like compounds such as tetracycline (Tc) and minocycline (Mc) do not effectively activate wild type rtTA, variants are provided herein that have become inducible by at least one of these antibiotics. This provides amongst other things the advantage that tetracycline is suitable as an inducer, which is cheaper than doxycycline. Furthermore, rtTA and sc rtTA variants for use in some embodiments that are inducible by antibiotics other than doxycycline are suitable for the development of rtTA and/or sc rtTA variants with an altered specificity, and are inducible by at least one antibiotic other than doxycycline, but not by doxycycline itself. FIG. 15 shows certain variants that are responsive to tetracycline and/or minocycline, except for the wild type rtTA and the F86Y A209T mutant.

Some embodiments therefore provide an isolated, synthetic or recombinant nucleic acid sequence comprising an rtTA encoding nucleic acid sequence and/or a single chain rtTA encoding nucleic acid sequence, which rtTA encoding nucleic acid sequence and/or single chain rtTA encoding nucleic acid sequence comprises a mutation or a combination of mutations as depicted in FIG. 15, except for the F86Y A209T mutation (and, of course, except for the wild type variant). A use of at least one of the nucleic acid sequences for tetracycline-inducible and/or minocycline-inducible expression of a nucleic acid sequence of interest is also herewith provided. In some embodiments, mutant F67S V9I G138D F86Y A209T, C68R V9I G138D F86Y A209T, G19M V9I G138D F86Y A209T, E37Q V9I G138D F86Y A209T, G19M F67S V9I G138D F86Y A209T, 512G F67S V9I G138D F86Y A209T and/or C68R F67S V9I G138D F86Y A209T may be used for tetracycline-inducible expression of a nucleic acid sequence of interest since these mutants are particularly sensitive for tetracycline, meaning that a small amount of tetracycline is sufficient for inducing gene expression. Preferably, mutant F67S V9I G138D F86Y A209T, C68R V9I G138D F86Y A209T and/or S12G F67S V9I G138D F86Y A209T may be used for tetracycline-inducible expression of a nucleic acid sequence of interest, since these mutants are very sensitive for tetracycline and show low background activity in the absence of any effector.

In a further embodiment, mutant V9I G138D F86Y A209T, F67S V9I G138D F86Y A209T, F67S V9I E157K F86Y A209T, F67S V9I R171K F86Y A209T, F67S E37Q F86Y A209T, C68R V9I G138D F86Y A209T, G19M V9I G138D F86Y A209T, E37Q V9I G138D F86Y A209T, G19M F67S V9I G138D F86Y A209T, S12G F67S V9I G138D F86Y A209T and/or C68R F67S V9I G138D F86Y A209T may be used for minocycline-inducible expression of a nucleic acid sequence of interest, since these mutants are particularly sensitive for minocycline, meaning that a small amount of minocycline is sufficient for inducing gene expression. Preferably, mutant F67S V9I G138D F86Y A209T, F67S E37Q F86Y A209T, C68R V9I G138D F86Y A209T and/or S12G F67S V9I G138D F86Y A209T may be used for minocycline-inducible expression of a nucleic acid sequence of interest since these mutants are very sensitive for minocycline and show low background activity in the absence of any effector.

In some aspects, the invention further provides rtTA and sc rtTA variants that are genetically stable. Currently used inducible Tet-on systems are at risk of converting into a system constitutively expressing a nucleic acid sequence of interest. This is preferably avoided, for instance (among other things) when replication of a pathogen is controlled by a Tet-on system. Constitutive replication of the pathogen could result in the presence of too many pathogens, increasing the risk of disease and/or tolerance.

In embodiments, the genetic stability of an inducible gene expression system comprising rtTA and/or sc rtTA nucleic acid is improved by altering a codon at rtTA amino acid position 19, 37 and/or 56 (and/or the corresponding codons in sc rtTA) such that loss of inducer dependency is at least in part prevented. Reduction and/or loss of inducer-dependence of currently used rtTA and sc rtTA result from at least one mutation at rtTA amino acid position 19, 37 and/or 56, such as for instance a G19E, E37K, E37A, E37S and/or a P56S mutation. According to the invention, replacement of the glycine residue at rtTA amino acid position 19 by a glutamic acid residue results in at least partial loss of inducer-dependence of rtTA/sc rtTA. Moreover, replacement of the glutamic acid residue at rtTA amino acid position 37 by a lysine, alanine or serine residue results in at least partial loss of inducer-dependence of rtTA/sc rtTA. Moreover, replacement of the proline residue at rtTA amino acid position 56 by serine, tyrosine, cysteine, histidine, asparagine, alanine or glycine results in at least partial loss of inducer-dependence of rtTA/sc rtTA. Some embodiments therefore provide modified rtTA and/or sc rtTA nucleic acids wherein spontaneous mutations that would result in at least partial loss of inducer-dependence are less likely to occur, as compared to currently used rtTA/sc rtTA. Such variants may be obtained as described in the following paragraph.

In currently used rtTA, a G19E mutation requires only one nucleotide change in codon 19, namely the codon change G GA to GAA. The G-to-A transition is the most frequent error during reverse transcription of RNA. In some embodiments, reduction and/or loss of inducer-dependency of rtTA and/or sc rtTA may be at least in part prevented by using an altered codon at position 19 that is not as easily converted into a glutamic acid codon. This may be performed, for example, by using a codon at position 19 that differs in at least two nucleotides from a glutamic acid codon. If such codon is used, an undesired G19E mutation would require a much more difficult two-hit mutation. Hence, when an rtTA and/or sc rtTA nucleic acid is used with a codon at rtTA position 19 which differs in at least two nucleotides from a glutamic acid codon, an undesired G19E mutation is less likely to evolve, as compared to currently used Tet-on systems. Reduction and/or loss of inducer-dependence may therefore at least in part be prevented. The invention therefore provides a method according to the invention wherein the rtTA encoding nucleic acid sequence and/or single chain rtTA encoding nucleic acid sequence comprises a codon at rtTA amino acid position 19 which differs in at least two nucleotides from a glutamic acid codon.

In one embodiment, an alternative glycine codon at position 19 is used which differs in at least two nucleotides from a glutamic acid codon. For example, the alternative glycine codon GGU or GGC may be used (instead of GGA, which is present in currently used rtTA). A G19E mutation is much more difficult in this embodiment because it requires a GGU to GAA, a GGU to GAG, a GGC to GAA or a GGC to G AG change. Hence, in these cases, a two-hit mutation may be required. Since this is less likely to occur, an rtTA and/or sc rtTA with such an alternative glycine codon is less likely to lose its inducer-dependence. When the alternative glycine codon is used, the resulting amino acid residue of the rtTA or sc rtTA activator at rtTA position 19 is the same as the activator encoded by currently used rtTA and sc rtTA nucleic acid. One embodiment therefore provides a method wherein the rtTA encoding nucleic acid sequence and/or single chain rtTA encoding nucleic acid sequence comprises a glycine codon at rtTA amino acid position 19 which differs in at least two nucleotides from a glutamic acid codon.

In certain embodiments, an rtTA or sc rtTA nucleic acid may be used which comprises an alanine, cysteine, phenylalanine, histidine, isoleucine, leucine, methionine, asparagine, arginine, serine, threonine, valine, tryptophan or tyrosine codon at rtTA amino acid position 19 which differs in at least two nucleotides from a glutamic acid codon. A nucleic acid according to this embodiment is not only genetically more stable, but—except for the G19W variant—is also more sensitive for doxycycline. One embodiment therefore provides a method wherein the rtTA encoding nucleic acid sequence and/or single chain rtTA encoding nucleic acid sequence comprises an alanine, cysteine, phenylalanine, histidine, isoleucine, leucine, methionine, asparagine, arginine, serine, threonine, valine, tryptophan or tyrosine codon at rtTA amino acid position 19 which differs in at least two nucleotides from a glutamic acid codon. Suitable codons at rtTA amino acid position 19 which differ in at least two nucleotides from a glutamic acid codon include codon UUN (with N corresponding to G, A, U, or C (coding for Phenylalanine or Leucine), UCN (Serine), UAY (with Y corresponding to U or C; Tyrosine), UGU (Cysteine), UGC (Cysteine), UGG (Tryptophan), GUN (Leucine), CAY (Histidine), CGN (Arginine), AUN (Isoleucine or Methionine), ACN (Threonine), AAY (Asparagine), AGN (Serine or Arginine), GUY (Valine) and GCY (Alanine).

In an embodiment, a method is provided wherein the rtTA encoding nucleic acid sequence and/or single chain rtTA encoding nucleic acid sequence comprises a cysteine, phenylalanine, isoleucine, leucine, arginine, serine or threonine codon at rtTA amino acid position 19 which differs in three nucleotides from a glutamic acid codon. Such variant is in particular genetically stable because three mutations would be required in order to generate a G19E variant. Suitable codons at rtTA amino acid position 19 which differ in at least three nucleotides from a glutamic acid codon are codon UUY (with Y corresponding to U or C; coding for Phenylalanine), UCY (Serine), UGY (Cysteine), CUY (Leucine), CGY (Arginine), AUY (Isoleucine), ACY (Threonine) and AGY (Serine).

An rtTA or sc rtTA nucleic acid comprising a codon at rtTA amino acid position 37 which differs in at least two nucleotides from an alanine, a lysine and a serine codon is also provided. If such variant is used, spontaneous E37K, E37A and E37S mutation is less likely to occur, as compared to currently used rtTA/sc rtTA, because that would require a much more difficult two-hit mutation. As a consequence, loss of inducer dependency is at least in part avoided. Embodiments therefore provide a method wherein the rtTA encoding nucleic acid sequence and/or single chain rtTA encoding nucleic acid sequence comprises a codon at rtTA amino acid position 37 which differs in at least two nucleotides from an alanine, a lysine or a serine codon. Suitable codons at rtTA amino acid position 37 which differ in at least two nucleotides from an alanine, a lysine or a serine codon include codon CUN (coding for leucine, N stands for U, C, A or G), CAU, CAC (both CAU and CAC coding for histidine), CGA and CGG (both CGA and CGG coding for arginine). A rtTA encoding nucleic acid sequence and/or single chain rtTA encoding nucleic acid sequence comprising codon CUN, CAU, CAC, CGA or CGG at rtTA amino acid position 37 is therefore provided.

One embodiment provides a method wherein the rtTA encoding nucleic acid sequence and/or single chain rtTA encoding nucleic acid sequence comprises a codon at rtTA amino acid position 19 which differs in at least two nucleotides from a glutamic acid codon and a codon at rtTA amino acid position 37 which differs in at least two nucleotides from an alanine, a lysine or a serine codon. Such variant is particularly genetically stable, since spontaneous G19E, E37K, E37A and E37S mutations are at least in part prevented.

An rtTA and/or sc rtTA nucleic acid comprising an altered codon at rtTA amino acid position 56 also provides enhanced stability. It has been found that in the absence of doxycycline, rtTA variants are at risk of evolving to variants that have an altered amino acid residue at rtTA amino acid position 56, and that are no longer dependent on doxycycline. Some embodiments therefore provide an isolated, recombinant or synthetic nucleic acid sequence comprising an rtTA and/or sc rtTA encoding nucleic acid sequence which comprises a codon at rtTA amino acid position 56 which differs in at least one nucleotide, for example a transversion, from a codon that mediates transcriptional activity in the absence of an inducer. Most of these doxycycline-independent rtTA variants contain either a serine, tyrosine, cysteine, histidine, asparagine, alanine or glycine residue at position 56 instead of a proline. In order to at least in part avoid the development of such variants, an rtTA and/or sc rtTA encoding nucleic acid is preferably provided which comprises a CAA or CAG codon encoding glutamine or an AAA or AAG codon encoding lysine at rtTA amino acid position 56.

A transversion is defined herein as a substitution of a purine into a pyrimidine, or a substitution of a pyrimidine into a purine. A transversion is less likely to occur during natural evolution as compared to a substitution of a purine into another purine, or a substitution of a pyrimidine into another pyrimidine. Therefore, an rtTA and/or sc rtTA encoding nucleic acid sequence which comprises a codon at rtTA amino acid position 56 which differs in at least one transversion from a codon encoding a serine, tyrosine, cysteine, histidine, asparagine, alanine or glycine residue is genetically more stable as compared to current rtTA and sc rtTA.

An rtTA or sc rtTA nucleic acid with at least one mutated codon at rtTA amino acid position 9, 19, 37, 56, 67, 68, 138, 157, 171, 177, and/or 195 comprises at least one improved characteristic as compared to currently available Tet-on systems. In an embodiment, a method is therefore provided wherein the rtTA encoding nucleic acid sequences and/or single chain rtTA encoding nucleic acid sequence comprise a codon at rtTA amino acid position 9 encoding isoleucine, and/or a codon at rtTA amino acid position 19 encoding alanine, cysteine, aspartate, phenylalanine, histidine, isoleucine, lysine, leucine, methionine, asparagine, glutamine, arginine, serine, threonine, valine, tryptophan or tyrosine, and/or a codon at rtTA amino acid position 37 encoding threonine, histidine, leucine, arginine, cysteine, methionine or glutamine, and/or a codon at rtTA amino acid position 56 encoding lysine or glutamine, and/or a codon at rtTA amino acid position 67 encoding serine, and/or a codon at rtTA amino acid position 68 encoding arginine, and/or a codon at rtTA amino acid position 86 encoding tyrosine, and/or a codon at rtTA amino acid position 138 encoding aspartate or serine, and/or a codon at rtTA amino acid position 157 encoding lysine, and/or a codon at rtTA amino acid position 171 encoding lysine, and/or a codon at rtTA amino acid position 177 encoding leucine, and/or a codon at rtTA amino acid position 195 encoding serine, and/or a codon at rtTA amino acid position 209 encoding threonine. Any of these mutations, or any combination of them, is expected to improve at least one property of an inducible nucleic acid expression system.

In order to improve rtTA and/or sc rtTA, it is sufficient to introduce one mutation into an rtTA and/or sc rtTA encoding nucleic acid sequence. Preferably, at least two mutations are introduced, since a combination of at least two mutations further improves at least one property of rtTA and/or sc rtTA. In embodiments, an rtTA nucleic acid and/or a sc rtTA nucleic acid comprises at least three mutations as described herein. Most preferably, an rtTA nucleic acid and/or a sc rtTA nucleic acid comprises at least four mutations.

In FIG. 14, several variants of rtTA and/or sc rtTA are depicted. These variants may be used in an inducible gene expression system. Embodiments therefore further provide a method wherein the rtTA encoding nucleic acid sequence and/or single chain rtTA encoding nucleic acid sequence comprises at least one variant as depicted in FIG. 14. In one embodiment, a nucleic acid sequence of interest is inducibly expressed by rtTA variant V9I G19M F67S G138D F86Y and/or by variant V9I G19M F67S G138D F86Y A209T. These variants are about 385-fold more sensitive for doxycycline as compared to currently used rtTA. Hence, these variants are particularly suitable for applications wherein small amounts of inducer is available and/or desired (for instance during transgene expression in a brain). In another preferred embodiment a nucleic acid sequence of interest is inducibly expressed by rtTA variant V9I F67S R171K F86Y and/or by variant V9I F67S R171K F86Y A209T. These variants are about 100-fold more sensitive for doxycycline as compared to currently used rtTA, while at the same time basal activity is very low (about 0.1 percent). Hence, these variants are particularly suitable for applications wherein sensitivity for doxycycline is desired, while basal activity is undesired (for instance during inducible expression of a pathogen).

A mutation in certain embodiments is furthermore suitable for improving at least one characteristic of alternative rtTA and/or TetR derived molecules, besides rtTA and sc rtTA. Such alternative rtTA and/or TetR derived molecules may, for instance, comprises an alternative transcriptional activation domain (see for example [Akagi et al. 2001] and [Kamper et al. 2002]), or a transcriptional silencer in which the activation domain has been replaced by a transcriptional repressor domain (tTS, see for example [Deuschle et al. 1995]), or the tTA transcriptional activator, which is active in the absence of an effector and repressed by an effector (Gossen and Bujard, 1992).

Any inducible nucleic acid expression system comprising an rtTA and/or sc rtTA nucleic acid sequence and/or an alternative molecule derived thereof may be suitable for inducibly expressing a nucleic acid sequence of interest. In vivo as well as ex vivo applications are possible.

In one embodiment, a prokaryotic nucleic acid expression system is used. Preferably, the nucleic acid of interest is expressed in a eukaryotic expression system, because an rtTA and/or sc rtTA sequence comprising a VP16 activation domain of herpes simplex virus is particularly suitable for regulating nucleic acid expression from tetO-containing promoters in eukaryotic cells. An rtTA and/or sc rtTA nucleic acid sequence for use in some embodiments, and alternative molecules derived thereof, may be suitable for use in a lower eukaryotic expression system. Moreover, an rtTA and/or sc rtTA nucleic acid sequence hereof and alternative molecules derived thereof may be suitable for use in a higher eukaryotic expression system. In one embodiment a nucleic acid of interest and/or an alternative molecule derived thereof is expressed in a mammalian cell.

In principle, any nucleic acid sequence of interest may be inducibly expressed by a nucleic acid expression system. For instance, suitable applications for an inducible gene expression system in embodiments are the production of protein pharmaceuticals, in vivo expression of therapeutic proteins and production of transgenic animals wherein a (pathogenic) gene of interest is inducibly expressed, to name just a few. In one embodiment, at least one viral sequence essential for replication of a virus or replicon may be inducibly expressed by a nucleic acid expression system. This is particularly suitable for vaccination purposes in order to provide at least partial protection to a viral pathogen, wherein it is important that the virus or replicon replicates in order to obtain an efficacious immune response, but wherein it is also important that the replication does not go beyond the level required for the immune response. A replicon is defined as a nucleic acid molecule capable of replication in a suitable environment, such as a permissive cell, because it has all the necessary elements for replication in such an environment. We call it a replicon, because it will not always be directly derived from the nucleotide sequences of the original pathogen.

By placing at least one viral sequence essential for replication of a virus or replicon under control of an rtTA and/or sc rtTA nucleic acid sequence of the invention, the virus or replicon replicates in a controlled manner. The amount of replication necessary for eliciting a favorable immune response, without any replication beyond that level, may be thus regulated by regulating the amount of inducer that is administered to an inducible nucleic acid expression system. In order to prevent leakage, a combination of essential genes under such control may be used; preferably, at least two different repressor/activator combinations may be under control of at least one, but preferably more than one gene essential for replication. In most (viral) pathogens a number of genes are essential for replication, but most of them also have a sort of "master switch," usually an early gene, capable of transactivating other genes. A first candidate to put under direct control of a repressor/activator is, of course, such a master switch, which then indirectly provides control over other essential genes for replication. It may be preferred to put at least one other essential gene under control of an inducible repressor/activator.

In one embodiment, at least part of an HIV genome essential for replication is inducibly expressed under control of an rtTA and/or sc rtTA nucleic acid sequence of the invention. This is, for instance, suitable for improved AIDS prophylaxis as compared to currently known methods. In this embodiment, a master switch is not required since an HIV genome is under control of a single transcription unit.

A nucleic acid sequence comprising an rtTA nucleic acid sequence and/or a sc rtTA nucleic acid sequence, the rtTA nucleic acid sequence and/or sc rtTA nucleic acid sequence comprising at least one mutation, finds utility in a wide variety of applications. The nucleic acid sequence is particularly suitable for use in an inducible nucleic acid sequence expression system. Embodiments thus provide an isolated, synthetic or recombinant nucleic acid sequence comprising an rtTA encoding nucleic acid sequence and/or a single chain rtTA encoding nucleic acid sequence, which rtTA encoding nucleic acid sequence and/or single chain rtTA encoding nucleic acid sequence comprises a mutated codon at rtTA amino acid position 9, and/or 19, and/or 37, and/or 56, and/or 67, and/or 68, and/or 138, and/or 157, and/or 171, and/or 177, and/or 195. In one embodiment the nucleic acid sequence further comprises a mutated codon at rtTA amino acid position 12, and/or 86, and/or 209. A nucleic acid sequence comprising such combination of mutations is also improved as compared to currently known rtTA.

In a preferred embodiment, a nucleic acid sequence of the invention with an improved genetic stability as compared to currently used Tet-on systems is provided. This is particularly desired in applications involving multiple rounds of amplification of a nucleic acid sequence, for instance, during controlled replication of a viral pathogen or replicon. As explained above, genetic stability is improved by designing an rtTA and/or sc rtTA nucleic acid sequence with a codon at rtTA amino acid position 19 which differs in at least two nucleotides from a glutamate codon, with a codon at rtTA position 37 which differs in at least two nucleotides from an alanine, a lysine or a serine codon, and/or with a codon at rtTA position 56 encoding lysine or glutamine. Further provided is therefore an isolated, synthetic or recombinant nucleic acid sequence wherein the rtTA encoding nucleic acid sequence and/or single chain rtTA encoding nucleic acid sequence comprises a codon at rtTA amino acid position 19 which differs in at least two nucleotides from a glutamic acid codon, a codon at rtTA position 37 which differs in at least two nucleotides from an alanine, a lysine or a serine codon, and/or a codon at rtTA position 56 encoding lysine or glutamine. In one embodiment an rtTA encoding nucleic acid sequence and/or single chain rtTA encoding nucleic acid sequence comprises a glycine codon at rtTA amino acid position 19 which differs in at least two nucleotides from a glutamic acid codon, so that the resulting amino acid residue of the rtTA or sc rtTA activator at rtTA position 19 is the same as the activator encoded by currently used rtTA and sc rtTA nucleic acid.

An rtTA or sc rtTA nucleic acid may also be used which comprises an alanine, cysteine, phenylalanine, histidine, isoleucine, leucine, methionine, asparagine, arginine, serine, threonine, valine, tryptophan or tyrosine codon at rtTA amino acid position 19 which differs in at least two nucleotides from a glutamate codon. A nucleic acid according to this embodiment is not only genetically more stable, as compared to currently used Tet-on systems, but—except for the G19W variant—is also more sensitive for doxycycline. One embodiment provides an isolated, synthetic or recombinant nucleic acid sequence, wherein the rtTA encoding nucleic acid sequence and/or single chain rtTA encoding nucleic acid sequence comprises a leucine, a histidine or an arginine codon at rtTA amino acid position 37 which differs in at least two nucleotides from an alanine, a lysine or a serine codon.

A further embodiment provides an isolated, synthetic or recombinant nucleic acid sequence, wherein the rtTA encoding nucleic acid sequence and/or single chain rtTA encoding nucleic acid sequence comprises a codon at rtTA amino acid position 56 which differs in at least one nucleotide, preferably a transversion, from a codon that mediates transcriptional activity in the absence of inducer. The codon at rtTA amino acid position 56 preferably encodes a glutamine or a lysine residue.

In certain embodiments, an isolated, synthetic or recombinant nucleic acid sequence according to the invention is provided which comprises a codon at least two rtTA amino acid positions which are chosen from the group consisting of positions 19, 37 and 56. Some embodiments provide an isolated, synthetic or recombinant nucleic acid sequence according to the invention which comprises a codon at rtTA amino acid position 19 which differs in at least two nucleotides from a glutamic acid codon and a codon at rtTA position 37 which differs in at least two nucleotides from an alanine, a lysine or a serine codon. Further provided is an isolated, synthetic or recombinant nucleic acid sequence according to the invention which comprises a codon at rtTA amino acid position 19 which differs in at least two nucleotides from a glutamic acid codon and a codon at rtTA position 56 encoding lysine or glutamine. Further provided is an isolated, synthetic or recombinant nucleic acid sequence which comprises a codon at rtTA position 37 which differs in at least two nucleotides from an alanine, a lysine or a serine codon and a codon at rtTA position 56 encoding lysine or glutamine.

In embodiments, an isolated, synthetic or recombinant nucleic acid sequence may comprise a codon at rtTA amino acid position 19, 37 and 56. Some embodiments, therefore provide an isolated, synthetic or recombinant nucleic acid sequence, which comprises a codon at rtTA amino acid position 19 which differs in at least two nucleotides from a glutamate codon, a codon at rtTA position 37 which differs in at least two nucleotides from an alanine, a lysine or a serine codon, and a codon at rtTA position 56 encoding lysine or glutamine.

As stated previously, a nucleic acid sequence disclosed herein may comprise an rtTA encoding nucleic acid sequence and/or a sc rtTA encoding nucleic acid sequence, wherein the rtTA encoding nucleic acid sequence and/or single chain rtTA encoding nucleic acid sequence comprises a codon at rtTA amino acid position 9 encoding isoleucine, and/or a codon at rtTA amino acid position 19 encoding alanine, cysteine, aspartate, phenylalanine, histidine, isoleucine, lysine, leucine, methionine, asparagine, glutamine, arginine, serine, threonine, valine, tryptophan or tyrosine, and/or a codon at rtTA amino acid position 37 encoding threonine, histidine, leucine, arginine, cysteine, methionine or glutamine, and/or a codon at rtTA amino acid position 56 encoding lysine or glutamine, and/or a codon at rtTA amino acid position 67 encoding serine, and/or a codon at rtTA amino acid position 68 encoding arginine, and/or a codon at rtTA amino acid position 86 encoding tyrosine, and/or a codon at rtTA amino acid position 138 encoding aspartate or serine, and/or a codon at rtTA amino acid position 157 encoding lysine, and/or a codon at rtTA amino acid position 171 encoding lysine, and/or a codon at rtTA amino acid position 177 encoding leucine, and/or a codon at rtTA amino acid position 195 encoding serine, and/or a codon at rtTA amino acid position 209 encoding threonine. These mutations particularly improve at least one property of an inducible nucleic acid expression system. Hence, either one of these mutations or any combination thereof may present in a nucleic acid sequence in particular embodiments.

Further provided is an isolated, synthetic or recombinant nucleic acid sequence, wherein the rtTA encoding nucleic acid sequence and/or single chain rtTA encoding nucleic acid sequence comprises at least one variant as depicted in FIG. 14.

A nucleic acid sequence disclosed herein may comprise an rtTA encoding nucleic acid sequence and/or a single chain rtTA encoding nucleic acid sequence which comprises at least one mutation as compared to a rtTA or sc rtTA encoding nucleic acid sequence published in (Gossen et al. 1995), (Urlinger et al. 2000) and (Krueger et al. 2003) and/or depicted in FIG. 19.

In another aspect, an isolated, synthetic or recombinant amino acid sequence encoded by a nucleic acid sequence is provided. The amino acid sequence may comprise an rtTA sequence and/or a single chain rtTA sequence, which rtTA sequence and/or single chain rtTA sequence comprises an isoleucine at position 9, and/or an alanine, cysteine, phenylalanine, histidine, isoleucine, lysine, leucine, methionine, asparagine, arginine, serine, threonine, valine, aspartate, glutamine, tryptophan or tyrosine at position 19, and/or a threonine, histidine, leucine, arginine, cysteine, methionine or glutamine at position 37, and/or a lysine or glutamine at position 56, and/or a serine at position 67, and/or an arginine at position 68, and/or a tyrosine at position 86, and/or an aspartate or serine at position 138, and/or a lysine at position 157, and/or a lysine at position 171, and/or a leucine at position 177, and/or a serine at position 195, and/or a threonine at position 209. Each of these mutations particularly confer at least one improved property to an rtTA and/or sc rtTA activator.

As explained above, a nucleic acid sequence and/or an amino acid sequence encoded by a nucleic acid sequence according to embodiments herein is particularly suitable for inducibly expressing a nucleic acid sequence of interest. Use of an isolated, synthetic or recombinant nucleic acid sequence and/or amino acid sequence for inducible expression of a nucleic acid sequence of interest is therefore also herewith provided.

The amino acid sequence may, for example, comprise at least one of the above mentioned mutations.

Further provided is a vector comprising a nucleic acid sequence. Such vector is suitable for a variety of applications. For instance, a vector comprising a therapeutically beneficial nucleic acid sequence is suitable for therapeutic applications. Administration of such vector to an individual in need thereof results in expression of the therapeutic nucleic acid sequence in vivo. Of course, the vector also finds utility in applications involving in vitro expression of a nucleic acid sequence of interest. Methods for constructing a vector with a particular nucleic acid sequence are well known in the art. Non-limiting examples of vectors suitable for generating a vector of the invention are retroviral and lentiviral vectors.

An inducible viral replicon, comprising a nucleic acid sequence according to the invention and at least one viral sequence which is essential for replication under direct or indirect control of the nucleic acid sequence is also herewith provided. As explained herein, a replicon is defined as a nucleic acid molecule capable of replication in a suitable environment, such as a permissive cell, because it has all the necessary elements for replication in such an environment. We call it a replicon, because it will not always be directly derived from the nucleotide sequences of the original pathogen, for instance in the case of single stranded DNA viruses, RNA viruses, etc. Typically, in order to manipulate nucleic acids, double stranded forms are necessary, typically double stranded DNA forms. Therefore, replicons will be double stranded DNA nucleic acids in at least one stage of their life cycle.

A replicon is also intended to reflect that the actual pathogen, or its attenuated live vaccine relative, usually comprises more than just nucleic acid. The nucleic acid is typically packaged into a (viral) particle. Therefore, in certain embodiments, a replicon may also encode a functional packaging signal, allowing for the nucleic acid in its wild-type-like form (RNA in the case of a retrovirus, etc.) to be packed into a viral particle. In order for the replicon to be able to replicate in a host, it is preferred that the replicon also carries the structural genes for the proteins of the envelope and/or capsid, be it in wild-type format or in a somewhat different format (reduced or enhanced target binding, etc.). In order to enhance inducer-dependency of a viral replicon and/or to at least in part prevent loss of inducer-dependency, an inducible viral replicon may thus comprise all viral sequences which are essential for replication under direct or indirect control of the nucleic acid sequence.

A viral replicon may be derived from any virus comprising a stage wherein at least part of its genome is present in the form of DNA, such that the Tet-on machinery is capable of regulating expression of a nucleic acid of interest. Such viruses, for instance, comprise DNA viruses and retroviruses. In one embodiment, at least part of the viral sequences in the inducible replicon is RNA.

In one embodiment, a replicon may be derived from a human immunodeficiency virus. A replicon may be further exemplified by certain embodiments relating to a replicon derived from HIV. However, the invention is also applicable to replicons derived from other pathogens.

Typically, a replicon derived from HIV would be an infectious double stranded DNA clone of an HIV strain. Preferably, the HIV strain is already an attenuated strain, or is made into an attenuated strain by introducing mutations, such as functional deletions, e.g., those described herein. Any repressor/activator elements that are inducible are in principle applicable. In the case of double or more inducible controls, leakage of a single repressor/activator becomes less important, although essentially no leakage is still highly preferred. As a safety valve, it would be advantageous to provide the replicon with a suicide gene that can be activated when unwanted effects occur, such as replication beyond what is necessary for an immune response or rescue by wild type virus, etc. Such a suicide gene is e.g., HSV-tk, which can be induced by adding gancyclovir or a functional equivalent thereof. Upon induction, such a suicide gene will kill the infected cell and thereby inhibit further replication and infection of other cells. Thus, in some embodiments a replicon is provided which further comprises a suicide gene.

In order to attenuate an HIV replicon and/or the resulting virus the replicon may be provided with a functional deletion of the TAR-element. Thus, in yet another embodiment, the invention provides a replicon, which further comprises an inactivated TAR element.

In order to attenuate an HIV replicon it may be preferred to functionally delete the Tat element. Thus, some embodiments also provide a replicon, which further comprises an inactivated Tat element. Both elements mentioned above may be functionally deleted. Functional deletion means that at least their function in the replication of the replicon is at least partially inhibited. Essential genes for replication typically should not be completely dysfunctional.

Proteins necessary for removing repression or initiating activation elements which are present upstream of the essential genes to be put under control may be encoded by a replicon and are preferably inserted in a non-essential gene. Thus, in certain embodiments, a replicon is provided wherein at least one functional part of the inducible repressor and/or activator, preferably an rtTA and/or sc rtTA nucleic acid sequence, is inserted into the nef gene. The functional part in this case of course refers to any proteinaceous substance capable of activating the element in control of the essential gene. Space may be created for the sequence encoding the proteinaceous substance. Thus, some embodiments also provide a replicon in which at least part of the nef gene is deleted to create space for insertion.

To further attenuate a replicon, further elements of the wild-type virus can be functionally deleted. Thus, some embodiments further provide a replicon in which at least one NF-kB element has been deleted. In certain embodiments, the motif to be activated is a tetO motif, preferably present in an LTR. Thus, some embodiments also provide a replicon, which comprises at least one tetO motif in at least one functional LTR.

It may be advantageous to have more than one element before an essential gene. Thus, some embodiments also provide a replicon which comprises at least 2, 4, 6, or 8 such elements in at least one functional LTR.

At least one LTR may be modified in order to at least in part avoid reversion to wild type virus.

Some aspects of the invention further provide methods using the replicons to produce dependent viruses, meaning viruses needing an inducing agent in order to be able to replicate. Thus, certain embodiments provide a method for producing a virus dependent on an inducing agent for replication, comprising providing a permissive cell with a replicon, culturing the cell in the presence of the inducing agent and harvesting the dependent virus from the culture. Again such methods are preferably applied to HIV. Thus, embodiments provide a method in which the dependent virus is a human immunodeficiency virus, preferably an attenuated virus.

In one embodiment, the inducing agent is doxycyclin or a functional analog thereof. In another embodiment, however, the inducing agent comprises an antibiotic other than doxycyclin, e.g., tetracyclin and/or minocyclin. As stated previously, if tetracyclin and/or minocyclin-dependency is desired, a replicon may be utilized which comprises an rtTA and/or sc rtTA encoding nucleic acid sequence comprising a mutation or a combination of mutations as depicted in FIG. 15, except for the wild type rtTA and the F86Y A209T variant.

More typically, a replicon comprising mutations F67S V9I G138D F86Y A209T, C68R V9I G138D F86Y A209T, G19M V9I G138D F86Y A209T, E37Q V9I G138D F86Y A209T, G19M F67S V9I G138D F86Y A209T, S12G F67S V9I G138D F86Y A209T and/or C68R F67S V9I G138D F86Y A209T may be used for tetracycline-inducible expression of a nucleic acid sequence of interest since these replicons are particularly sensitive for tetracycline, meaning that a small amount of tetracycline is sufficient for inducing gene expression. In some embodiments, a replicon comprising mutation F67S V9I G138D F86Y A209T, C68R V9I G138D F86Y A209T and/or S12G F67S V9I G138D F86Y A209T may be used for tetracycline-inducible expression of a nucleic acid sequence of interest, since these replicons are very sensitive for tetracycline and show low background activity in the absence of effector.

In a further embodiment, a replicon comprising mutations V9I G138D F86Y A209T, F67S V9I G138D F86Y A209T, F67S V9I E157K F86Y A209T, F67S V9I R171K F86Y A209T, F67S E37Q F86Y A209T, C68R V9I G138D F86Y A209T, G19M V9I G138D F86Y A209T, E37Q V9I G138D F86Y A209T, G19M F67S V9I G138D F86Y A209T, S12G F67S V9I G138D F86Y A209T and/or C68R F67S V9I G138D F86Y A209T may be used for minocycline-inducible expression of a nucleic acid sequence of interest since these replicons are particularly sensitive for minocycline, meaning that a small amount of minocycline is sufficient for inducing gene expression. In certain embodiments, a replicon comprising mutations F67S V9I G138D F86Y A209T, F67S E37Q F86Y A209T, C68R V9I G138D F86Y A209T and/or S12G F67S V9I G138D F86Y A209T may be used for minocycline-inducible expression of a nucleic acid sequence of interest since these replicons are very sensitive for minocycline and show low background activity in the absence of effector.

In another aspect of the invention, viruses produced by methods disclosed herein, or which can be produced by the methods disclosed herein, are provided. Thus, some embodiments also provide a virus dependent on an inducing agent for replication obtainable by a method as disclosed herein, such as a human immunodeficiency virus, typically attenuated. Suitable methods for producing a replicon and/or virus are known in the art. For instance, non-limiting examples of methods for producing an inducible viral replicon derived from HIV, comprising an rtTA sequence and TetO elements, and uses thereof, are described in WO01/20013 page 9, line 13 to page 18, line 27. These methods and uses are incorporated herein by reference.

A replicon and/or virus according to certain embodiments disclosed herein may be particularly suitable for immunization and vaccination. In certain embodiments, administration of a replicon and/or virus to an individual allows for controlled replication of the replicon and/or virus within the individual, resulting in an immune response in the individual. The extent of replication of the replicon or virus and, as a result, the extent of elicited immune response is controlled by regulating the presence and/or amount of inducer. In one embodiment, an immune response is elicited in an individual in order to provide the individual with at least partial protection against infection by the kind of virus from which the replicon or virus of the invention is derived. In another embodiment, an immune response is elicited in a non-human animal in order to produce a binding compound (such as for instance antibodies and/or T cells) and/or a cell capable of producing such binding compound (such as a B cell). The antibodies, T cells and/or B cells, or a functional part and/or a nucleic acid thereof, may be harvested for further use, for instance for the production of monoclonal antibodies.

Of course, various alternative methods and applications involving immunization and/or vaccination are known in the art. The use of a replicon and/or virus in such methods and applications is also within the scope hereof.

Some aspects of the invention provide an immunogenic composition comprising a replicon and/or a virus. An immunogenic composition comprising a nucleic acid sequence is also provided. An immunogenic composition may typically comprise a suitable adjuvant and/or carrier. Adjuvants and carriers are well known in the art. For instance, an Aluminum Salt Adjuvant and/or a saline solution may be used.

In one embodiment, an immunogenic composition further comprises an amount of inducing agent. This is, however, not necessary: an inducing agent can be administered at any time. In some embodiments, an immunogenic composition comprises a vaccine capable of eliciting full protection against the kind of virus from which the replicon or virus is derived. This means that subsequent infection with the kind of virus from which the replicon or virus is derived does essentially not result in disease.

An immunogenic composition or a vaccine may comprise a single dosage unit, but it may also comprise at least one inducing agent separately, or it may be made on the spot from a replicon and/or virus that are reconstituted with a liquid excipient such as saline, optionally together with an adjuvant and/or an inducing agent. Viral vaccines are well known in the field. General rules of thumb applicable to known vaccines will also apply to immunogenic compositions and vaccines hereof. Suitable doses may be determined through the normal dose finding studies performed during (pre)clinical trials, e.g., by simple titration of the amount of doxycycline as inducing agent. An immunogenic composition or vaccine may be sufficient on its own, but it may also be used in addition to other therapeutic and/or prophylactic compounds. The inducing agent may be needed over a longer period of time and can be provided separately.

An immunogenic composition and/or vaccine is one for at least partial prophylaxis of infection with a human immunodeficiency virus.

Some embodiments also provide a use for an immunogenic composition and/or vaccine in that they provide methods for at least partial prophylaxis and/or treatment of AIDS, comprising administering an immunogenic composition and/or vaccine as disclosed herein to an individual and allowing for viral replication for a limited time by providing the inducing agent. Booster vaccinations are possible, preferably by simple readdition of such an inducing agent at later times.

Some embodiments also provide a method for the controlled replication of a virus or a viral replicon comprising providing a permissive cell with a replicon or a virus as disclosed herein, culturing the cell in the presence of the inducing agent and manipulating the amount of inducing agent present.

As explained herein, a replicon, virus and/or nucleic acid sequence may be suitable for eliciting an immune response against a virus of interest. Such an immune response is capable of at least in part preventing subsequent infection, replication and/or spreading by the virus of interest. Moreover, an immune response of an individual that is already suffering from an infection by the virus of interest may be enhanced by a replicon, virus and/or nucleic acid sequence as disclosed herein, resulting in an improved counteraction to disease.

Replicons, viruses and nucleic acid sequences may thus be suitable for use as a medicament and/or vaccine. A replicon or virus for use as a medicament and/or vaccine is therefore herewith provided, as well as an isolated or recombinant nucleic acid sequence for use as a medicament and/or vaccine. It is possible to place at least one HIV sequence essential for replication under direct or indirect control of an rtTA and/or sc rtTA nucleic acid as disclosed herein. This way, controlled replication of HIV has become possible, allowing for at least partial prophylaxis and/or treatment of AIDS. A use of an isolated or recombinant replicon, virus and/or nucleic acid sequence as disclosed herein for the preparation of a medicament or immunogenic composition for at least in part preventing and/or treating AIDS is therefore also herewith provided.

One further embodiment provides an isolated cell comprising a nucleic acid sequence, a replicon and/or a virus as disclosed herein.

The invention is further explained in the following examples. These examples do not limit the scope of the invention, but merely serve to clarify the invention.

EXAMPLES

Example 1

We have previously reported on the construction of an infectious HIV-rtTA virus that is critically dependent on dox for replication (Verhoef et al. 2001; Das et al. 2004b; Marzio et al. 2001). In this virus, the natural transcriptional activator Tat and its TAR binding site were inactivated by mutation and functionally replaced by the components of the Tet-on system (FIG. 1A). The gene encoding the transcriptional activator rtTA was inserted in place of the nef gene, and the tetO DNA binding sites were introduced in the viral LTR promoter. This virus does not replicate in the absence of dox. Upon dox administration, rtTA activates transcription from the LTR-tetO promoter, resulting in expression of the viral proteins and viral replication. Subsequently, a variant has been provided that has acquired two amino acid changes in the rtTA protein: the phenylalanine at position 86 was replaced by tyrosine (F86Y) and the alanine at position 209 by threonine (A209T) (Das et al. 2004a).

We started multiple, independent virus cultures of the HIV-rtTA$_{F86Y\ A209T}$ variant, which contains both the optimized LTR-tetO promoter configuration and the improved rtTA gene. After culturing the virus with dox for up to 200 days, the rtTA gene was sequenced. The F86Y and A209T mutations were stably maintained in all analyzed cultures. Several viruses from independent cultures had acquired additional mutations in the rtTA gene. A virus variant should have a replication advantage to become the dominant sequence in a virus population. Mutations in rtTA may improve rtTA function, and thus enhance viral replication. To increase the chance of identifying such beneficial mutations, we focused on the rtTA mutations that were observed in multiple cultures (FIG. 1A and Table 1). All these amino acid substitutions are located in the TetR part of rtTA: V9I is in the α1 helix within the DNA-binding domain, F67S is in the loop following α4, and G138D, E157K, and R171K are within the α8-α9 region of the regulatory core domain (FIG. 1B). V9I was found both as an individual mutation and in combination with G138D, E157K, or R171K. A combination of F67S and R171K was also observed. There are seven natural variants of TetR (A-E, G, H) and rtTA is based on class B (TetR$^{B}$). Interestingly, only TetR$^{B}$ has a Phe at position 67, whereas most TetRs have a Ser at this position (Table 1). Other amino acid substitutions observed in the evolved rtTAs are never naturally present in TetR variants.

Characterization of the Evolved rtTA Variants. To test whether the evolved rtTAs exhibit improved transcriptional activity, we assayed rtTA activity in a regular Tet system. Expression plasmids encoding the original (wild-type, this is the rtTA2$^{S}$-S2 variant described in Urlinger et al. 2000) and mutant rtTA proteins (V1-V10, Table 1) were constructed and transfected into C33A cells with a plasmid expressing luciferase reporter under the control of the viral LTR-2ΔtetO promoter. The luciferase level measured two days after transfection reflects rtTA activity (FIG. 2A). Wild-type and all mutant rtTAs show no activity in the absence of dox. Wild-type rtTA activity is detectable first at 500 ng/ml dox and increases further at 1000 ng/ml. rtTA V1 (F86Y A209T) activity is already detectable at 50 ng/ml dox and gradually increases with higher dox concentrations. At 1000 ng/ml dox, the V1 variant is 2.5-fold more active than the wild-type. All mutants did evolve from rtTA V1, and their activity should thus be compared with this variant. rtTA V2 is more active than V1 at the lowest dox concentration tested, but less active at high dox levels. The other rtTAs with a single amino acid substitution (V3-V6) are more active than V1 both at low and high dox levels. The variants V7, V8, and V9 combine the V2 mutation with the V4, V5, and V6 mutation, respectively. These combinations further improve rtTA activity both at low and high dox levels. The V10 variant, which combines the V3 and V6 mutations, is the most active rtTA of the naturally evolved variants. Therefore, the viral evolution strategy resulted in several novel rtTA variants with enhanced transcriptional activity and dox-sensitivity compared with wild-type rtTA and the V1 variant that was used to start the evolution experiment.

To test whether this rtTA optimization reflects a specific adaptation to the viral LTR-2ΔtetO promoter, we assayed rtTA activity with a reporter gene construct in which luciferase expression is under the control of a minimal CMV promoter coupled to an array of seven tetO elements [4]. All evolved rtTA variants demonstrate improved activity with this promoter construct (FIG. 2B), which mimics the result with the LTR-2ΔtetO construct (FIG. 2A). Thus, the observed mutations in rtTA are not virus-specific adaptations, but are general improvements of the Tet-on system. We also assayed rtTA activity in HeLa X1/6 cells [9] that contain chromosomally integrated copies of the CMV-7tetO luciferase reporter construct (FIG. 2C). In these cells, the evolved rtTAs show a similar pattern of activity as with episomal reporter gene constructs in C33A cells. Thus, these mutations improve rtTA activity independent of the type of promoter and the episomal or chromosomal status of the target gene.

To compare the dox-sensitivity of the rtTA variants in another way, we calculated the dox concentration that each rtTA variant needs to reach an activity similar to that of the wild-type rtTA at 1000 ng/ml dox (FIG. 3). The V10 variant needs only 44 ng/ml dox to reach this activity level, which reflects a 23-fold higher dox-sensitivity than the wild-type rtTA. This makes the V10 variant the most dox-sensitive and most active rtTA (6.6-fold more active than the wild-type, FIG. 3) of the naturally evolved variants.

Combining the Beneficial Mutations Further Improves rtTA Activity.

Analysis of the evolved rtTA variants revealed that the double mutants exhibit a higher activity and dox-sensitivity than the single mutants. For instance, V6 (R171K) is 4.4-fold more sensitive than the wild-type rtTA, and the double mutant V9 (V9I R171K) is 14.9-fold more dox-sensitive. We therefore constructed additional rtTA variants in which the observed mutations were combined (V11-V18, Table 1), and assayed their activity (FIG. 2D). As shown in FIG. 3, all combination variants demonstrate a higher transcriptional activity and dox-sensitivity than the naturally evolved variants. The triple mutants V14, V15, and V16 are the most active and most dox-sensitive rtTAs. When compared with wild-type rtTA, these triple mutants are 7-fold more active at high dox levels and 100-fold more sensitive to dox. The V15 and V16 variants do not show any basal activity without dox, whereas we frequently observed a low, but distinct basal activity with the V14 variant (less than 0.1% of the induced level).

A more extensive list of novel rtTA variants that carry mutations observed in HIV-rtTA evolution and that demonstrate improved transcriptional activity and dox-sensitivity is shown in FIG. 14B.

To exclude the possibility that the enhanced activity observed for the mutant rtTAs resulted from an increased protein level, we determined the intracellular steady state level of the rtTA proteins. Lysates of HeLa X1/6 cells transfected with rtTA expression plasmids were subjected to SDS-PAGE followed by Western blot analysis with polyclonal anti-TetR antibodies. An equal amount of rtTA protein was detected for all naturally evolved and constructed variants (FIG. 4, and data not shown). These results indicate that the enhanced activity and dox-sensitivity are intrinsic properties of the mutant rtTA proteins and do not result from increased expression or protein stability.

Novel rtTA Variants can be Activated by Dox-Like Compounds.

Dox is the most efficient effector that controls the Tet-on system. Other dox-like compounds, such as tetracycline (Tc) and minocycline (Mc), do not effectively activate the wild-type rtTA and the original HIV-rtTA virus. To test if the novel rtTA variants with improved activity and dox-sensitivity have a broader effector-specificity, we assayed the activity of a subset of these rtTA variants at different Tc and Mc concentrations (FIG. 5). Whereas the wild-type rtTA and the VI variant are not activated by Tc and Mc, mutant V3 shows a low level of activity at a high concentration of Tc or Mc (10000 ng/ml). V7 activity is already detectable at 1000 ng/ml Tc or Mc, and this activity increases at higher effector levels. V14, which combines the V3 and V7 mutations, shows the highest activity with Tc and Mc. The activity at 10000 ng/ml Tc is similar to that of the wild-type rtTA at 1000 ng/ml dox. At 1000 ng/ml Mc, V14 is even more active than the wild-type rtTA at 1000 ng/ml dox. Thus, we have generated rtTA variants with a broadened effector-specificity. A more extensive list of novel rtTA variants that are responsive to Tc and/or Mc is shown in FIG. 15.

rtTA Variants Improve HIV-rtTA Replication.

To test if the rtTA variants with enhanced activity and dox-sensitivity can also improve HIV-rtTA replication, we constructed viral variants with the rtTA genes encoding either mutant V7 or V14, and assayed their replication in SupT1 cells at different dox concentrations (FIG. 6). The original HIV-rtTA-$_{V1}$, (HIV-rtTA$_{-F86YA209T}$) was included as a control. This control HIV-rtTA$_{-V1}$ does not replicate in the absence of dox or at low dox levels, efficient replication was observed at 100 ng/ml dox, and the replication rate further increased at 1000 ng/ml dox. The replication of HIV-rtTA$_{-V7}$ and HIV-rtTA$_{-V14}$ was also completely dependent on dox. The HIV-rtTA$_{-V7}$ showed a low level of replication at 1 ng/ml dox and efficient replication at 10 ng/ml. For HIV-rtTA$_{-V14}$, a high level of replication was already apparent at 1 ng/ml dox. These results demonstrate that the variants V7 and V14 significantly improve HIV-rtTA replication at low dox concentrations. Importantly, like the original HIV-rtTA, these viruses do not replicate in the absence of dox. Apparently, the low basal rtTA-activity observed with the V14 variant in the absence of dox is not sufficient to support viral replication.

We also assayed replication of these new HIV-rtTA variants in the presence of Tc and Mc (FIG. 7). Whereas the control HIV-rtTA$_{-V1}$ did not replicate in the presence of 500 ng/ml Tc or Mc, both HIV-rtTA$_{-V7}$ and HIV-rtTA$_{-V14}$ show efficient replication with these effectors. These results confirm that the rtTA variants V7 and V14 can be effectively activated by Tc and Mc.

Conclusion

Amino acid substitutions in rtTA at position 9, 19, 37, 67, 68, 86, 138, 157, 171, 177, 195 and/or 209, which are observed during evolution of the HIV-rtTA virus, enhance the transcriptional activity and/or inducer-sensitivity of rtTA. Moreover, these mutations broaden the inducer-specificity of rtTA. The most optimal rtTA variants (V15 and V16) are 7-fold more active at high dox levels and 100-fold more sensitive to dox than the original rtTA. Importantly, these rtTA variants do not show any basal activity in the absence of dox. High activity and dox-sensitivity of these novel rtTAs significantly improve the performance of the Tet-on system.

Materials and Methods

Cell cultures. The human T-lymphocyte cell line SupT1 (Smith et al. 1984) was cultured in RPMI 1640 medium supplemented with 10% fetal calf serum (FCS), penicillin (100 U/ml), and streptomycin (100 U/ml). HeLa X1/6 (Baron et al. 1997) is a HeLa-derived cervix carcinoma cell line, containing chromosomally integrated copies of the CMV-7tetO promoter/luciferase reporter construct pUHC13-3 (Gossen et al. 1992). HeLa X1/6 and C33A cervix carcinoma cells (ATCC HTB31) (Auersperg, 1964) were grown in Dulbecco's modified Eagle's medium supplemented with 10% FCS, minimal essential medium nonessential amino acids, penicillin (100 U/ml), and streptomycin (100 U/ml). All cell cultures were kept at 37° C. and 5% $CO_2$.

Virus replication. Construction of the HIV-rtTA molecular clone was described previously (Verhoef et al. 2001; Das et al. 2004b). The HIV-rtTA variant used in this study contains the 2ΔtetO configuration (Marzio et al. 2001; Marzio et al.

2002) in both the 5' and the 3' LTR. SupT1 cells ($5\times10^6$) were transfected with 5 μg of the HIV-rtTA molecular clone by electroporation (250 V and 975 μF). Viral replication was induced with doxycycline (dox, D-9891, Sigma, St. Louis, Mo., USA), tetracycline (Tc, Sigma T-3383) or minocycline (Mc, Sigma M-9511). The CA-p24 level in the cell-free culture supernatant was determined by antigen capture enzyme-linked immunosorbent assay (ELISA) (Back et al. 1996).

For the selection of evolved viruses, SupT1 cells were transfected with the HIV-rtTA$_{-F86Y\ A209T}$ molecular clone (Das et al. 2004a), and cultured in the presence of 1 μg/ml dox for up to 200 days. The virus containing culture supernatant was passaged onto fresh SupT1 cells at the peak of infection, as determined by the massive appearance of syncytia. At regular intervals, cell and supernatant samples were taken from the culture and stored at −80° C. for subsequent analysis.

Proviral DNA analysis and cloning of evolved sequences. Total cellular DNA from infected cells was isolated as described previously (Das et al. 1997). The proviral rtTA genes were PCR amplified with the sense primer tTA1 (5'-ACAGCCATAGCAGTAGCTGAG-3') (SEQ ID NO:1) and the antisense primer tTA-rev2 (5'-GATCAAGGATATCTTGTCTTCGT-3') (SEQ ID NO:2), and sequenced with the bigdye terminator cycle sequencing kit (Applied Biosystems, Foster city, CA, USA). The PCR products were digested with XbaI and SmaI and used to replace the corresponding fragment in pCMV-rtTA, in which the expression of wild-type rtTA (rtTA2$^S$-S2, (Urlinger et al. 2000)) is controlled by the human cytomegalovirus (CMV) immediate-early promoter. Mutant rtTA genes were cloned from pCMV-rtTA into the shuttle vector pBlue3'LTRext-deltaU3-rtTA$_{F86Y\ A209T}$-2ΔtetO (Das et al. 2004a) using the XcmI and NdeI sites and subsequently cloned back into the HIV-rtTA molecular clone as BamHI-BglI fragments. To introduce the F67S and G138D mutations into evolved rtTA variants, mutagenesis PCR (Mikaelian et al. 1992) was performed with the corresponding pCMV-rtTA plasmid and the mutagenic primer (primer M) tTA-F67S (5'-CATACCCACTCCTGCCCCCTGGAAGGCGA-3', mismatching nucleotide underlined) (SEQ ID NO:3) or tTA-G138D (5'-GTCCGCCGTGGACCACTTTACACTGGGCT-3') (SEQ ID NO:4) and the general primers 5'-TGGAGACGCCATCCACGCT-3' (primer 1) (SEQ ID NO:5), 5'-TGAAATCGAGTTTCTCCAGGCCACATATGA-3' (primer 2) (SEQ ID NO:6), and 5'-TCACTGCATTCTAGTTGTGGT-3' (primer 3) (SEQ ID NO:7). Briefly, PCR reactions were performed with primer M plus primer 3, and with primer 1 plus primer 2. The PCR products were purified, mixed, and PCR amplified with primers 1 and 3 (see reference (Mikaelian et al. 1992) for details). The resulting mutated rtTA genes were cloned as EcoRI-BamHI fragments into pCMV-rtTA. All constructs were verified by sequence analysis.

rtTA activity assay. Two firefly luciferase reporter constructs with different promoter configurations were used. pLTR-2ΔtetO-luc contains the LTR-2ΔtetO promoter derived from the HIV-rtTA molecular clone (Marzio et al. 2001; Marzio et al. 2002). pCMV-7tetO-luc, previously named pUHC13-3 (Gossen et al. 1992), contains seven tetO elements located upstream of a minimal CMV promoter. The plasmid pRL-CMV (PROMEGA®, Madison, Wis., USA), in which the expression of Renilla luciferase is controlled by the CMV promoter, was used as an internal control to allow correction for differences in transfection efficiency.

C33A and HeLa X1/6 cells were grown in 2-cm$^2$ wells to 60% confluency and transfected by the calcium phosphate precipitation method (Das et al. 1999). C33A cells were transfected with 0.4 ng pCMV-rtTA (wild-type or mutant), 20 ng pLTR-2ΔtetO-luc or pCMV-7tetO-luc, 0.5 ng pRL-CMV, and 980 ng pBluescript as carrier DNA. HeLa X1/6 cells were transfected with 8 ng pCMV-rtTA, 2.5 ng pRL-CMV, and 990 ng pBluescript. The amount of the DNA constructs was optimized for each cell type to keep rtTA-mediated transactivation within the linear range and to avoid squelching of transcription factors. Cells were cultured for 48 hours in the presence of different concentrations of dox, Tc or Mc, and lysed in Passive Lysis Buffer (PROMEGA®). Firefly and Renilla luciferase activities were determined with the dual-luciferase reporter assay (PROMEGA®). The activity of the rtTA variants was calculated as the ratio of the firefly and Renilla luciferase activities, and corrected for between-session variation.

Western blot analysis. HeLa X1/6 cells were transfected at 90% confluency with 1 μg of wild-type or mutant pCMV-rtTA and 2 μl of Lipofectamine 2000 (Invitrogen, Carlsbad, Calif., USA) in 2-cm$^2$ wells. Cells were cultured for 48 hours and lysed in 100 μl of Passive Lysis Buffer. 10 μl of the lysate was subjected to SDS-polyacrylamide gel separation, and transferred to Immobilon-P membrane (Millipore, Billerica, Mass., USA). For immunochemical detection of rtTA variants, membranes were incubated with rabbit serum containing polyclonal anti-TetR antibodies (Krueger et al. 2003). Bound antibodies were visualized with peroxidase-linked anti-rabbit IgG and the ECL+ kit (Amersham Biosciences, Freiburg, Germany) and analyzed with a Storm 860 Imager (Amersham Biosciences).

Example 2

HIV-1 vaccines based on a live-attenuated virus have shown promise in the SIV-macaque model, but are generally considered unsafe for use in humans. The major safety concern is that chronic low-level replication of the attenuated virus may eventually lead to selection of fitter and more pathogenic virus variants. Ideally, one would like to restrict replication of a vaccine virus to the time window that is needed to elicit a protective immune response. We previously presented a novel vaccine approach that uses a conditional-live HIV-1 virus. In this HIV-rtTA virus, the viral transcriptional activator Tat and its TAR binding site were inactivated by mutation and functionally replaced by the components of the Tet-on system. This system, in which gene expression is stringently controlled by the non-toxic effector doxycycline (dox), is widely applied to regulate gene expression in eukaryotes. The rtTA gene encoding the transcriptional activator was inserted in place of the nef gene, and the tet-operator (tetO) DNA binding sites were placed in the viral LTR promoter. This HIV-rtTA virus does not replicate in the absence of dox. Binding of dox to rtTA triggers a conformational change that allows the protein to bind tetO DNA, resulting in transcriptional activation and subsequent viral replication. Upon vaccination with this virus, replication can be temporarily activated and controlled to the extent needed for induction of the immune system by transient dox administration.

The potential use of this dox-dependent HIV-rtTA virus as a vaccine raises new safety questions concerning the genetic stability of the introduced Tet-on system. There are several hypothetical evolutionary routes toward a constitutively replicating virus. First, the virus may restore the function of the Tat-TAR system, despite the multiple inactivating mutations that were introduced in both elements to avoid simple reversion to the wild-type sequence. In this scenario, the dox-controlled rtTA-tetO system will become superfluous, and may be inactivated over time by mutation or deletion. Second, the viral LTR promoter could become a constitutive transcription element, for instance by acquisition of a binding site for a constitutively expressed cellular transcription factor. Replication of such a virus is not dependent on a virally encoded transactivator, neither Tat nor rtTA. Third, the introduced rtTA-tetO axis may lose dox-dependence, thereby creating an uncontrolled Tet system. This scenario would for instance occur through acquired mutations in the rtTA protein that shift its conformation into the DNA-binding mode, even in the absence of dox.

To address these safety issues, we followed the evolution of HIV-rtTA in multiple, independent virus cultures. We observed loss of dox-control in several cultures, which in all cases resulted from a typical amino acid substitution either at position 19 or 37 in the rtTA protein. We developed novel rtTA variants with alternative amino acids at these positions, and demonstrated that the corresponding HIV-rtTA variants did not lose dox-control in long-term cultures. Thus, we improved the genetic stability of the Tet-on system and the HIV-rtTA vaccine candidate by blocking unwanted evolutionary routes.

Materials and Methods

Virus cultures. The HIV-rtTA infectious molecular clone is a derivative of the HIV-1 LAI proviral plasmid (Peden et al. 1991) and was described previously (Das et al. 2004b; Verhoef et al. 2001). HIV-rtTA used in this study is the KYK version, which contains the inactivating Y26A mutation in the Tat gene and five nucleotide substitutions in the TAR hairpin motif. This virus contains the rtTA2$^{2}$-S2 gene (Urlinger et al. 2000) in place of the nef gene and eight tetO sequences in the LTR promoter region. The HIV-rtTA2ΔtetO clone is identical to HIV-rtTA, but with the optimized 2ΔtetO promoter configuration (Marzio et al. 2001; Marzio et al. 2002). HIV-rtTA$_{F86Y\ A209T}$ contains the LTR-2ΔtetO promoter and the recently described rtTA$_{F86Y\ A209T}$ gene (Das et al. 2004a).

SupT1 T cells were grown at 37° C. and 5% $CO_2$ in RPMI1640 medium containing 10% fetal bovine serum (FBS), 100 units/ml penicillin, and 100 μg/ml streptomycin. SupT1 cells were transfected with HIV-rtTA molecular clones by electroporation. Briefly, $5\times10^6$ cells were washed in RPMI1640 with 20% FBS and mixed with 5 μg of DNA in 250 μl RPMI1640 with 20% FBS. Cells were electroporated in 0.4-cm cuvettes at 250 V and 975 μF and subsequently resuspended in RPMI1640 with 10% FBS. The CA-p24 level in the cell-free culture supernatant was determined by antigen capture enzyme-linked immunosorbent assay (ELISA) (Back et al. 1996).

The 24-well evolution experiment was started with transfection of 40 μg of the HIV-rtTA proviral plasmid into $2\times10^7$ SupT1 cells. Cells were split into 24 independent cultures and maintained in the presence of 1 μg/ml dox (Sigma D-9891) for up to 200 days. The virus containing culture supernatant was passaged onto fresh SupT1 cells at the peak of infection, as determined by the massive appearance of syncytia. At regular intervals, supernatant samples were taken from the culture and tested in parallel infections with and without dox. Cell samples were stored at −80° C. for subsequent analysis.

Proviral DNA Analysis and Cloning of Evolved Sequences

HIV-rtTA infected cells were pelleted by centrifugation and washed with phosphate-buffered saline. DNA was solubilized by resuspending the cells in 10 mM Tris-HCl (pH 8.0)-1 mM EDTA-0.5% Tween 20, followed by incubation with 200 μg/ml of proteinase K at 56° C. for 60 mM and 95° C. for 10 min. Proviral DNA sequences were PCR amplified from total cellular DNA. The first exon of the Tat gene was amplified with the primers KV1 (5'-CCATCGATACCGTCGACATAGCAGAATAGG-3') (SEQ ID NO:8) and 3'TAT (5'-CGGGAATTCTTACTGCTTTGATAGAGAAAC-3') (SEQ ID NO:9). The LTR-tetO region was amplified with the primers tTA-tetO1 (5'-CTCCCCGGGTAACTAAGTAAGGAT-3') (SEQ ID NO:10) and C(N1) (5'-GGTCTGAGGGATCTCTAGTTACCAGAGTC-3') (SEQ ID NO:11). The rtTA gene was amplified with the primers tTA1 (5'-ACAGCCATAGCAGTAGCTGAG-3') (SEQ ID NO:1) and tTA-rev2 (5'-GATCAAGGATATCTTGTCTTCGT-3') (SEQ ID NO:2). All PCR fragments were sequenced with the bigdye terminator cycle sequencing kit (Applied Biosystems). For the cloning of the G19E or E37K mutated rtTA sequences into the HIV-rtTA provirus, rtTA PCR fragments were digested with XcmI and SmaI and cloned into the corresponding sites of the shuttle vector pBlue31TRext-deltaU3-rtTA-2ΔtetO (16). The BamHI-BglI fragment of the shuttle vector was used to replace the corresponding sequence in HIV-rtTA 2ΔtetO.

Construction of Novel HIV-rtTA Variants and rtTA Expression Plasmids.

HIV-rtTA variants with an alternative G codon. (GGU instead of GGA) at rtTA position 19 and with a wild-type (E) or alternative amino acid (D, F, L, N, Q, R, S) at position 37 were constructed by oligonucleotide directed mutagenesis. The oligonucleotide G19 (5'-ATAACCATGTCTAGACTGGACAAGAGCAAAGTCATAAACTCTGCTCTGGAATTACTCAATGGTGTCGGTATCGAAGGCCTGACGACAAGGAAACTCGCT-3', mutated nucleotide underlined) (SEQ ID NO:12) was annealed to the oligonucleotide rev-37 (5'-AGCAGGGCCCGCTTGTTCTTCACGTGCCAGTACAGGGTAGGCTGXXXAACTCCCAGCTTTTGAGCGAGTTTCCTTGTCGTCAGGCCTTCGA-3', with XXX corresponding to amino acid 37; this triplet is CTC for E, ATC for D, GAA for F, AAG for L, ATT for N, CTG for Q, GCG for R, and AGA for S) (SEQ ID NO:13), both strands were completed with Klenow DNA polymerase in the presence of dNTPs, digested with XcmI and ApaI, and ligated into the similarly digested shuttle vector pBlue3'LTRext-deltaU3-rtTA$_{F86Y\ A209T}$-2ΔtetO (Das et al. 2004a). The BamHI-BglI fragment of the shuttle vector was used to replace the corresponding sequence in HIV-rtTA 2ΔtetO.

The plasmid pCMV-rtTA contains the rtTA2$^{S}$-S2 gene in the expression vector pUHD141-1/X (Urlinger et al. 2000). To generate rtTA variants with different amino acids at position 19 or 37, PCR was performed on pCMV-rtTA with the sense primer random-rtTA-19 (5'-TTCACCATGTCTAGACTGGACAAGAGCAAAGTCATAAACTCTGCTCTGGAATTACTCAATNNKGTCGGTATCGAAGGCCTGACGA-3', mutated nucleotide underlined with K corresponding to T or G, and N corresponding to T, C, A or G) (SEQ ID NO:14) plus the antisense primer CMV2 (5'-TCACTGCATTCTAGTTGTGGT-3') (SEQ ID NO:15) or with the sense primer CMV1 (5'-TGGAGACGCCATCCACGCT-3') (SEQ ID NO:16) plus the antisense primer random-rtTA-37 (5'-AGCAGGGCCCGCTTGTTCTTCACGTGCCAGTACAGGGTAGGCTGMNNAACTCCCAGCTTTTGAGCGA-3', mutated nucleotide underlined with M corresponding to A or C, and N corresponding to T, C, A or G), respectively (SEQ ID NO:17). The mutated rtTA sequences were cloned as XbaI-ApaI fragments into pCMV-rtTA$_{F86Y\ A209T}$ (Das et al. 2004a). All constructs were verified by sequence analysis. To combine the G19F (UUU codon) and E37L (CUU codon) mutations, the E37L-containing StuI-BamHI fragment of pCMV-rtTA$_{E37L}$ was used to replace the corresponding sequence in pCMV-rtTA$_{G19F}$, resulting in pCMV-rtTA$_{G19F\ E37L}$. The rtTA$_{G19F\ E37L}$ sequence was cloned into the shuttle vector pBlue3'TRext-deltaU3-rtTA$_{F86Y\ A209}$-2AtetO (Das et al. 2004a) using the XcmI and NdeI sites and subsequently cloned into the HIV-rtTA 2ΔtetO molecular clone as a BamHI-BglI fragment.

rtTA Activity Assay.

HeLa X1/6 cells (Baron et al. 1997) are derived from the HeLa cervix carcinoma cell line and harbor chromosomally integrated copies of the CMV-7tetO firefly luciferase reporter construct pUHC13-3 (Gossen et al. 1992). Cells were grown at 37° C. and 5% $CO_2$ as a monolayer in Dulbecco's modified Eagle's medium supplemented with 10% FBS, minimal essential medium nonessential amino acids, 100 units/ml penicillin, and 100 μg/ml streptomycin.

HeLa X1/6 cells were grown in 2-cm$^2$ wells to 60% confluency and transfected by the calcium phosphate precipitation method. 1 μg of DNA mixture in 15 μl water was mixed with 25 μl of 50 mM HEPES (pH 7.1)-250 mM NaCl-1.5 mM $Na_2HPO_4$ and 10 μl of 0.6 M $CaCl_2$, incubated at room temperature for 20 min and added to the culture medium. The DNA mixture consisted of 8 ng pCMV-rtTA, 2.5 ng pRL-CMV, and 990 ng pBluescript as carrier DNA. The plasmid pRL-CMV (PROMEGA®), in which the expression of Renilla luciferase is controlled by the CMV promoter, was used as an internal control to allow correction for differences in transfection efficiency. Cells were cultured after transfection for 48 hours at different dox concentrations and then lysed in Passive Lysis Buffer (PROMEGA®). Firefly and Renilla luciferase activities were determined with the Dual-Luciferase Reporter Assay (PROMEGA®). The expression of firefly and Renilla luciferase was within the linear range and no squelching effects were observed. The activity of the rtTA variants was calculated as the ratio of the firefly and Renilla luciferase activities, and corrected for between-session variation (Retrovirology, submitted).

Results

Appearance of HIV-rtTA variants with reduced dox-dependence. We have previously reported on the construction of a conditional-live HIV-1 variant (Das et al. 2004b; Verhoef et al. 2001), in which the natural Tat-TAR elements that control viral gene expression and replication were inactivated by mutation and functionally replaced by the rtTA-tetO elements of the Tet-on system for inducible gene expression (FIG. 8A). This HIV-rtTA virus does not replicate constitutively, but exclusively in the presence of dox. We recently reported that long-term replication of this virus resulted in rearrangement of the tetO elements and amino acid substitution in the rtTA protein that significantly improved viral replication without a loss of dox-control. We anticipated that the HIV-rtTA virus could also evolve in different directions (see introduction), and therefore focused this study on the appearance of virus variants that no longer relied on dox for replication. We started multiple long-term virus cultures and followed the development of dox-independence. The evolution approach and the flow chart of the subsequent analyses are illustrated in FIG. 8B. The HIV-rtTA virus was passaged extensively in the presence of dox in 24 independent cultures. At several time points, supernatant samples were taken from the culture and tested in a parallel infection without dox to determine the dox-dependence of the evolved virus. The results for all 24 cultures are summarized in FIG. 8C (black squares). We observed a significant reduction in the number of dox-dependent viruses within 50 days of culturing, and only three cultures remained dox-dependent after 125 days.

The replication curves of the original HIV-rtTA virus and two representative dox-independent virus cultures are shown in FIG. 9. Virus sample C5 did replicate without dox, but can still be activated by dox to some extent, whereas virus sample C6 replicated with similar efficiency with and without dox. Total cellular DNA with integrated provirus was isolated from eight dox-independent HIV-rtTA cultures. We analyzed the sequence of both the "old" Tat-TAR motifs and the "new" rtTA-tetO motifs as they were present in the virus population. In all cultures, the Tat and TAR sequences contained the original mutations, indicating that the Tat-TAR axis of transcriptional activation had not been repaired. In contrast, we observed in all cultures the characteristic rearrangement of tetO elements that had previously been shown to improve dox-dependent HIV-rtTA replication (Marzio et al. 2001; Marzio et al. 2002). Moreover, viruses from all dox-independent cultures had acquired either a G19E or an E37K mutation in the rtTA gene (FIG. 8D). Two of the cultures (B6 and C6) contained additional amino acid substitutions. The repeated selection of G19E or E37K in multiple cultures, combined with their absence in the three remaining cultures (data not shown), strongly suggests their linkage to the acquired dox-independent phenotype.

Amino Acid Substitutions in rtTA Confer the Loss of Dox-Control.

To demonstrate that these rtTA mutations are responsible for the observed viral replication without dox, we constructed HIV-rtTA molecular clones with the G19E or E37K mutation in the rtTA gene and assayed their replication at different dox concentrations (FIG. 10). HIV-rtTA with wild-type rtTA did not replicate without dox and showed a graded increase in viral replication with increasing dox concentrations. HIV-rtTA$_{G19E}$ replicated efficiently both with and without dox. HIV-rtTA$_{E37K}$ also replicated without dox, but replication is more efficient with dox. These results demonstrate that the G19E or E37K mutation is sufficient to reduce the dox-dependence of the HIV-rtTA virus.

The results described above were obtained with the original HIV-rtTA virus, which replicates relatively poorly. We also tested the genetic stability of two improved HIV-rtTA variants in a similar 24-well long-term culture assay. HIV-rtTA 2ΔtetO is identical to HIV-rtTA, but with the improved LTR-2ΔtetO promoter (Marzio et al. 2001; Marzio et al. 2002), and HIV-rtTA$_{F86Y\ A209T}$ contains in addition the improved rtTA$_{F86Y\ A209T}$ gene (Das et al. 2004a). With both viruses we again observed the appearance of variants that replicated without dox, albeit at a significantly slower rate compared with the original HIV-rtTA (FIG. 8C). Whereas the original HIV-rtTA lost dox-control in 50% of the cultures within 50 days, 50% of the HIV-rtTA 2ΔtetO cultures lost dox-dependence in approximately 75 days, and more than 50% of the HIV-rtTA$_{F86Y\ A209T}$ cultures were still fully dox-dependent after 120 days. Apparently, these new HIV-rtTA variants do not only have an improved replication capacity, but also a lower tendency to lose dox-control. Sequence analysis of two dox-independent HIV-rtTA$_{F86Y\ A209T}$ cultures revealed the G19E mutation in both cases.

HIV-rtTA variants with alternative codons at rtTA positions 19 and 37. In the evolution experiments, we observed very specific amino acid substitutions that reduced dox-dependence at only two rtTA positions (G19E and E37K). The introduction of alternative rtTA codons may make such specific amino acid substitutions more difficult or even prevent these unwanted evolutionary routes. For instance, the G19E mutation involves a GGA to GAA codon change, and the G-to-A transition is the most frequent error during HIV-1 reverse transcription. Introduction of an alternative Gly codon (GGU or GGC) would require a much more difficult two-hit mutation, including one transversion, to create a Glu codon (GAA or GAG). Such a difference in the mutational frequency strongly influences the course of HIV-1 evolution.

A similar strategy is not possible for E37K because all possible Glu codons (GAA and GAG) require only a single G-to-A mutation to turn into a Lys codon (AAA or AAG). As an alternative blocking strategy, we could replace the E37-codon with a non-Glu codon that would be more difficult to transform into a Lys codon. However, such an amino acid substitution should ideally not affect the activity or dox-dependence of the rtTA protein. We first examined natural variation at this position in the Tet repressor (TetR). The rtTA protein is based on the E. coli class B TetR ($TetR^{B}$), but there are six additional TetR classes (A, C-E, G, H). TetR from class D, E and H also have the Glu at position 37, but TetR from class A, C and G have a Gln instead. Evolution of a Gln codon (CAA or CAG) to a Lys codon (AAA or AAG) would require only a single C-to-A mutation, but this transversion is less frequently observed in HIV-1 evolution. We therefore constructed an HIV-rtTA variant with a Gln codon (CAG) at position 37 (E37Q). In addition, we constructed variants with either an Asp (GAU; E37D), Asn (AAU; E37N), Ser (UCU; E37S), Arg (CGC; E37R), Phe (UUC; E37F) or a Leu codon (CUU; E37L). The E37D substitution leaves the acidic nature of the residue intact. The E37N and E37S mutations, like the natural variant E37Q, result in polar, uncharged residues. The E37F and E37L mutations result in hydrophobic residues. The E37R substitution creates a basic residue that is similar to the E37K mutation selected through viral evolution. When allowed by the degeneracy of the genetic codon, we chose the codon that requires most mutations to convert into a Lys codon. For example, a CGC rather than an AGA codon was chosen for the E37R variant. Moreover, all new HIV-rtTA variants contain the alternative Gly codon (GGU) at position 19.

We tested replication of these novel HIV-rtTA variants in SupT1 cells with and without dox (FIG. 11). As expected, the virus with the silent codon change at position 19 (E37) replicated dox-dependently. The E37L, E37N, E37F, E37Q and E37R variants also showed efficient and dox-dependent replication. The E37D variant did not replicate with or without dox. Interestingly, the E37S variant replicated efficiently both with and without dox, which is a phenotype similar to that of the E37K variant. This initial survey demonstrates that the HIV-rtTA phenotype is difficult to predict from the chemical nature of the residue, e.g., E37R is similar to E37K, but does not reduce dox-dependence. To construct a more stable dox-dependent virus, it therefore seems necessary to know the impact of all possible amino acid substitutions at position 37.

Testing all Possible Position 37 Variants of rtTA.

We constructed rtTA expression plasmids with all possible amino acids at position 37. The activity of these variants was assayed by transfection into HeLa X1/6 cells (Baron et al. 1997) that contain stably integrated copies of the CMV-7tetO luciferase reporter construct (Gossen et al. 1992). Transfected cells were cultured for two days in the presence of 0-1000 ng/ml dox. We subsequently determined the intracellular luciferase level, which reflects rtTA activity. As shown in FIG. 12A, the activity of these 20 rtTA variants varies considerably. Most variants show no, or very low, activity in the absence of dox, and their activity increases with increasing dox levels.

Comparison of the rtTA activity data (FIG. 12A) with the replication capacity of the selected set of HIV-rtTA variants (FIG. 11) allows us to determine the level of rtTA activity that is required for viral replication. The 37F, 37L, 37N, 37Q and 37R variants show no or very low activity at zero dox (less or equal to 0.06% of the wild-type rtTA activity at 1000 ng/ml dox), and viruses carrying these rtTA variants do not replicate without dox. The low activity (0.09%) of the 37D variant at 1000 ng/ml dox is not sufficient for viral replication either. The 37K and 37S variants show 0.19% and 1% activity without dox, respectively. This level of activity is apparently sufficient to drive a low level of viral replication. The threshold of rtTA activity that is sufficient for HIV-rtTA replication was therefore set at 0.1%. This would mean that not only HIV-$rtTA_{E37K}$ and HIV-$rtTA_{E37S}$, but also HIV-$rtTA_{E37A}$ will replicate in the absence of dox. The codons corresponding to these amino acids are therefore dark grey (but not black) in the codon table (FIG. 12C), and evolution toward these codons should be prevented. All other variants, except for the inactive 37D mutant, show a phenotype similar to wild-type rtTA, i.e., activity below 0.1% at zero dox and much higher than 0.1% at 1000 ng/ml dox. HIV-rtTA viruses with these variants are thus expected to replicate in a dox-dependent manner. These amino acids are light grey in the codon table, and evolution toward them would not result in a loss of dox-dependence. The D and stop codons are marked in black, as the corresponding viruses will not be replication competent.

In the codon table, every change in row or column represents a single nucleotide substitution. This colored codon table (FIG. 12C) thus facilitates the identification of position 37 codons that preserve dox-dependence (light grey) and that require multiple nucleotide mutations to convert into a codon that allows replication in the absence of dox (dark grey). The Leu codons CUN meet these safety requirements.

Testing all Possible Position 19 Variants of rtTA.

Like the E37K mutation, the G19E mutation causes viral replication in the absence of dox. To reveal whether other amino acid substitutions at this position would similarly result in a loss of dox-dependence, we constructed rtTA expression plasmids with all possible amino acids at position 19. The activity of these rtTA variants was analyzed as described above for the position 37 variants. As shown in FIG. 12B, most variants show no or very low activity (less than 0.1%) without dox, and their activity increases with increasing dox levels. In contrast, the 19P variant is inactive, and the 19E variant shows 3% activity without dox. This relatively high basal activity of 19E is in agreement with the efficient replication of the corresponding HIV-rtTA virus without dox. There are multiple codons possible at position 19 that preserve dox-dependence (colored light grey in FIG. 12D) and that require multiple nucleotide mutations to convert into a codon that allows replication in the absence of dox (colored dark grey). For example, the Phe codon UUU meets these safety requirements very well, since it requires three transversions to convert into a Glu codon.

rtTA with Safety-Lock Mutations Prevents the Loss of Dox-Control.

We constructed an rtTA variant that combines the two safety-lock mutations: Phe (UUU) at position 19 (G19F) and Leu (CUU) at position 37 (E37L). This rtTA variant shows very low basal activity (less than 0.1%) and its activity gradually increases with increasing dox levels (FIG. 13A). Although $rtTA_{G19F\ E37L}$ is less active than wild-type rtTA at low dox concentrations, it is highly active at high dox levels. Accordingly, HIV-$rtTA_{G19F\ E37L}$ does not replicate in the absence of dox or at low dox levels, but does replicate efficiently at high dox levels (FIG. 13C). We tested the genetic stability of this virus in 24 long-term cultures with dox (FIG. 8C). The HIV-$rtTA_{G19F\ E37L}$ virus never lost dox-control up to 200 days of culturing. This result demonstrates the increased genetic stability, and thus improved safety, of the novel HIV-rtTA variant.

rtTA Variants with an Alternative Amino Acid at Position 19 or 37 Demonstrate an Improved Transcriptional Activity and Dox-Sensitivity.

Most rtTA variants with an alternative amino acid at position 19 (alanine, cysteine, aspartate, phenylalanine, histidine, isoleucine, lysine, leucine, methionine, asparagine, glutamine, arginine, serine, threonine, valine or tyrosine) and some of the rtTA variants with an alternative amino acid at position 37 (cysteine, methionine, glutamine, arginine or threonine) show an increased transcriptional activity at a low dox concentration and/or an increased transcriptional activity at a high dox concentration when compared with the original (wild-type) rtTA (FIGS. 12 A and B). These results demonstrate that these amino acid substitutions at position 19 and 37 enhance the activity and/or dox-sensitivity of rtTA.

Conclusions

When currently known rtTA is incorporated in a replicating system (e.g., in a replicon), rtTA is at risk of losing dox-control due to mutations at rtTA amino acid position 19 and/or 37 acquired during evolution of the system. Such undesired evolution is prevented by the introduction of alternative codons at these amino acid positions. Preferred alternative codons require multiple nucleotide substitutions to convert into a codon encoding an amino acid that would mediate loss of dox-control of rtTA. As an example we demonstrate that a phenylalanine codon (UUU) at rtTA amino acid position 19 and a leucine codon (CUU) at position 37 improve the genetic stability of rtTA and prevent at least in part the loss of dox-control. Our results demonstrate that other amino acid codons at position 19 (encoding alanine, cysteine, phenylalanine, histidine, isoleucine, leucine, methionine, asparagine, arginine, serine, threonine, valine, tryptophane or tyrosine) and position 37 (encoding histidine, leucine or arginine) similarly improve the genetic stability of rtTA.

The introduction of alternative amino acids at rtTA amino acid position 19 and/or 37 improve the transcriptional activity and/or inducer-sensitivity of rtTA. Specifically, introduction of an alanine, cysteine, aspartate, phenylalanine, histidine, isoleucine, lysine, leucine, methionine, asparagine, glutamine, arginine, serine, threonine, valine or tyrosine at rtTA amino acid position 19, and/or the introduction of a cysteine, methionine, glutamine, arginine or threonine at rtTA amino acid position 37 results in an increased transcriptional activity and/or dox-sensitivity of rtTA.

Example 3

Improved sc rtTA variants

Single-chain Tet transregulators have recently been developed, in which two TetR domains are connected by a peptide linker and one VP16 activation domain or KRAB repressor domain is positioned at the C-terminal end (Krueger et al. 2003). These transregulators fold intramolecularly and do not dimerize with each other. Unfortunately, the single-chain version of rtTA (sc rtTA) exhibits reduced activity when compared with the regular rtTA, and this low activity may thwart its use in applications that require an active Tet-on system.

We have incorporated the rtTA gene and the tetO elements into the HIV-1 genome to control virus replication. During culturing of this dox-dependent virus, spontaneous viral evolution selected for improved virus variants, in which the introduced Tet-on system was optimized. We have identified several amino acid substitutions in the rtTA gene that greatly enhance the transcriptional activity and dox-sensitivity of the transactivator. To test whether these mutations similarly improve other TetR-based transactivators, we introduced them into sc rtTA. All mutations enhanced sc rtTA activity. The most active sc rtTA variant is ~30-fold more active than the original sc rtTA, and is almost as active as the regular rtTA.

Materials and Methods

Construction of sc rtTA variants. The plasmids pCMV-rtTA and pCMV-scrtTA contain the $rtTA2^{S}$-S2 and sc rtTA2-S2 genes, respectively, cloned in the expression vector pUHD141-1/X (Krueger et al. 2003; Urlinger et al. 2000). The sc rtTA gene contains two TetR domains and a single activation domain. To introduce mutations into the N-terminal TetR domain, the EcoRI-BfuAI fragment of pCMV-scrtTA was replaced with the corresponding fragment of the appropriate pCMV-rtTA plasmid. Mutations were introduced into the C-terminal TetR domain of sc rtTA by mutagenesis PCR (Mikaelian et al. 1992) on pCMV-scrtTA with the mutagenic primers (primer M) scrtTA-V9I (5'-GGCTCTAGATCTCGTTTAGATAAAAGTAAAATCAT-TAACAGCGCA-3') (SEQ ID NO:18), scrtTA-F675 (5'-AGGCACCATACTCACTCTTGCCCTTTA-3') (SEQ ID NO:19), scrtTA-F86Y (5'-AACGCTAAAAGTTATA-GATGTGCT-3') (SEQ ID NO:20), or scrtTA-G138D (5'-CAGCGCTGTGGACCACTTTACTTTA-3') (SEQ ID NO:21) and the primers 5'-TAATCATATGTGGCCTG-GAGAA-3' (primer 1) (SEQ ID NO:22), 5'-AGGCGTATT-GATCAATTCAAGGCCGAATAAG-3' (primer 2) (SEQ ID NO:23), and 5'-TCACTGCATTCTAGTTGTGGT-3' (primer 3) (SEQ ID NO:24) as described above for the tTA mutations. The final PCR products were digested with BglII and SmaI and used to replace the corresponding fragment of pCMV-scrtTA. All constructs were verified by sequence analysis.

Cell culture and rtTA activity assay. The activity of rtTA and sc rtTA was assayed in HeLa X1/6 cells (Baron et al. 1997), which are HeLa-derived cells containing chromosomally integrated copies of the CMV-7tetO luciferase reporter construct pUHC13-3 (Gossen et al. 1992). Cells were cultured at 37° C. and 5% $CO_2$ in Dulbecco's modified Eagle's medium supplemented with 10% fetal calf serum, minimal essential medium nonessential amino acids, penicillin (100 U/ml), and streptomycin (100 μg/ml). Cells were grown in 2-$cm^2$ wells to 60% confluency and transfected with the pCMV-rtTA or pCMV-scrtTA expression plasmids and the plasmid pRL-CMV (PROMEGA®) by the calcium phosphate precipitation method. pRL-CMV expresses Renilla luciferase from the CMV promoter and was used as an internal control to allow correction for differences in transfection efficiency. 1 μg of DNA mixture in 15 μl water was mixed with 25 μl of 50 mM HEPES (pH 7.1)-250 mM NaCl-1.5 mM $Na_2HPO_4$ and 10 μl of 0.6 M $CaCl_2$, incubated at room temperature for 20 min, and added to the culture medium. The DNA mixture consisted of 20 ng pCMV-scrtTA or pCMV-rtTA, 2 ng pRL-CMV, and 978 ng pBluescript for sc rtTA or rtTA activity assay. Cells were cultured after transfection for 48 hours at different dox (D-9891, Sigma) concentrations and then lysed in Passive Lysis Buffer (PROMEGA®). Firefly and Renilla luciferase activities were determined with the Dual-Luciferase Reporter Assay (PROMEGA®). The expression of firefly and Renilla luciferase was within the linear range and no squelching effects were observed. The activity of the transactivators was calculated as the ratio of the firefly and Renilla luciferase activities, and corrected for between-session variation.

Results

Mutations Observed in rtTA Improve sc rtTA Activity.

In sc rtTA, two TetR domains are connected head to tail by a peptide linker, and a single activation domain is fused to the C-terminal TetR domain. The mutations that did improve rtTA activity are all positioned within the TetR domain of the protein (FIG. 16). To test whether these beneficial mutations of rtTA can also improve the activity and dox-sensitivity of sc rtTA, we introduced them into either one or both of the TetR domains of sc rtTA. Activity of these variants was analyzed in HeLa X1/6 cells and compared with the activity of rtTA and the original (wild-type) sc rtTA (FIG. 18). Both rtTA and wild-type sc rtTA show no background activity without dox and their activity increases gradually with increasing dox levels. However, the induced activity of sc rtTA is much lower than that of rtTA at all tested dox concentrations. For example, sc rtTA is about 40-fold less active than rtTA at 1000 ng/ml dox (FIG. 18A). Introduction of the F86Y mutation in the N-terminal TetR domain increased se rtTA activity ~10-fold at all dox levels, but did not affect background activity. The additional introduction of the V9I mutation into the F86Y variant also improved sc rtTA activity (albeit marginally), whereas the addition of the F67S, G138D, or V9I plus G138D mutations further improved sc rtTA activity ~2-fold at all dox levels. The background activity of these variants was not increased.

Similar results were obtained upon introduction of the mutations into the C-terminal TetR domain of sc rtTA (FIG. 18B). However, none of these variants are as active as their counterparts with mutations in the N-terminal TetR domain. The F86Y mutation increased sc rtTA activity ~3-fold, and the addition of the F67S, G138D, or V9I plus G138D mutations further increased activity ~2-fold. These results demonstrate that the activity of sc rtTA is improved by mutations in either TetR domain. Mutations introduced into the N-terminal TetR domain have a larger effect on sc rtTA activity than the same mutations in the C-terminal domain.

Introduction of the mutations in both TetR domains resulted in the most active sc rtTA variants (FIG. 18C). At high dox levels (500-1000 ng/ml), all these variants demonstrate a higher transcriptional activity than the corresponding variants with mutations in only one of the two TetR domains (FIGS. 18A and 18B). For instance, the sc rtTA with the F86Y mutation in both TetR domains is ~13-fold more active than wild-type sc rtTA at 1000 ng/ml dox, whereas the same mutation in the N-terminal or in the C-terminal TetR domain increased sc rtTA activity ~10-fold and ~3-fold, respectively. The variants carrying the F67S, G138D, or V9I plus G138D mutations in addition to the F86Y mutation in both TetR domains are not only more active at high dox levels, but also more active at low dox levels (10-100 ng/ml). In fact, these variants demonstrate a transcriptional activity and dox-sensitivity similar to rtTA.

Discussion

We have identified amino acid substitutions in rtTA that greatly improve the transcriptional activity and dox-sensitivity of the transactivator. In this example, we tested whether these mutations similarly affect sc rtTA. Our results demonstrate that all mutations did significantly enhance sc rtTA activity. Both the transactivators rtTA and sc rtTA are activated by doxycycline. Our results demonstrate that the sc rtTA activity is significantly improved by introduction of at least one mutation that enhances rtTA activity. The most active sc rtTA variant in this study was obtained by introducing beneficial mutations in both TetR domains. However, sc rtTA is also improved by at least one mutation in only one of the TetR domains. The sc rtTA variants with beneficial mutations in the N-terminal TetR domain appear to be more active than the variants with the same mutations in the C-terminal TetR domain.

The sc rtTA variant with the F67S and F86Y mutations in both TetR domains is ~30-fold more active than the original sc rtTA at high dox levels, and does not show any background activity in the absence of dox. This novel sc rtTA is almost as active and dox-sensitive as rtTA, and is therefore suitable for replacing the regular rtTA in applications where multiple TetR-based regulatory systems are used in the same cell or organism.

Conclusion

The transcriptional activity and inducer-sensitivity of single chain rtTA activity is significantly improved by the introduction of amino acid substitutions that were found by us to improve the transcriptional activity and inducer-sensitivity of rtTA. We thus for instance generated sc rtTA variants with an up to ~30-fold increased transcriptional activity and an increased dox-sensitivity by the introduction of a F86Y, a V9I, a F67S and/or a G138D amino acid substitution into the original sc rtTA.

Example 4

Development of Novel rtTA Variants with Improved Genetic Stability; Introduction of Alternative Amino Acids at rtTA Position 19, 37 and 56

We have demonstrated that long-term replication of HIV-rtTA resulted in virus variants that no longer depend on dox for replication. This reduced dox-dependence was associated with an amino acid substitution in the rtTA protein either at position 19 (glycine to glutamic acid; G19E) or at position 37 (glutamic acid to lysine; E37K). We developed an HIV-rtTA variant with safety-lock mutations (G19F and E37L) in the rtTA gene to block these undesired evolutionary routes. This novel variant showed improved genetic stability and did not lose dox-control in long-term cultures with dox (see example 2).

As a vaccine, replication of HIV-rtTA would be temporally switched on to induce anti-viral immune responses. Subsequent dox-withdrawal impose alternative evolutionary pressure on the virus than long-term culturing with dox. Specifically, there is a risk of rtTA variants with a tTA-like phenotype, which are active without dox and inhibited by dox, appearing in dox-washout experiments, whereas such variants are counter selected in the presence of dox. We therefore followed evolution of HIV-rtTA in multiple, independent virus cultures that were transiently activated by dox. The virus did indeed lose dox-control in a significant number of cultures after dox-withdrawal. We identified a typical amino acid substitution at position 56 in the rtTA protein, which was found to be responsible for the dox-independent replication. This mutation had never been observed in long-term cultures with dox. We developed a novel rtTA variant that blocks this undesired evolutionary route and thus improves the genetic stability and safety of HIV-rtTA.

Materials and Methods

Virus cultures. The HIV-rtTA infectious molecular clone is a derivative of the HIV-1 LAI proviral plasmid (Peden et al. 1991) and was described previously (Das et al. 2004b; Verhoef et al. 2001). HIV-rtTA used in this study contains the inactivating Y26A mutation in the Tat gene, five nucleotide substitutions in the TAR hairpin motif, the $rtTA_{F86Y\ A209T}$ gene (Das et al. 2004a) in place of the nef gene, and the LTR-2ΔtetO promoter configuration (Marzio et al. 2001; Marzio et al. 2002).

SupT1 T cells were cultured at 37° C. and 5% $CO_2$ in RPMI1640 medium containing 10% fetal bovine serum (FBS), 100 units/ml penicillin, and 100 μg/ml streptomycin. SupT1 cells were transfected with HIV-rtTA molecular clones by electroporation. Briefly, $5\times10^6$ cells were washed in RPMI1640 with 20% FBS and mixed with 5 μg of DNA in 250 μl RPMI1640 with 20% FBS. Cells were electroporated in 0.4-cm cuvettes at 250 V and 975 μF and subsequently resuspended in RPMI1640 with 10% FBS. The CA-p24 level in the cell-free culture supernatant was determined by antigen capture enzyme-linked immunosorbent assay (ELISA) (Back et al. 1996).

The evolution experiment was started with transfection of 15 μg HIV-rtTA proviral plasmid into $1.5\times10^7$ SupT1 cells. Cells were split into 12 independent cultures and dox (Sigma D-9891) was added to initiate viral replication. Three days after transfection, dox was removed from the cultures by washing the cells twice with medium, each followed by a 30 min incubation at 37° C. and 5% $CO_2$ to allow release of dox from cells. Cells were subsequently resuspended in medium and cultured without dox. If virus replication was apparent as indicated by the formation of syncytia, the virus containing culture supernatant was passaged onto fresh SupT1 cells. Infected cell samples were used to analyze the proviral rtTA sequence.

Proviral DNA analysis of evolved sequences. HIV-rtTA infected cells were pelleted by centrifugation and washed with phosphate-buffered saline. Total cellular DNA was solubilized by resuspending the cells in 10 mM Tris-HCl (pH 8.0)-1 mM EDTA-0.5% Tween 20, followed by incubation with 200 μg/ml of proteinase K at 56° C. for 60 min and 95° C. for 10 min. The proviral rtTA genes were PCR amplified with primers tTA1 (5'-ACAGCCATAGCAGTAGCTGAG-3') (SEQ ID NO:1) and tTA-rev2 (5'-GATCAAGGATATCTTGTCTTCGT-3') (SEQ ID NO:2), and sequenced with the bigdye terminator cycle sequencing kit (Applied Biosystems).

Construction of novel rtTA expression plasmids and HIV-rtTA variants. The plasmid pCMV-rtTA contains the $rtTA2^S$-S2 gene in the expression vector pUHD141-1/X (Urlinger et al. 2000). To introduce the P56S mutation, the proviral PCR product with this mutation was digested with XbaI and SmaI and used to replace the corresponding fragment in pCMV-rtTA. To generate rtTA variants with the G19F and E37L mutations and different amino acids at position 56, mutagenesis PCR was performed on pCMV-$rtTA_{G19F\ E37L}$ (example 2) with the sense primer random-rtTA-56 (5'-AAGCGGGCCCTGCTCGATGCCCTGNNKATCGAGATGCTGGACAGGC-3', with K corresponding to G or T, and N corresponding to G, A, T or C) (SEQ ID NO:25) plus the antisense primer CMV2 (5'-TCACTGCATTCTAGTTGTGGT-3') (SEQ ID NO:15). Mutant rtTA sequences were cloned as ApaI-BamHI fragments into pCMV-$rtTA_{G19F\ E37L}$. Novel rtTA sequences were cloned into the shuttle vector pBlue3'LTRext-deltaU3-$rtTA_{F86Y\ A209T}$-2ΔtetO (Das et al. 2004a) using the XcmI and NdeI sites and subsequently cloned into the HIV-rtTA molecular clone as BamHI-BglI fragments. All constructs were verified by sequence analysis.

rtTA activity assay. pLTR-2ΔtetO-luc expresses firefly luciferase from the LTR-2ΔtetO promoter derived from the HIV-rtTA molecular clone (Marzio et al. 2001; Marzio et al. 2002). pCMV-7tetO-luc, previously named pUHC13-3 (Gossen & Bujard, 1992), contains seven tetO elements located upstream of a minimal CMV promoter and the firefly luciferase gene. The plasmid pRL-CMV (PROMEGA®), in which the expression of Renilla luciferase is controlled by the CMV promoter, was used as an internal control to allow correction for differences in transfection efficiency. HeLa X1/6 cells are derived from the HeLa cervix carcinoma cell line and harbor chromosomally integrated copies of the CMV-7tetO firefly luciferase reporter construct (Baron et al. 1997). HeLa X1/6 and C33A cervix carcinoma cells (ATCC HTB31) (Auersperg, 1964) were cultured at 37° C. and 5% $CO_2$ in Dulbecco's modified Eagle's medium (DMEM) supplemented with 10% FBS, minimal essential medium nonessential amino acids, 100 units/ml penicillin, and 100 μg/ml streptomycin.

C33A and HeLa X1/6 cells were grown in 2-$cm^2$ wells to 60% confluency and transfected by the calcium phosphate precipitation method. 1 μg of DNA mixture in 15 μl water was mixed with 25 μl of 50 mM HEPES (pH 7.1)-250 mM NaCl-1.5 mM $Na_2HPO_4$ and 10 μl of 0.6 M $CaCl_2$, incubated at room temperature for 20 min and added to the culture medium. The DNA mixture consisted of 0.4 ng pCMV-rtTA, 20 ng pLTR-2ΔtetO-luc or pCMV-7tetO-luc, 0.5 ng pRL-CMV, and 980 ng pBluescript as carrier DNA for C33A cells, or 8 ng pCMV-rtTA, 2.5 ng pRL-CMV, and 990 ng pBluescript for HeLa X1/6 cells. Transfected cells were cultured for 20 hours at different dox concentrations, washed with DMEM, and subsequently cultured for 24 hours with fresh medium containing dox (the same concentrations as before the wash step). Cells were then lysed in Passive Lysis Buffer (PROMEGA®), and firefly and Renilla luciferase activities were determined with the Dual-Luciferase Reporter Assay (PROMEGA®) using a GloMax microplate luminometer (PROMEGA®). The expression of firefly and Renilla luciferase was within the linear range and no squelching effects were observed. The activity of the rtTA variants was calculated as the ratio of the firefly and Renilla luciferase activities, and corrected for between-session variation.

Results

Evolution of HIV-rtTA after transient dox administration. To test the genetic stability of HIV-rtTA upon removal of the effector dox, we started 12 independent virus cultures in SupT1 T cells with dox (FIG. 20B). Viral replication resulted in the production of CA-p24 and the appearance of syncytia in all cultures. At day 3, we washed the cultures to remove dox, which resulted in silencing of viral replication as was obvious from the decrease in CA-p24 levels and the disappearance of syncytia in all cultures. However, CA-p24 levels started to increase again at day 10-20, and continued culturing resulted in high CA-p24 levels and formation of large syncytia. At the peak of infection, the virus was passaged onto fresh SupT1 cells and cultured without dox. All viruses were able to initiate a spreading infection, indicating that they had lost dox-control. Total cellular DNA with integrated proviruses was isolated from the cultures and the rtTA gene was PCR-amplified and sequenced. In all cultures, the virus had acquired a point mutation (CCA to UCA) in the rtTA gene that resulted in a Proline to Serine substitution at position 56 (P56S).

Similar results were obtained with HIV-rtTA$_{V9I\ G138D}$, an improved HIV-rtTA variant with two rtTA mutations (V9I and G138D) (example 1). The evolved viruses started to replicate without dox in 10 of the 12 cultures (FIG. 20C). Nine virus cultures had acquired the P56S mutation, whereas one culture had obtained the previously described G19E mutation (example 2). In the two remaining cultures, CA-p24 levels stably decreased after dox removal and no viral replication was observed upon prolonged culturing. At day 64, these cultures were split and continued with and without dox. While the cultures without dox remained negative for CAp24, spreading infections were apparent in the cultures with dox (FIG. 20C). Thus, the virus in these two cultures remained dox-dependent and can be readily reactivated.

P56S mutation causes a tTA-like phenotype. The repeated selection of the P56S mutation in multiple, independent cultures strongly suggests its linkage to the observed loss of dox-control. To demonstrate that this amino acid substitution is indeed responsible for an altered rtTA phenotype, we cloned the P56S-mutated rtTA gene into the expression plasmid pCMV-rtTA and assayed its activity in a regular Tet-on system. The rtTA expression plasmid was transfected into C33A cells together with a reporter plasmid in which luciferase expression is controlled by the viral LTR-2ΔtetO promoter (Marzio et al. 2001; Marzio et al. 2002). Transfected cells were cultured for two days at different dox concentrations. We subsequently determined the intracellular luciferase level, which reflects rtTA activity (FIG. 21A). Wild-type rtTA shows no activity without dox or with a low dox level (10 ng/ml), and its activity gradually increases at higher dox concentrations. In contrast, the P56S variant exhibits a very high activity without dox, and its activity is inhibited, instead of activated, by increasing dox concentrations. This phenotype is similar to that of the transcriptional activator tTA, which differs from rtTA by four amino acids, including an Alanine instead of Proline at position 56 (Urlinger et al. 2000). The high activity of the P56S variant in the absence of dox explains its appearance in the dox-washout experiments, whereas its low activity with dox explains why we never observed this mutation in long-term cultures of HIV-rtTA in the presence of dox.

We also analyzed rtTA activity in C33A cells transfected with a luciferase reporter under the control of a minimal CMV promoter coupled to an array of seven tetO elements (Gossen & Bujard, 1992), and in HeLa X1/6 cells that contain stably integrated copies of this CMV-7tetO luciferase construct (Baron et al. 1997). In both assays, we observed similar results as with the viral LTR-2ΔtetO promoter construct (FIGS. 21B and 21C), demonstrating that the tTA-like phenotype of rtTA$_{P56S}$ is not dependent on the type of promoter, nor on the episomal or chromosomal state of the reporter gene.

HIV-rtTA$_{G19F\ E37L}$ can lose dox-control by a P56S mutation. We have previously constructed an HIV-rtTA variant with the safety-lock mutations G19F and E37L that prevent the virus from losing dox-control during long-term culturing with dox (example 2). We now tested the stability of HIV-rtTA$_{G19F\ E37L}$ in the dox-washout experiment. This virus did lose dox-control in only one of the 12 cultures, and all other cultures did not show any replication in the absence of dox (FIG. 20D). Sequence analysis revealed that the escape variant had acquired the P56S mutation. This result demonstrates that although HIV-rtTA$_{G19F\ E37L}$ showed a lower tendency to lose dox-control than the original virus without safety-lock mutations (FIG. 20B), the escape route at position 56 is preferably blocked in order to further improve the genetic stability of the virus.

Safety-lock mutation at position 56. The P56S mutation is caused by a single nucleotide substitution (CCA to UCA). Such single nucleotide transitions (pyrimidine-pyrimidine or purine-purine substitutions) occur at a much higher frequency than single nucleotide transversions (pyrimidine-purine substitutions) or multiple nucleotide changes during HIV-1 reverse transcription (Berkhout et al. 2001; Berkhout & de Ronde, 2004). This mutational bias strongly influences the course of virus evolution (Keulen et al. 1996; Keulen et al. 1997). Accordingly, the undesired evolutionary route at position 56 is blocked by introducing alternative amino acid codons that require multiple nucleotide changes for HIV-rtTA to lose dox-control. In fact, we have successfully blocked the escape routes at positions 19 and 37 by such safety-lock mutations, which demonstrate the effectiveness of this strategy (example 2). To block all three observed escape routes of HIV-rtTA at the same time, the position 56 safety-lock mutation is ideally combined with the positions 19 and 37 mutations. To identify suitable amino acid substitutions, we made rtTA expression plasmids with all possible amino acids at position 56 in combination with the G19F and E37L mutations, and assayed their activity in HeLa X1/6 cells.

The activity of these 20 rtTA variants varies considerably (FIG. 22A). Like the S variant, the A, C and H variants exhibit a tTA-like phenotype, since their activity is relatively high in the absence of dox and drops with increasing dox levels. Except for the F and M variants that are completely inactive, the other variants exhibit an rtTA phenotype, since their activity increases with a rising dox level. However, the basal and induced activities of these variants (at 0 and 1000 ng/ml dox, respectively) differ significantly. Because the L variant shows an rtTA phenotype with a very low basal activity, we introduced this variant into HIV-rtTA and tested viral replication in SupT1 T cells. This virus did not replicate without dox, but also not with dox (data not shown), indicating that the induced activity of the L variant (~0.3% of the wild-type rtTA activity at 1000 ng/ml dox) is not sufficient for HIV-rtTA replication. This is in agreement with our observation that the wild-type rtTA does not support viral replication at 10 ng/ml dox (~0.4% rtTA activity; wt in FIG. 22A) and rtTA$_{G19F\ E37L}$ does not support replication at 100 ng/ml dox (~0.4% rtTA activity; P variant in FIG. 22A). All these results indicate that the E, F, L and M variants with both their basal and induced activities lower than 0.4% will not support viral replication. We therefore colored the codons corresponding to these amino acids and the stop codons in black (FIG. 22B). The basal activity of the A, C, G, H, N, S, and Y variants is higher than 0.4%. Since the corresponding HIV-rtTA viruses are at risk of replicating without dox, their codons are dark grey (but not totally black). The other variants that show a low basal activity (<0.4%) and a high induced activity (>0.4%) result in dox-dependent viruses, and their codons are light grey.

In the codon table, every change in row or column represents a single nucleotide substitution. Apparently, the only position 56 codon that preserves dox-dependence (light grey) and requires more than a single nucleotide mutation to be converted to a codon that allows replication without dox (dark grey) is the AUA codon encoding an Isoleucine. However, the activity of the I variant at 1000 ng/ml dox is only 1% of the wild-type level (FIG. 22A), which may result in a poorly replicating virus. The K and Q variants, which show a dox-dependent activity similar to the P variant ($rtTA_{G19F\ E37L}$), require at least one nucleotide transversion to be converted to a dox-independent variant. It has been shown that transversions occur less frequently than transitions during HIV-1 reverse transcription (Berkhout et al. 2001; Berkhout & de Ronde, 2004). For instance, we did frequently observe a P56S mutation (caused by a CCA to UCA transition), but never a P56A mutation (would require a CCA to GCA transversion) in the dox-washout experiment, although both mutations would cause a similarly high activity in the absence of dox (FIG. 22A). Therefore, introduction of an AAG (K) or CAG (Q) codon at rtTA position 56 blocks the appearance of dox-independent virus variants upon dox-withdrawal.

Blocking loss of dox-control by triple safety-lock rtTA variant. We constructed HIV-rtTA molecular clones carrying triple safety-lock mutations G19F, E37L and P56K or P56Q, and tested their replication in SupT1 T cells with and without dox (FIG. 23). Both viruses replicated in a dox-dependent manner. However, whereas replication of HIV-$rtTA_{G19F\ E37L\ P56K}$ was as efficient as the double safety-lock variant HIV-$rtTA_{G19F\ E37L}$, HIV-$rtTA_{G19F\ E37L\ P56Q}$ replicated less efficiently. We therefore focused our studies on the HIV-$rtTA_{G19F\ E37L\ P56K}$ variant and tested the genetic stability of this virus in long-term cultures with dox and in dox-washout experiments. We started 24 long-term cultures with dox and tested virus replication in the presence and absence of dox at several time points (as described previously in example 2). All virus cultures stayed fully dox-dependent during the 100 days of culture, and sequence analysis revealed that the safety-lock mutations were stably maintained in all cultures (data not shown). To test the genetic stability of HIV-$rtTA_{G19F\ E37L\ P56K}$ after transient dox administration, we started 24 virus cultures with dox (FIG. 24). Virus replication resulted in the production of detectable amounts of CA-p24 and the appearance of syncytia in all cultures. Upon dox-withdrawal at day 3, the CA-p24 level dropped and syncytia disappeared, and no sign of viral replication could be detected in any of the 24 cultures in the following months. At day 60, all cultures were split and continued with and without dox. While there was no viral replication in the cultures without dox, administration of dox did result in spreading infections, which indicate that the virus in all cultures stayed dox-dependent, and the undetectable CA-p24 levels in dox minus cultures were not due to loss of proviral genomes or total silencing of the viral promoter. Thus, replication of HIV-$rtTA_{G19F\ E37L\ P56K}$ stays dox-dependent in both long-term cultures with dox and transiently activated cultures, demonstrating that the triple safety-lock mutations at rtTA positions 19, 37 and 56 completely block the loss of dox.

Conclusions

Our virus evolution experiments demonstrate that HIV-rtTA is at risk of escaping from dox-control by an amino acid substitution in rtTA at position 19, 37 or 56. To generate a safe HIV-rtTA virus, all three evolutionary routes are preferably blocked. We have previously blocked the position 19 and 37 routes by safety-lock mutations (e.g., G19F and E37L) that require multiple nucleotide changes to lose dox-control (example 2). We here demonstrate that the position 56 escape route is efficiently blocked by the introduction of an alternative amino acid at position 56 (e.g., P56K or P56Q) that requires at least one nucleotide transversion to convert rtTA into a dox-independent variant.

TABLE 1

Naturally evolved and constructed rtTA variants

| rtTA | Mutations | Times in culture | Natural variation in TetR A | B | C | D | E | G | H |
|---|---|---|---|---|---|---|---|---|---|
| wild-type [a] | — | — | | | | | | | |
| V1 | F86Y A209T [b] | — | F | F | F | F | F | F | F |
| V2 | V9I | 2 | V | V | V | V | V | V | V |
| V3 | F67S | 2 | S | F | S | S | S | S | V |
| V4 | G138D | 7 | S | G | S | S | S | S | A |
| V5 | E157K | 2 | E | E | E | D | E | E | E |
| V6 | R171K | 1 | R | R | Q | R | Q | H | T |
| V7 | V9I G138D | 1 | | | | — | | | |
| V8 | V9I E157K | 1 | | | | — | | | |
| V9 | V9I R171K | 1 | | | | — | | | |
| V10 | F67S R171K | 1 | | | | — | | | |
| V11 | V9I F67S | — | | | | — | | | |
| V12 | F67S G138D | — | | | | — | | | |
| V13 | F67S E157K | — | | | | — | | | |
| V14 | V9I F67S G138D | — | | | | — | | | |
| V15 | V9I F67S E157K | — | | | | — | | | |
| V16 | V9I F67S R171K | — | | | | — | | | |
| V17 | V9I G138D E157K | — | | | | — | | | |
| V18 | V9I G138D R171K | — | | | | — | | | |

[a] The wild-type rtTA was previously described as $rtTA2^S$-S2 (Urlinger et al. 2000).

[b] All variants (V1-V18) contain the F86Y (in the TetR domain) and A209T (in the VP16 activation domain) mutations.

BRIEF DESCRIPTION OF THE DRAWING

FIGS. 14A and 14B. Transcriptional activity and dox-sensitivity of wild type, naturally evolved and constructed rtTA variants. Transfection assays were performed in HeLa X1/6 cells, see FIG. 2 for details. Transcriptional activity observed at 1000 ng/ml dox is shown as average value of three transfections with error bars indicating the standard deviation. The wild-type rtTA activity was set at 100%. Dox-sensitivity is compared with the wild-type rtTA of which the sensitivity is arbitrarily set at 1. For each rtTA variant, the dox concentration (ng/ml) that results in an activity comparable to that of the wild-type rtTA activity at 1000 ng/ml dox is indicated between brackets (Part of these results is also shown in FIG. 3).

FIG. 14C. rtTA variants. Each column row depicts suitable rtTA variants.

FIG. 15. Novel rtTA variants can be activated by dox-like compounds. The rtTA activity was measured in HeLa X1/6 cells, see FIG. 2 for details. Cells were cultured in the presence of different concentrations of Tc or Mc (0-10000 ng/ml). The wild-type (wt) rtTA activity at 1000 ng/ml dox (not shown) was set at 100%.

FIG. 16. TetR-based transactivators. (A and B) In the homodimeric rtTA, each monomer contains an N-terminal E. coli-derived TetR domain and a C-terminal herpes simplex virus VP16-derived activation domain. The V91, F67S, F86Y and G138D mutations that enhance rtTA activity are all located in the TetR domain. sc rtTA is a single-chain version of rtTA. It contains two TetR domains connected head to tail by a peptide linker and a single activation domain at the C-terminal end.

FIG. 19. Nucleotide and amino acid sequence of rtTA (*SEQ ID NO: 26 and SEQ ID NO: 27*). Shown is the nucleotide sequence (upper line) and amino acid sequence (lower line) of the rtTA2$^{S}$-S2 variant (Urlinger et al. 2000).

FIG. 22. Activity of $rtTA_{G19F\ E37L}$ variants with all possible amino acids at position 56. (A) The activity of rtTA was measured in HeLa X1/6 cells, see FIG. 21 for details. All variants carry the G19F, E37L, F86Y and A209T mutations in combination with different amino acids at position 56. The wild-type rtTA (wt) carrying only the F86Y and A209T mutations was included as a control, of which the activity at 1000 ng/ml dox was arbitrarily set at 100%. Average values of two transfections are shown with the error bar indicating the standard deviation. (B) Codon table of $rtTA_{G19F\ E37L}$ variants with all possible amino acids at position 56. The corresponding codons of inactive variants are marked in black, of dox-dependent variants in light grey, and of variants that are active without dox in dark grey. See the text for details.

REFERENCES

Figure 1:
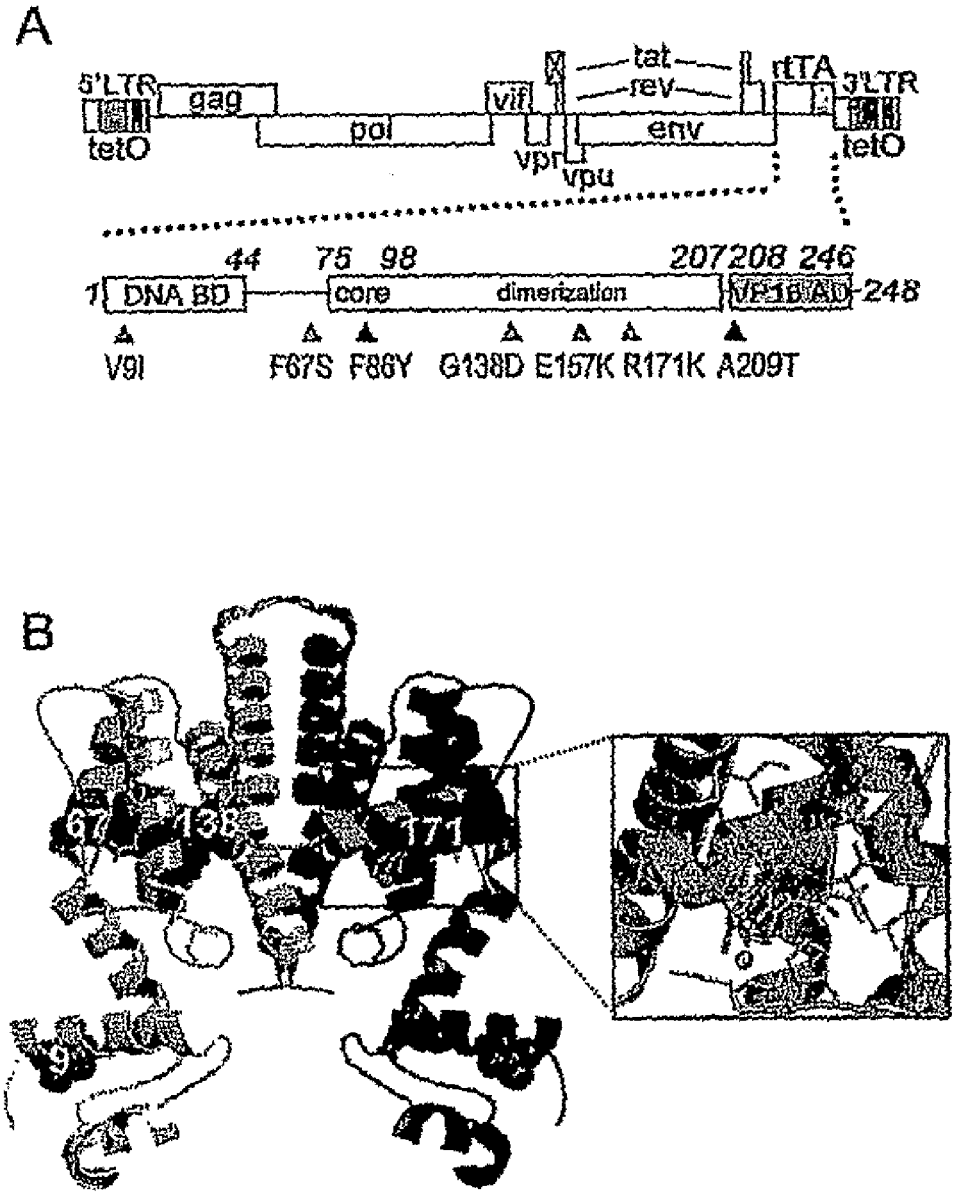
FIG. 1. Mutation of the rtTA gene through viral evolution. (A) In the HIV-rtTA virus, the Tat-TAR axis of transcription regulation has been inactivated by mutation of both Tat and TAR (crossed boxes). Transcription and replication of the virus were made dox-dependent by introduction of tetO elements in the LTR promoter region and replacing the nef gene by the rtTA gene. This 248-amino acid protein is a fusion of the E. coli Tet repressor (TetR) and the VP16 activation domain (AD) of the herpes simplex virus. The TetR part can be subdivided in a DNA binding domain (BD) (α-helices 1-3) and a regulatory core domain (α-helices 5-10) with a dimerization surface (α-helices 7-10). The F86Y (dark grey triangle) and A209T (black triangle) mutations were present in the starting virus and maintained in all long-term cultures. Light grey triangles indicate additional amino acid exchanges in rtTA that were observed in multiple, independent cultures of HIV-rtTA$_{-F86Y\ A209T}$. (B) The crystal structure of the TetR homodimer (one monomer in dark grey, the other in light grey) complexed with Tc (light grey) and $Mg^{2+}$ (grey ball) (Hinrichs et al. 1994; Kisker et al. 1995). Residue 86 is shown in dark grey. Additional mutated amino acids (positions 9, 67, 138, and 171) are shown in light grey. Residue 157 is not shown, because the segment 156 to 164 is flexible and not determined in the TetR crystal structure. A close up of the Tc-binding region is shown at the right. There are seven classes of TetR proteins (A-E, G, H) with a highly conserved sequence. The high resolution crystal structure that is shown is based on class D (TetR$^D$). rtTA is based on class B (TetR$^B$), which shares 63% sequence identity with TetR$^D$. The crystal structure of TetR$^B$ at medium resolution revealed an identical polypeptide fold (Hinrichs et al. 1994). Therefore, we can assume that the interactions of TetR with Tc and $Mg^2$ will be nearly identical in both classes. Figures are drawn using the 2TCT coordinates from the Protein Data Bank and the MOL-SCRIPT (Kraulis, 1991) and RASTER3D (Merritt et al. 1997) programs.
Figure 2:
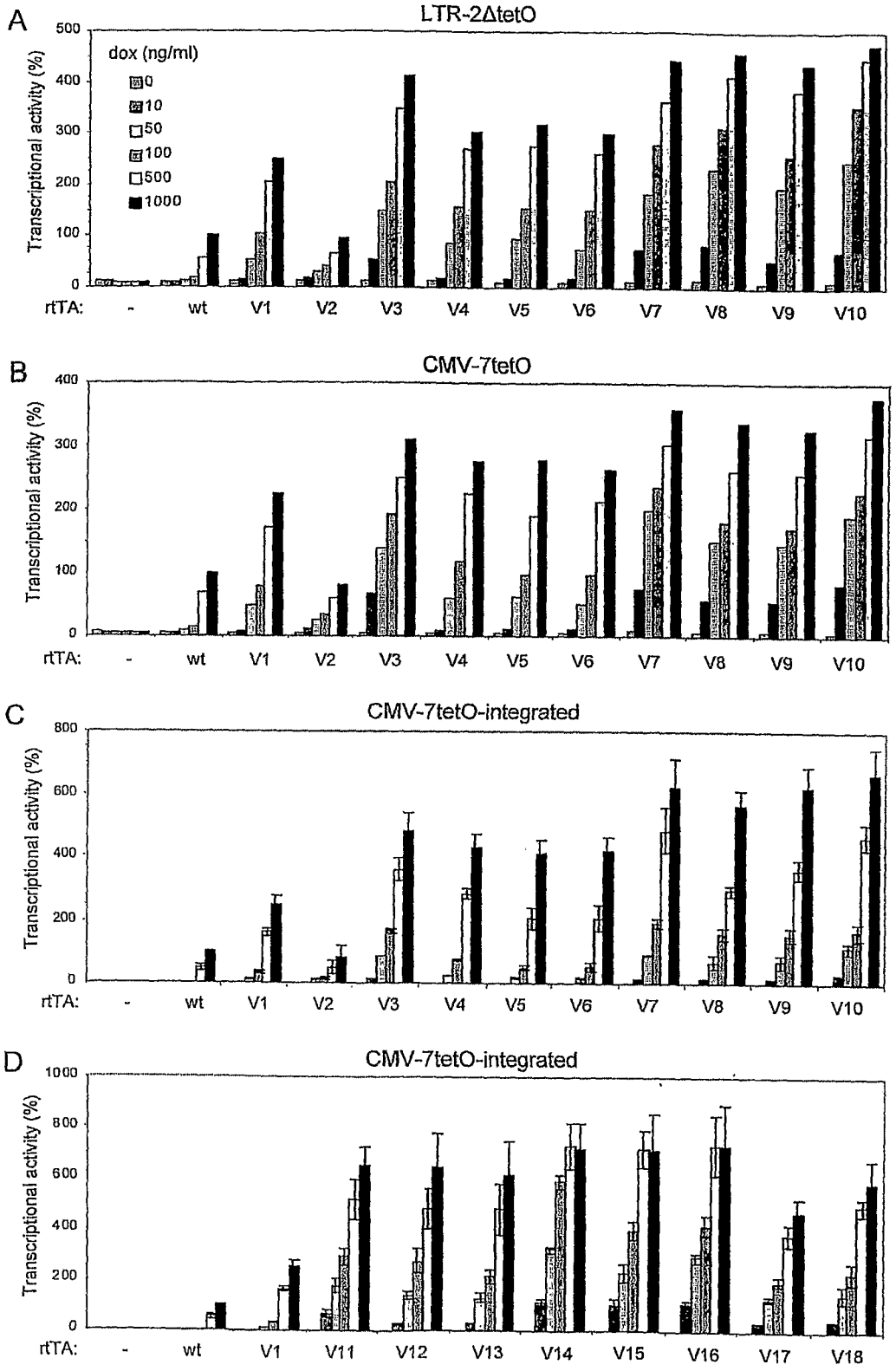
FIG. 2. Novel rtTA variants show increased activity and dox-sensitivity in different Tet systems. The transcriptional activity of rtTA variants was measured in C33A cells transfected with a plasmid carrying the firefly luciferase reporter gene under the control of the viral LTR-2ΔtetO promoter (LTR-2ΔtetO; A) or under the control of a minimal CMV-derived promoter coupled to seven tetO elements (CMV7-tetO; B). Furthermore, rtTA activity was measured in HeLa X1/6 cells (Baron et al. 1997) that contain a chromosomally integrated copy of the CMV-7tetO reporter construct (CMV7tetO-integrated; C, D). Variants V1 to V10 were compared in all three Tet systems (panels A-C) and variants V11 to V18 in the cells with the integrated reporter (panel D). Cells were transfected with the indicated rtTA expression plasmid or pBluescript as a negative control, and a plasmid constitutively expressing Renilla luciferase to correct for differences in transfection efficiency. Cells were cultured in the presence of different dox concentrations (0-1000 ng/ml). The ratio of the firefly and Renilla luciferase activities measured 2 days after transfection reflects the rtTA activity. All values were related to the wild-type (wt) rtTA activity at 1000 ng/ml dox, which was arbitrarily set at 100%. In (C and D), average values of three transfections are shown with error bars indicating the standard deviation.
Figure 3:
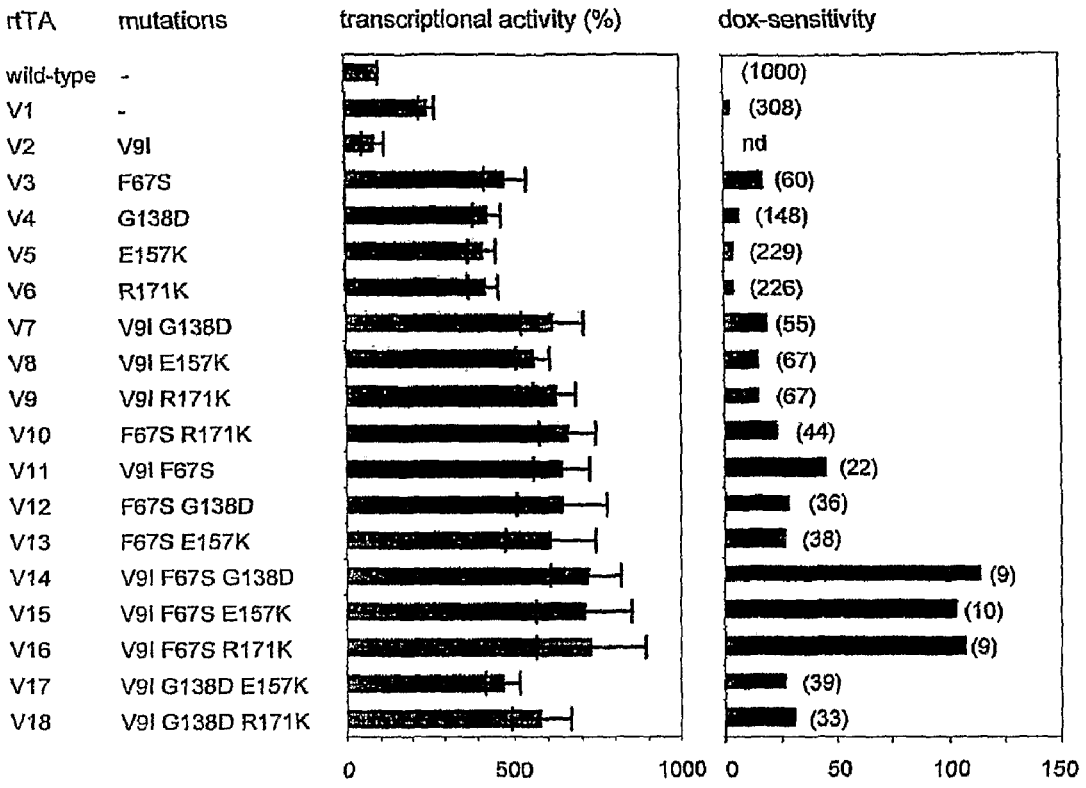
FIG. 3. Transcriptional activity and dox-sensitivity of the naturally evolved and constructed rtTA variants. Transfection assays were performed in HeLa X1/6 cells, see FIG. 2 for details. Transcriptional activity observed at 1000 ng/ml dox is shown as average value of three transfections with error bars indicating the standard deviation. The wild-type rtTA activity was set at 100%. Dox-sensitivity is compared with the wild-type rtTA of which the sensitivity is arbitrarily set at 1. For each rtTA variant, the dox concentration (ng/ml) that results in an activity comparable to that of the wild-type rtTA activity at 1000 ng/ml dox is indicated between brackets. (nd, not determined)
Figure 4:
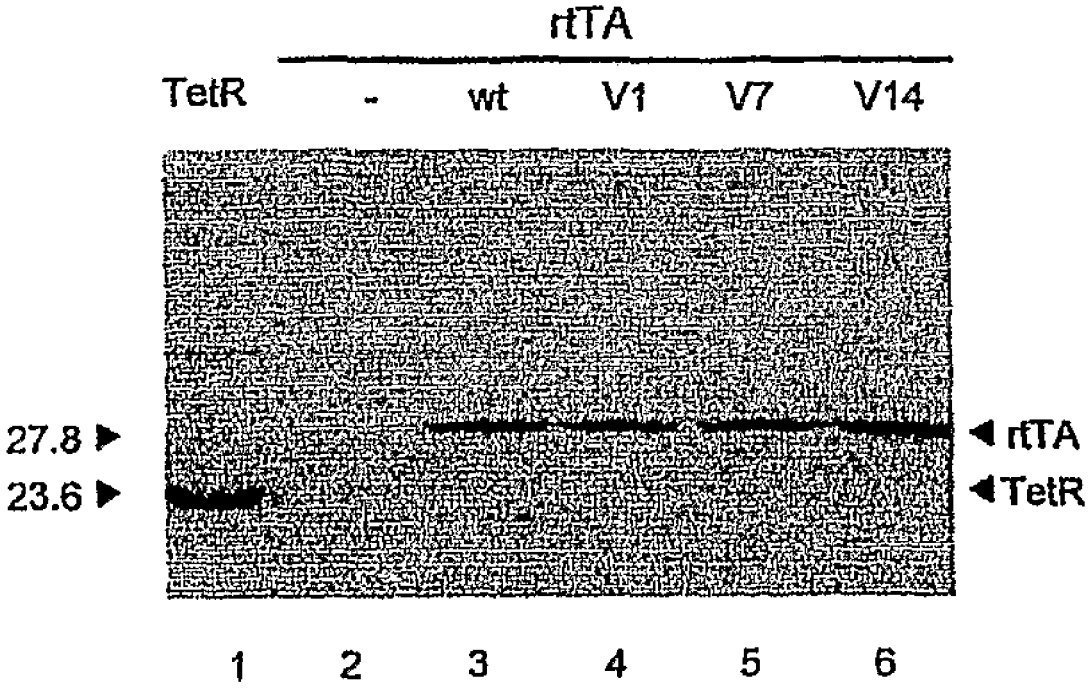
FIG. 4. Mutations do not affect the intracellular rtTA protein level. HeLa X1/6 cells were transfected with the indicated rtTA expression plasmid (lanes 3 to 6) or pBluescript as a negative control (lane 2). Total cellular extracts were prepared at 2 days after transfection and analyzed on Western blot that was stained with polyclonal anti-TetR rabbit serum (Krueger et al. 2003). Detection of purified TetR protein (2 ng) is shown in lane 1. The position and molecular weight (in kDa) of the PTA and TetR proteins are indicated.
Figure 5:
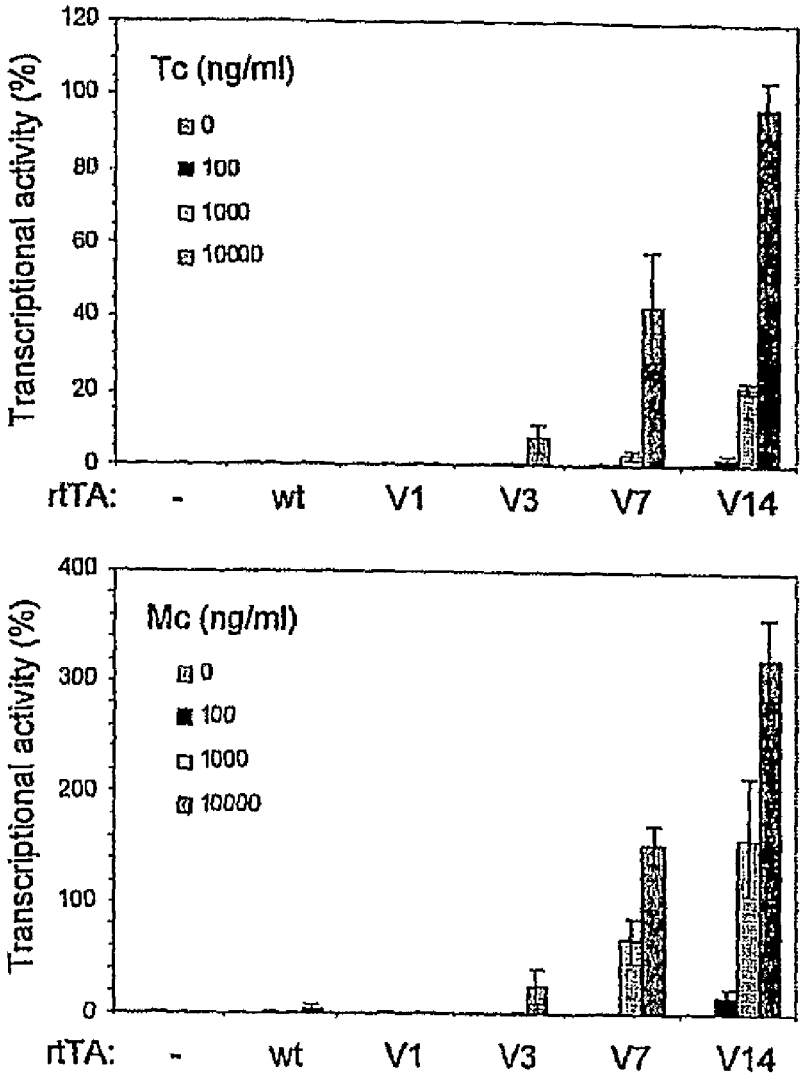
FIG. 5. Novel rtTA variants can be activated by dox-like compounds. The rtTA activity was measured in HeLa X1/6 cells, see FIG. 2 for details. Cells were cultured in the presence of different concentrations of Tc or Mc (0-10000 ng/ml). The wild-type (wt) rtTA activity at 1000 ng/ml dox (not shown) was set at 100%. Average values of three transfections are plotted with error bars indicating the standard deviation.
Figure 6:
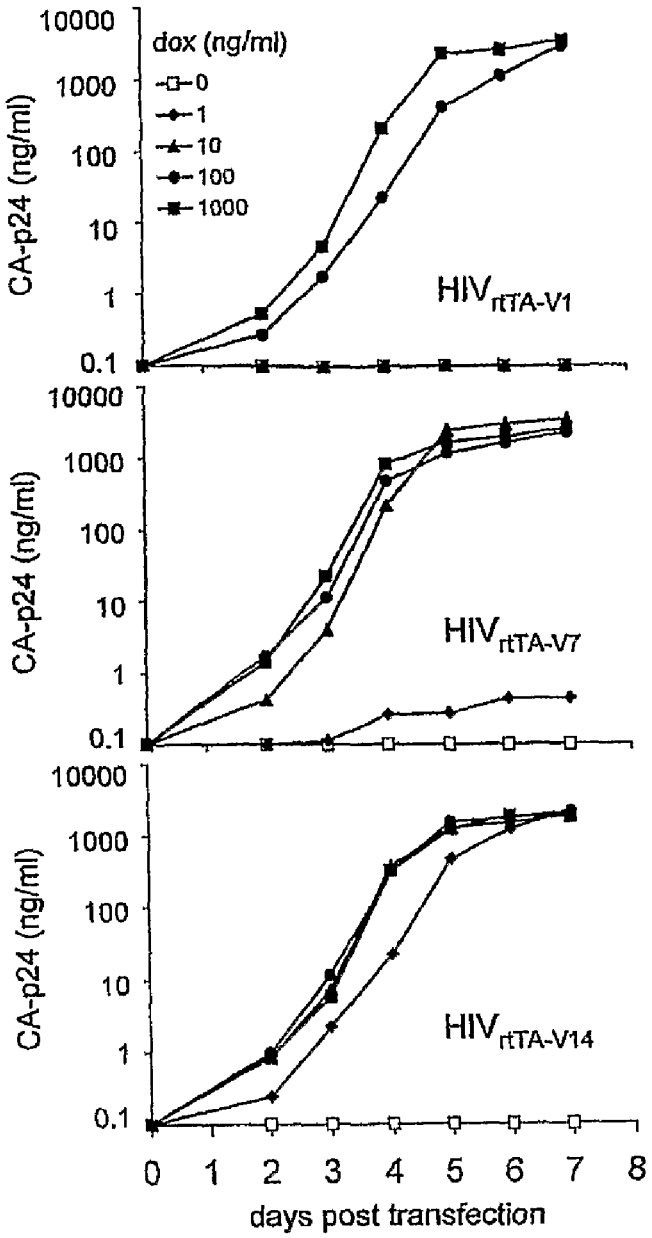
FIG. 6. rtTA variants improve HIV-rtTA replication. The PTA variants V7 and V14 were cloned into the HIV-PTA proviral genome. SupT1 cells were transfected with 5 μg of the molecular clones and cultured in the presence of different dox concentrations (0-1000 ng/ml). Virus replication was monitored by CA-p24 ELISA on culture supernatant samples.
Figure 7:
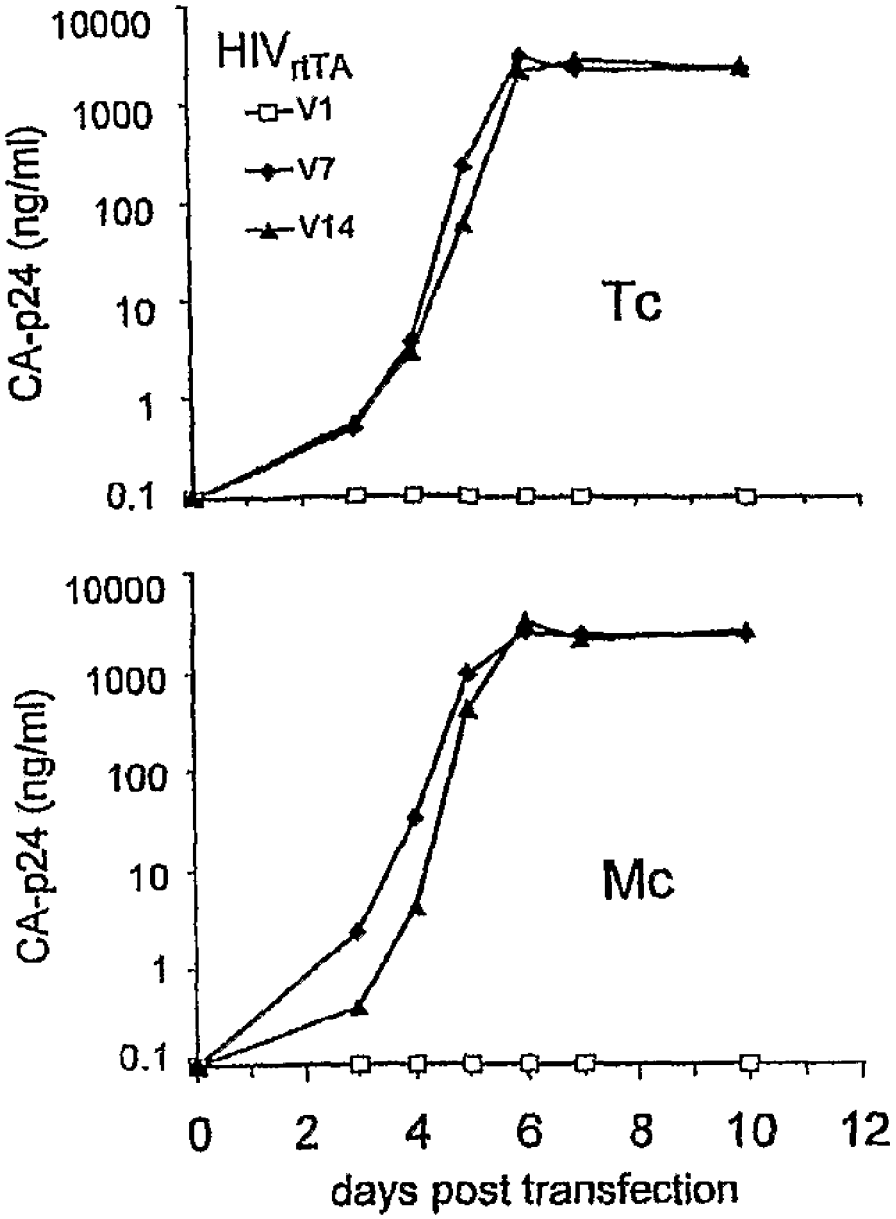
FIG. 7. HIV-rtTA replication induced by dox-like compounds. SupT1 cells were transfected with 5 μg of the HIV-PTA clones and cultured in the presence of 500 ng/ml Tc or Mc. Virus replication was monitored by CA-p24 ELISA on culture supernatant samples.
Figure 8:
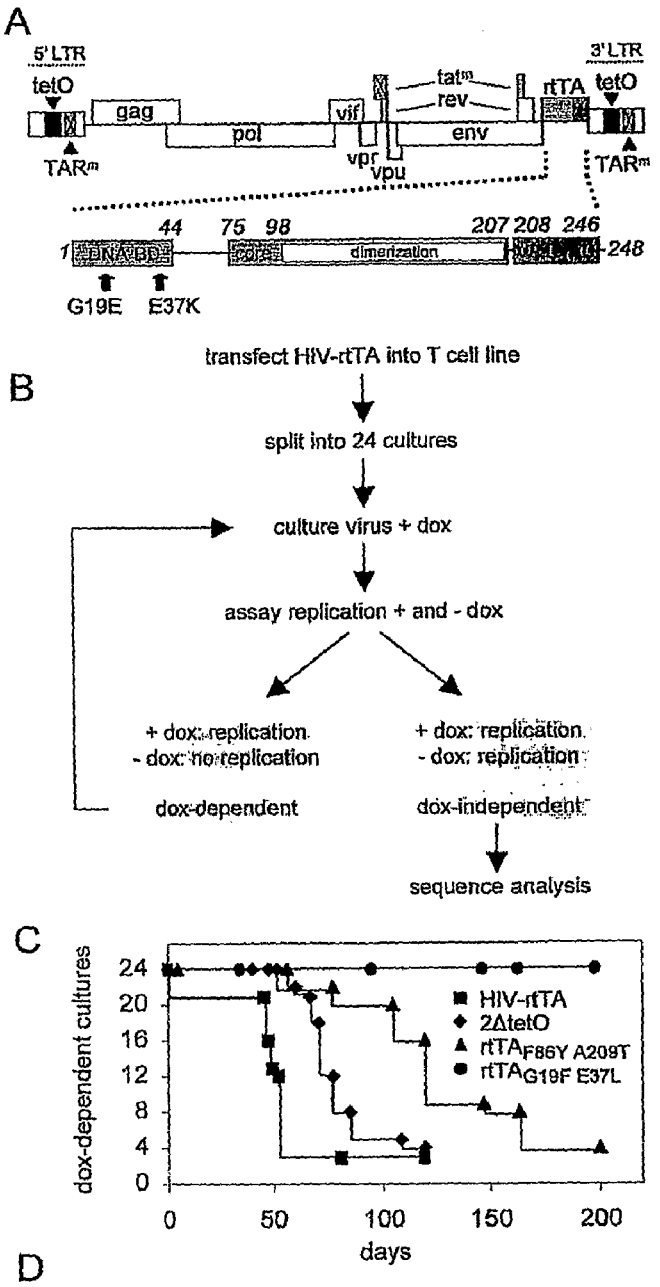
FIG. 8. Evolution of HIV-rtTA can result in loss of dox-control. (A) Schematic of the HIV-PTA genome. The inactivated Tat-TAR elements (crossed boxes) and the introduced rtTA-tetO elements are indicated. rtTA is a fusion protein of the E. coli Tet repressor (TetR) and the VP16 activation domain (AD) of herpes simplex virus. TetR contains a DNA-binding domain (DNA BD) (residues 1-44) and a regulatory core domain (residues 75-207) with a dimerization surface. (B) Flow-chart of the 24-well evolution experiment. Further details are provided in the text. (C) Gradual loss of dox-control in HIV-PTA, HIV-PTA 2ΔtetO (carrying the improved 2ΔtetO promoter configuration (Marzio et al. 2001; Marzio et al. 2002) and HIV-rtTA$_{F86Y\ A209T}$ (carrying the LTR-2ΔtetO promoter and the improved rtTA$_{F86Y\ A209T}$ gene (Das et al. 2004a). The HIV-rtTA$_{G19F\ E37L}$ variant developed in this study does not escape from dox-control. Plotted is the number of dox-dependent cultures as a function of the culture time. Each experiment was started with 24 independent cultures. (D) Amino acid substitutions observed in HIV-rtTA cultures that lost dox-control. In all cases, the G19E substitution resulted from a GGA to G<u>A</u>A codon mutation and the E37K substitution from a <u>G</u>AG to <u>A</u>AG mutation.
Figure 9:
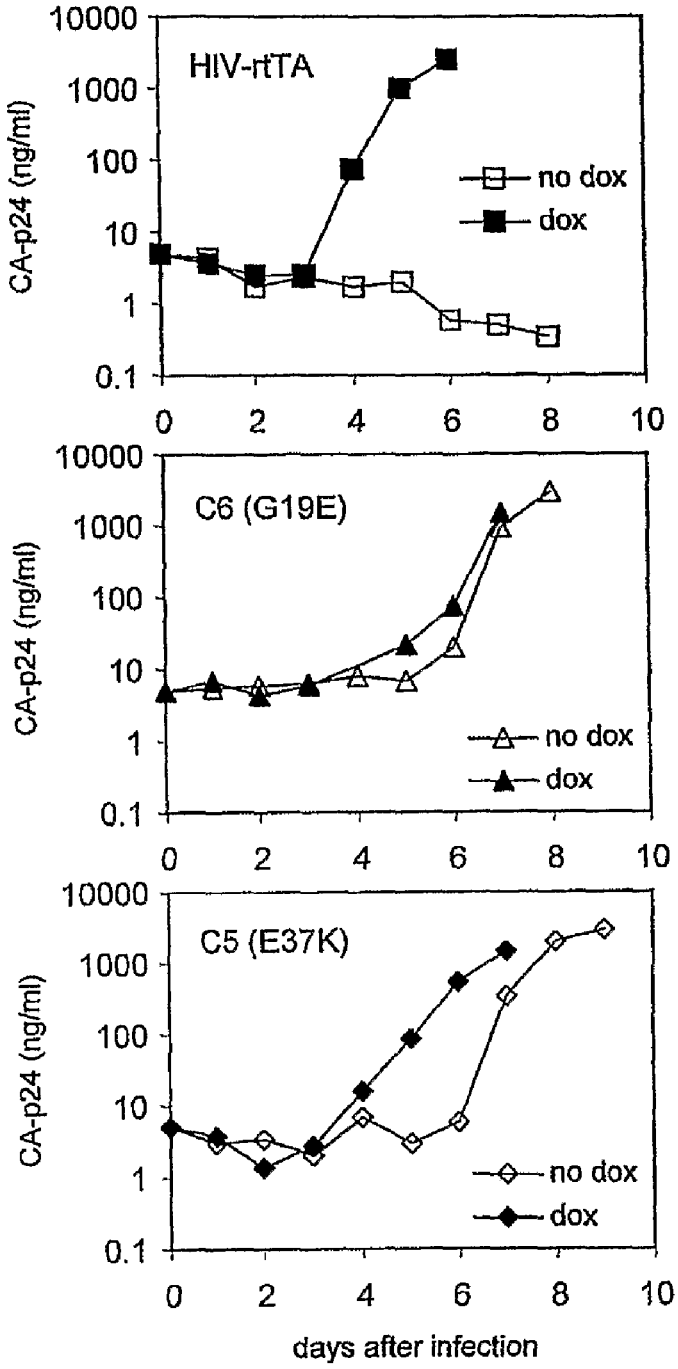
FIG. 9. Replication of evolved HIV-rtTA variants. Replication of the original HIV-rtTA virus, the virus from culture C6 or from culture C5 (both harvested after 50 days of culturing) was compared by infecting SupT1 T cells with equal amounts of virus (5 ng/ml CA-p24) in the absence or presence of dox (1 μg/ml). Sequence analysis revealed that the C6 virus carried the G19E and E 156K mutations in the rtTA gene, and the C5 virus carried the E37K mutation (FIG. 1D).
Figure 10:
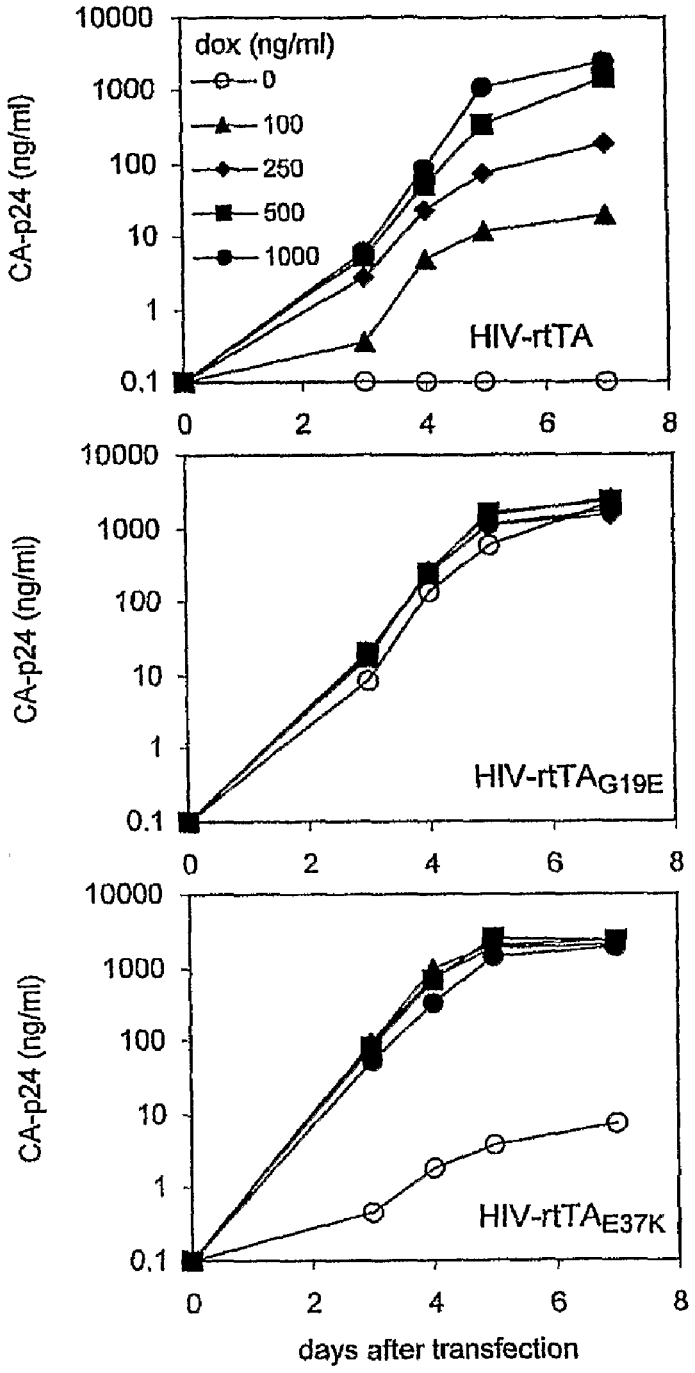
FIG. 10. Amino acid substitutions at rtTA position 19 or 37 confer the loss of dox-control. The G19E and E37K mutated rtTA sequences were cloned into the HIV-rtTA 2ΔtetO proviral genome (Marzio et al. 2001; Marzio et al. 2002). SupT1 cells were transfected with 2.5 μg of the molecular clones and cultured in the presence of 0-1000 ng/ml dox. Virus replication was monitored by CA-p24 ELISA on culture supernatant samples.
Figure 11:
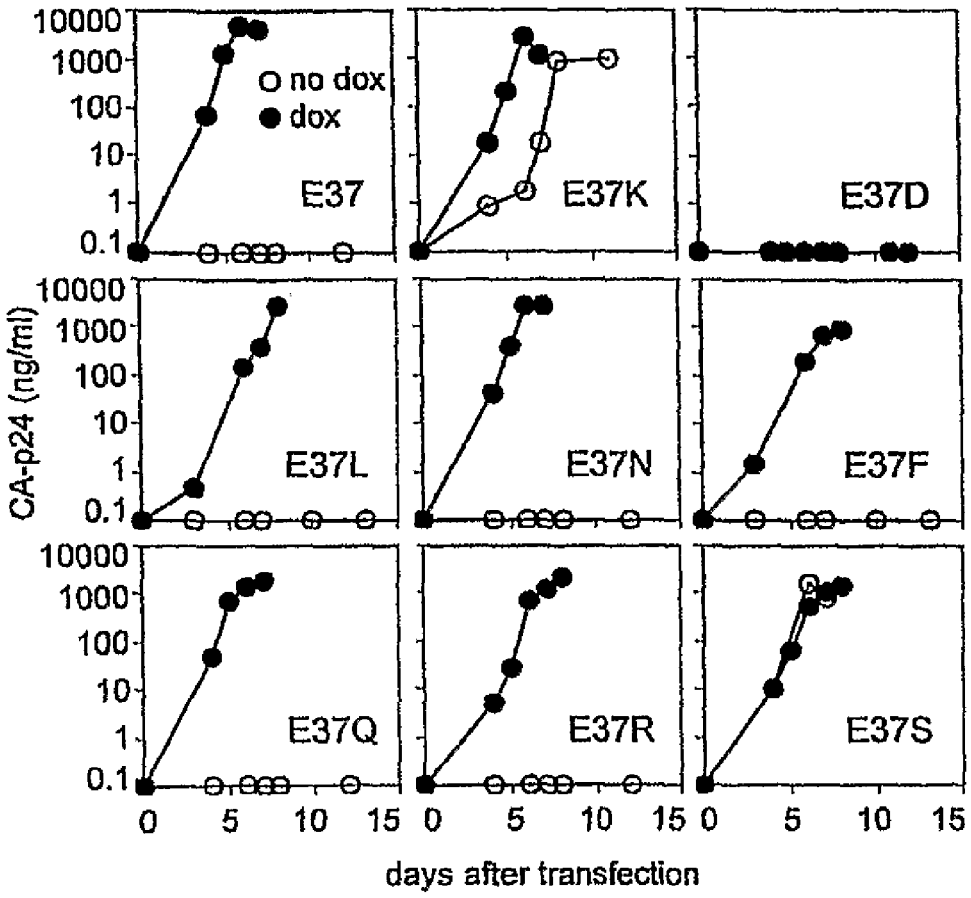
FIG. 11. Replication of HIV-rtTA variants with alternative amino acids at position 37. SupT1 cells were transfected with HIV-rtTA 2ΔtetO proviral plasmids (2.5 μg) carrying the wild-type(E) or an alternative amino acid (K, D, L, N, F, Q, R, S) at rtTA position 37, and cultured with or without 1 μg/ml dox. All viruses, except for the E37K mutant, have the alternative G codon (GGU instead of GGA) at rtTA position 19, which does not affect viral replication (data not shown), and the F86Y and A209T mutations (Das et al. 2004a).
Figure 12:
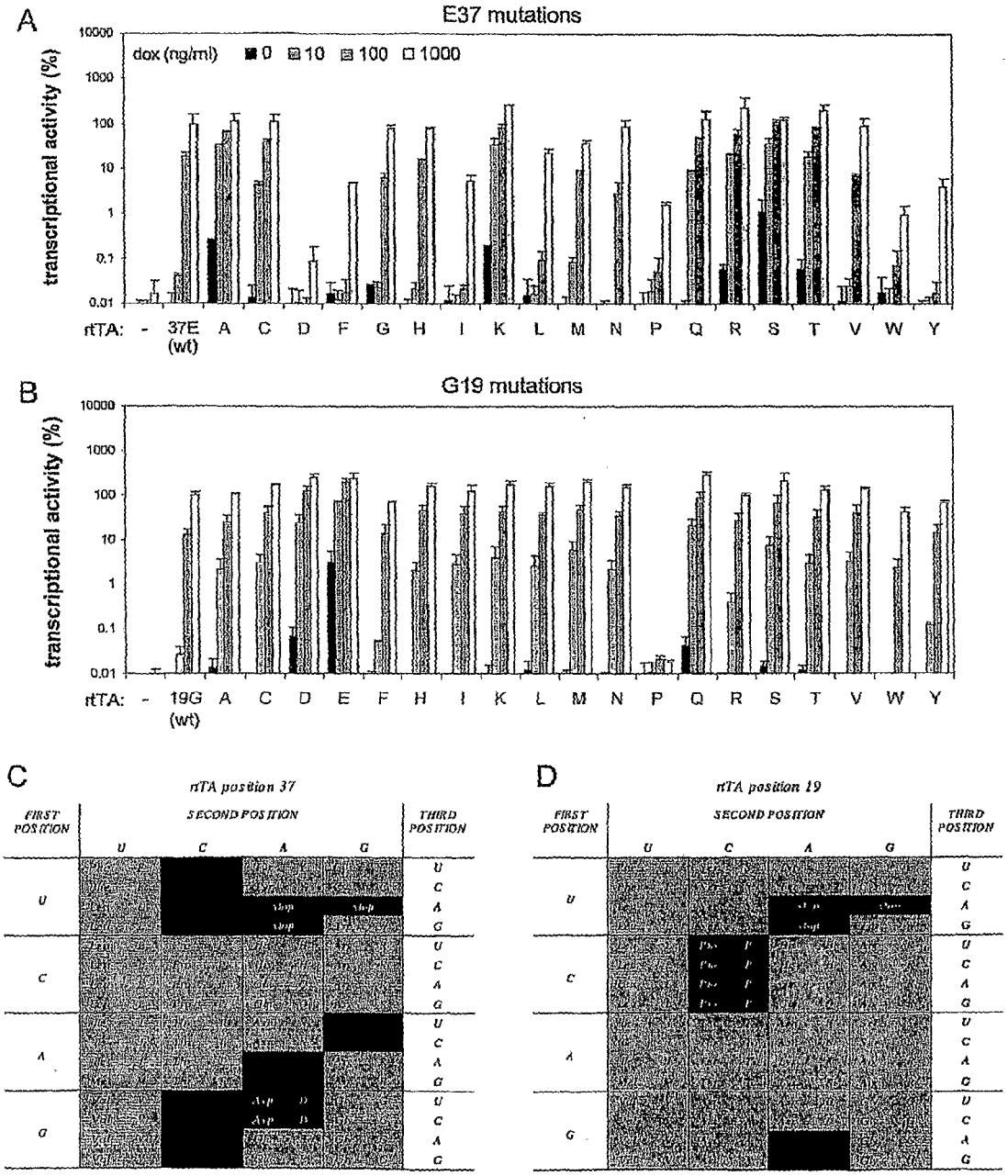
FIG. 12. Transcriptional activity of rtTA variants with alternative amino acids at position 19 or 37. (A and B) rtTA activity was measured in HeLa X1/6 cells (Baronet al. 1997) that contain stably integrated copies of the CMV-7tetO firefly luciferase reporter construct (Gossen et al. 1992). Cells were transfected with the indicated rtTA expression plasmid (all rtTA variants contain the F86Y and A209T mutations that improve rtTA activity (Das et al. 2004a) or pBluescript as a negative control (–), and a plasmid constitutively expressing Renilla luciferase to correct for differences in transfection efficiency. Cells were cultured in the presence of different dox concentrations (0-1000 ng/ml). The ratio of the firefly and Renilla luciferase activities measured two days after transfection reflects rtTA activity. All values were related to the wild-type (37E in A, and 19G in B) rtTA activity at 1000 ng/ml dox, which was arbitrarily set at 100%. Average values of two transfections are plotted with the error bar indicating the standard deviation. (C and D) Codon tables of rtTA variants with all possible amino acids at position 19 or 37. The dox-dependent phenotype is marked in light grey, variants active in the absence of dox in dark grey, and inactive variants in black. See the text for details.
Figure 13:
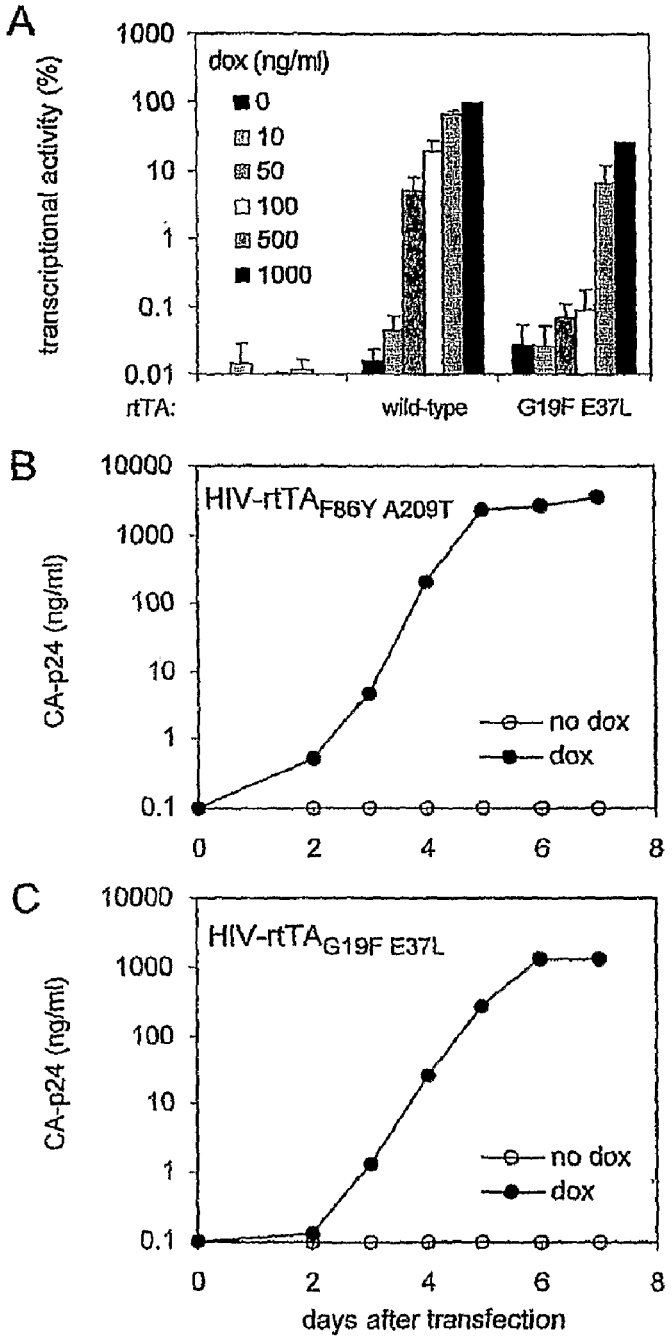
FIG. 13. Activity of the novel rtTA variant with safety-lock mutations. (A) The activity of wild-type and safety-lock rtTA (G19F E37L) was measured in HeLa X1/6 cells, see FIG. 5 for details. Cells were cultured in the presence of different dox concentrations (0-1000 ng/ml). All values were related to the wild-type rtTA activity at 1000 ng/ml dox, which was arbitrarily set at 100%. Average values of two transfections are plotted with the error bar indicating the standard deviation. (B and C) Replication of HIV-rtTA$_{F86Y\ A209T}$ and HIV-rtTA$_{G19F\ E37L}$ (which also carries the F86Y and A209T mutations (Das et al. 2004a). SupT1 cells were transfected with 5 μg of the molecular clones and cultured with or without 1 μg/ml dox. Virus replication was monitored by CA-p24 ELISA on culture supernatant samples.
Figure 17:
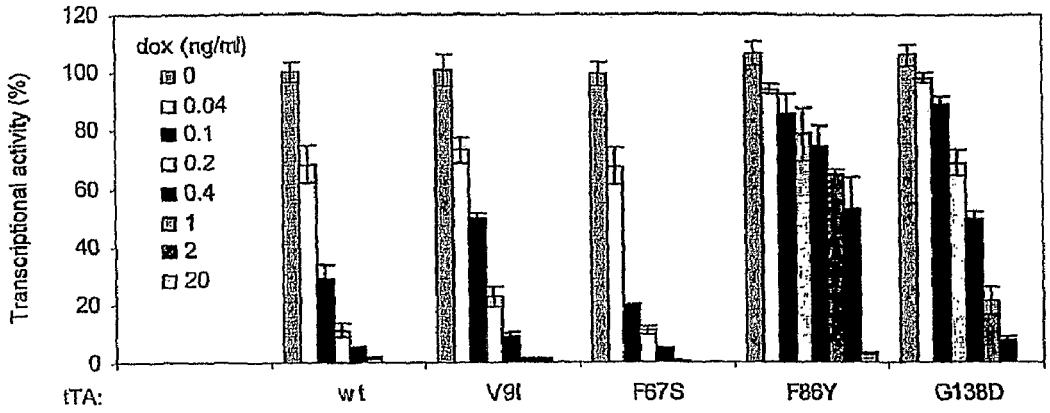
FIG. 17. Mutations that enhance rtTA activity do not improve tTA activity. The transcriptional activity of tTA variants was measured in HeLa X1/6 cells (Baron et al. 1997) containing chromosomally integrated copies of the CMV-7tetO luciferase reporter construct. Cells were transfected with the indicated tTA expression plasmids or pBluescript (–) as a negative control and a plasmid constitutively expressing Renilla luciferase to correct for differences in transfection efficiency. Cells were cultured in the presence of different dox concentrations (0-20 ng/ml). The ratio of the firefly and Renilla luciferase activities measured two days after transfection reflects the tTA activity. All values were related to the original (wild-type) tTA activity in the absence of dox, which was arbitrarily set at 100%. Average values of two transfections are shown with the error bar indicating the standard deviation.
Figure 18:
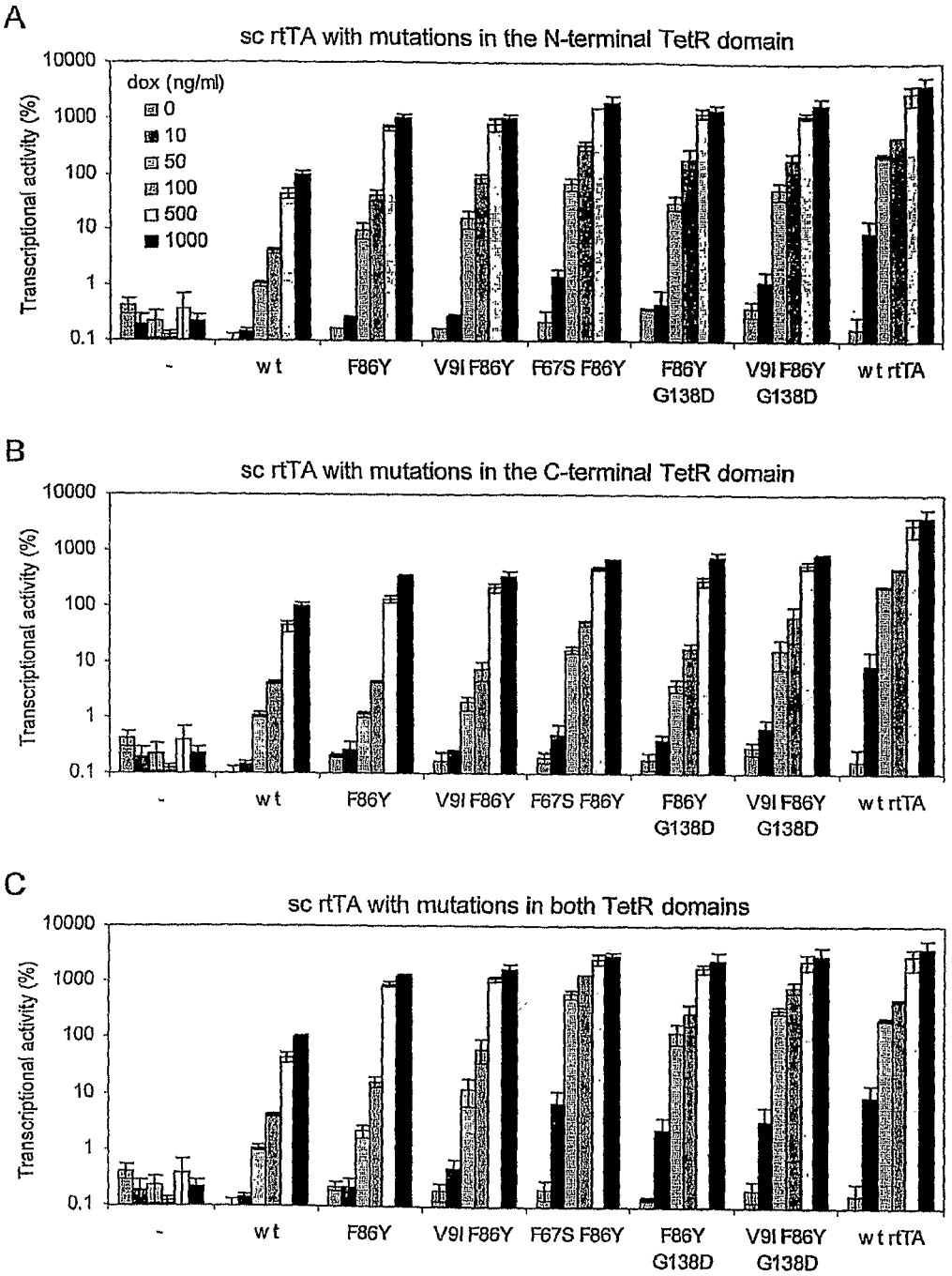
FIG. 18. Mutations observed in rtTA can improve sc rtTA activity. The transcriptional activity of rtTA and sc rtTA was measured in HeLa X1/6 cells, see FIG. 17 for details. Cells were cultured in the presence of different dox concentrations (0-1000 ng/ml). All values were related to the original (wild-type) sc rtTA activity at 1000 ng/ml dox, which was arbitrarily set at 100%. Average values of two transfections are plotted with the error bar indicating the standard deviation.
Figure 20:
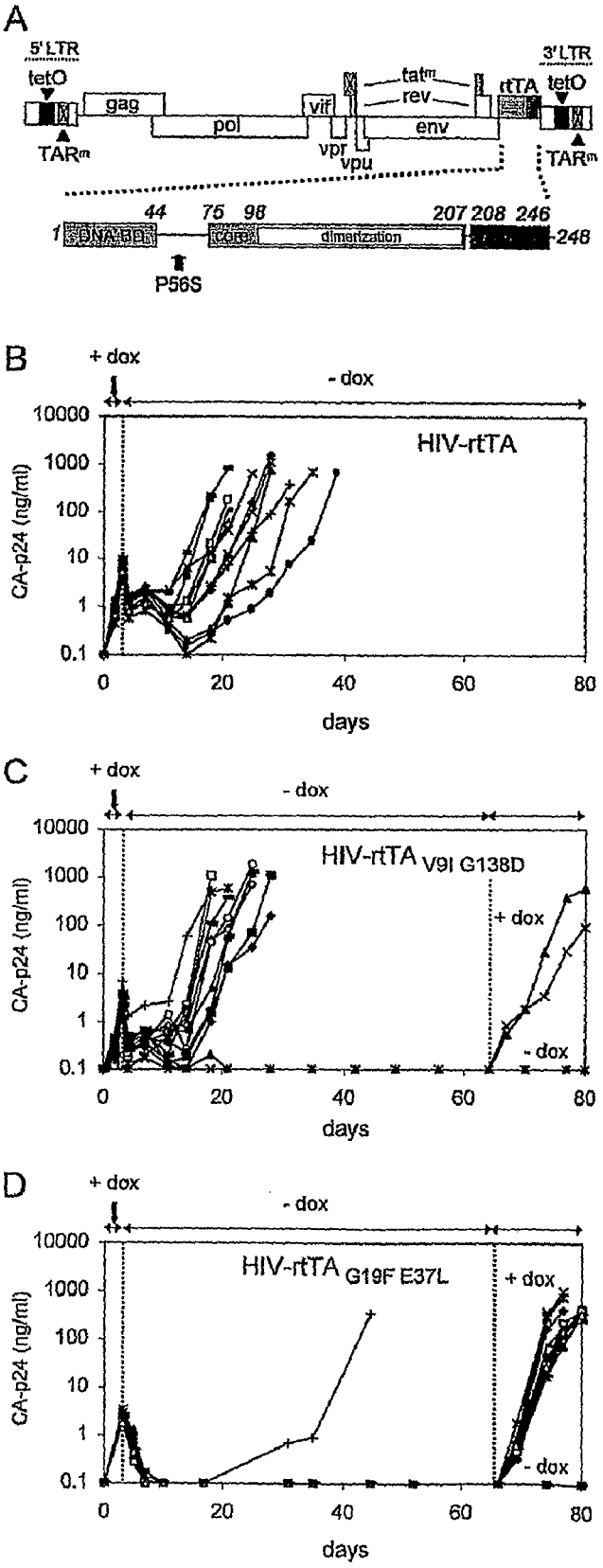
FIG. 20. Evolution of HIV-rtTA after transient dox administration. (A) Schematic of the HIV-rtTA genome. The inactivated Tat-TAR elements (crossed boxes) and the introduced rtTA-tetO elements are indicated. rtTA is a fusion protein of the E. coli Tet repressor (TetR) and the VP16 activation domain (AD) of herpes simplex virus. TetR contains a DNA-binding domain (DNA BD) (amino acids 1-44) and a regulatory core domain (amino acids 75-207) with a dimerization surface. (B-D) Loss of dox-control in cultures of HIVrtTA after transient activation. SupT1 cells were transfected with HIV-rtTA and cultured at 100 ng/ml dox (B), HIV-rtTA$_{V9I\ G138D}$ at 10 ng/ml dox (C), or HIV-rtTA$_{G19F\ E37L}$ at 1000 ng/ml dox (D). Each experiment was started with 12 independent cultures (different symbols represent different cultures). At day 3, dox was washed out and the cultures were continued with dox-free medium. The cultures in which the virus did not lose dox-control were split in two parts at day 64 (C) or day 66 (D) and dox was added to one of the samples. Virus production was monitored by CA-p24 ELISA on culture supernatant samples.
Figure 21:
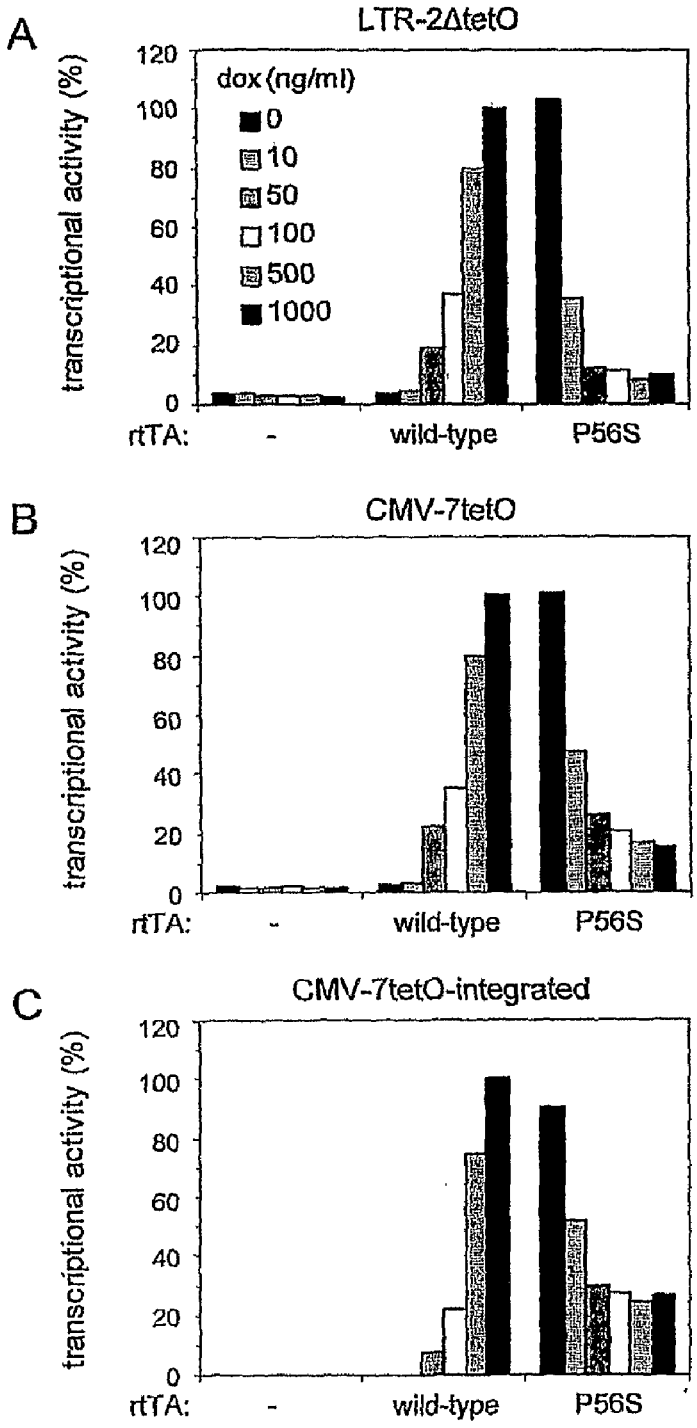
FIG. 21. The P56S mutation causes a tTA-like phenotype. The activity of wild-type and P56S-mutated rtTA was measured in C33A cells transfected with a reporter plasmid carrying the firefly luciferase gene under the control of the viral LTR-2ΔtetO promoter (LTR-2ΔtetO; A) or under the control of a minimal CMV promoter coupled to an array of seven tetO elements (CMV7tetO; B). Furthermore, rtTA activity was measured in HeLa X1/6 cells (Baron et al. 1997) that contain chromosomally integrated copies of the CMV-7tetO luciferase construct (CMV-7tetO-integrated; C). Cells were transfected with the indicated rtTA expression plasmid (both rtTA variants carry the F86Y and A209T mutations (Das et al. 2004a) or pBluescript as a negative control (−), and a plasmid constitutively expressing Renilla luciferase to correct for differences in transfection efficiency. Cells were cultured with different dox concentrations (0-1000 ng/ml). The ratio of the firefly and Renilla luciferase activities measured two days after transfection reflects the rtTA activity. All values were related to the wild-type rtTA activity at 1000 ng/ml dox, which was arbitrarily set at 100%.
Figure 23:
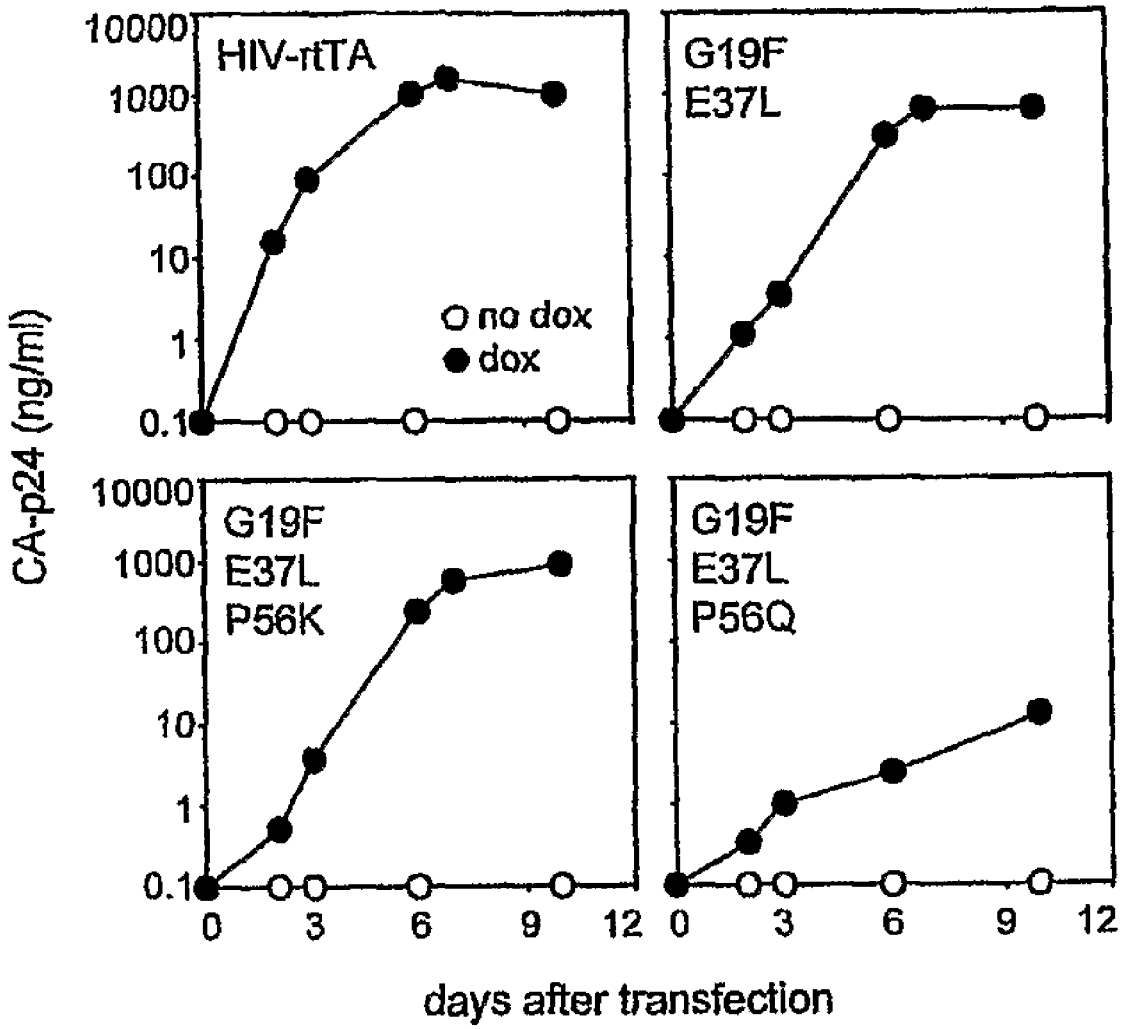
FIG. 23. Replication of HIV-$rtTA_{G19F\ E37L}$ variants with different amino acids at position 56. SupT1 cells were transfected with 5 μg of HIV-rtTA molecular clones encoding different rtTA alleles, and cultured with or without 1 μg/ml dox. All rtTA variants contain the F86Y and A209T mutations. Virus replication was monitored by CA-p24 ELISA on culture supernatant samples.
Figure 24:
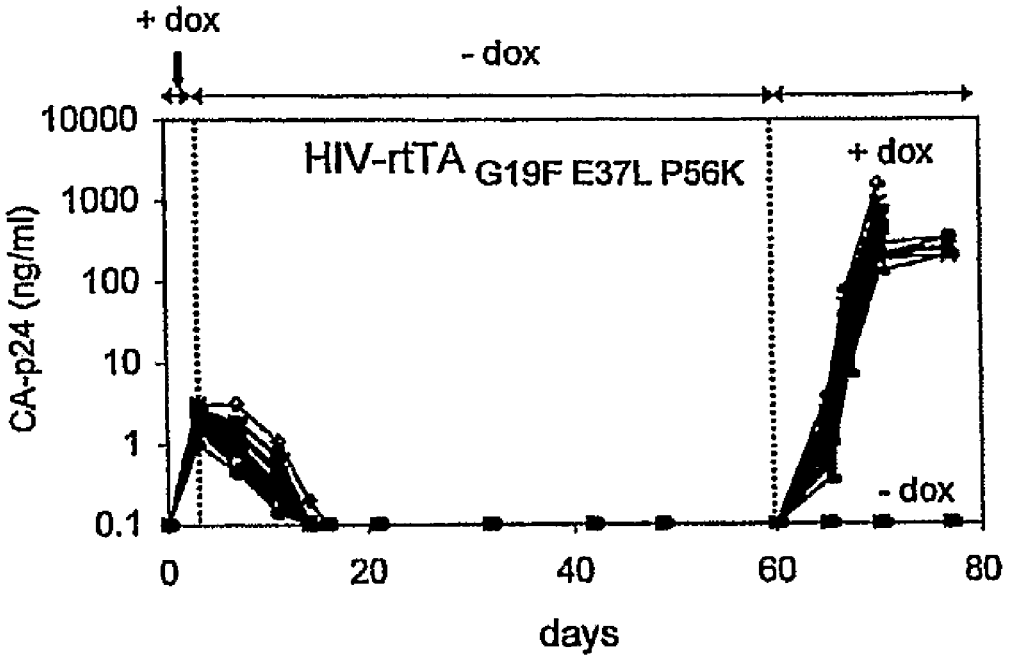
FIG. 24. Blocking the loss of dox-control by triple safety-lock mutations. SupT1 cells were transfected with HIV-rtTA containing triple safety-lock mutations (HIV-$rtTA_{G19F\ E37L\ P56K}$) at 1000 ng/ml dox and split into 24 independent cultures (different symbols represent different cultures). At day 3, dox was washed out and the cultures were continued with dox-free medium. At day 60, all cultures were split in two parts and dox (1000 ng/ml) was added to one of the samples. Virus production was monitored by CA-p24 ELISA on culture supernatant samples.

Akagi K, Kanai M, Saya H, Kozu T, Berns A. A novel tetracycline-dependent transactivator with E2F4 transcriptional activation domain. Nucleic Acids Res. 2001 Feb. 15; 29 (4):E23

Auersperg, N. (1964). Long-term cultivation of hypodiploid human tumor cells. J. Natl. Cancer Inst. 32: 135-163.

Back, N. K., M. Nijhuis, W. Keulen, C. A. Boucher, B. O. Oude Essink, A. B. van Kuilenburg, A. H. van Gennip, and B. Berkhout. 1996. Reduced replication of 3TC-resistant HIV-1 variants in primary cells due to a processivity defect of the reverse transcriptase enzyme. EMBO J. 15:4040-4049.

Baron, U., Gossen, M., and Bujard, H. (1997). Tetracycline-controlled transcription in eukaryotes: novel transactivators with graded transactivation potential. Nucleic Acids Res. 25: 2723-2729.

Baron, U., Schnappinger, D., Helbl, V., Gossen, M., Hillen, W., and Bujard, H. (1999). Generation of conditional mutants in higher eukaryotes by switching between the expression of two genes. Proc. Natl. Acad. Sci. USA 96: 1013-1018.

Baron, U., and Bujard, H. (2000). Tet repressor-based system for regulated gene expression in eukaryotic cells: principles and advances. Methods Enzymol. 327: 401-421.

Berens, C., and Hillen, W. (2003). Gene regulation by tetracyclines. Constraints of resistance regulation in bacteria shape TetR for application in eukaryotes. Eur. J. Biochem. 270: 3109-3121.

Berkhout B, Das A T, Beerens N (2001) HIV-1 RNA editing, hypermutation, and error-prone reverse transcription. Science 292: 7.

Berkhout B and de Ronde A (2004) APOBEC3G versus reverse transcriptase in the generation of HIV-1 drug-resistance mutations. AIDS 18: 1861-1863.

Das, A. T., Klaver, B., Klasens, B. I., van Wamel, J. L., and Berkhout, B. (1997). A conserved hairpin motif in the R-U5 region of the human immunodeficiency virus type 1 RNA genome is essential for replication. J. Virol. 71: 2346-2356

Das, A. T., Klaver, B., and Berkhout, B. (1999). A hairpin structure in the R region of the human immunodeficiency virus type 1 RNA genome is instrumental in polyadenylation site selection. J. Virol. 73: 81-91

Das, A. T., et al. (2004a). Viral evolution as a tool to improve the tetracycline-regulated gene expression system. J. Biol. Chem. 279: 18776-18782.

Das, A. T., Verhoef, K., and Berkhout, B. (2004b). A conditionally replicating virus as a novel approach toward an HIV vaccine. Methods Enzymol. 388: 359-379.

Deuschle, U., W. K. Meyer, and H. J. Thiesen. 1995. Tetracycline-reversible silencing of eukaryotic promoters. Mol Cell Biol 15:1907-1914.

Forster, K., V. Helbl, T. Lederer, S. Urlinger, N. Wittenburg, and W. Hillen. 1999. Tetracycline-inducible expression systems with reduced basal activity in mammalian cells. Nucleic Acids Res. 27:708-710.

Freundlieb, S., C. Schirra-Muller, and H. Bujard. 1999. A tetracycline controlled activation/repression system with increased potential for gene transfer into mammalian cells. J. Gene Med. 1:4-12.

Gossen, M., and Bujard, H. (1992). Tight control of gene expression in mammalian cells by tetracycline-responsive promoters. Proc. Natl. Acad. Sci. USA 89: 5547-5551.

Gossen, M., Freundlieb, S., Bender, G., Muller, G., Hillen, W., and Bujard, H. (1995). Transcriptional activation by tetracyclines in mammalian cells. Science 268: 1766-1769.

Gossen, M., and Bujard, H. (2001). Tetracyclines in the control of gene expression in eukaryotes. In Tetracyclines in biology, chemistry and medicine (M. Nelson, W. Hillen, and R. A. Greenwald, Eds.), pp. 139-157. Birkhäuser Verlag, Basel.

Helbl, V. and W. Hillen. 1998. Stepwise selection of TetR variants recognizing tet operator 4C with high affinity and specificity. J. Mol. Biol. 276:313-318.

Helbl, V., B. Tiebel, and W. Hillen. 1998. Stepwise selection of TetR variants recognizing tet operator 6C with high affinity and specificity. J. Mol. Biol. 276:319-324.

Henssler, E. M., O, Scholz, S. Lochner, P. Gmeiner, and W. Hillen. 2004. Structure-based design of Tet repressor to optimize a new inducer specificity. Biochemistry 43:9512-9518.

Hinrichs, W., et al. (1994). Structure of the Tet repressor-tetracycline complex and regulation of antibiotic resistance. Science 264: 418-420.

Kamper M R, Gohla G, Schluter G. A novel positive tetracycline-dependent transactivator (rtTA) variant with reduced background activity and enhanced activation potential. FEBS Lett. 2002 Apr. 24; 517 (1-3):115-20

Keulen W, Back N K, van Wijk A, Boucher C A, Berkhout B (1997) Initial appearance of the 184Ile variant in lamivudine-treated patients is caused by the mutational bias of human immunodeficiency virus type 1 reverse transcriptase. J. Virol 71: 3346-3350.

Keulen W, Boucher C, Berkhout B (1996) Nucleotide substitution patterns can predict the requirements for drug-resistance of HIV-1 proteins. Antiviral Res 31: 45-57.

Kisker, C., Hinrichs, W., Tovar, K., Hillen, W., and Saenger, W. (1995). The complex formed between Tet repressor and tetracycline-Mg2+ reveals mechanism of antibiotic resistance. J. Mol. Biol. 247: 260-280

Kraulis, P. J. (1991). MOLSCRIPT: a program to produce both detailed and schematic plots of protein structures. J. Appl. Crystallogr. 24: 946-950

Krueger, C., Berens, C., Schmidt, A., Schnappinger, D., and Hillen, W. (2003). Single-chain Tet transregulators. Nucleic Acids Research Vol. 31 No. 12: 3050-3056.

Krueger, C., A. Schmidt, C. Danke, W. Hillen, and C. Berens. 2004. Transactivator mutants with altered effector specificity allow selective regulation of two genes by tetracycline variants. Gene 331:125-131.

Marzio, G., Verhoef, K., Vink, M., and Berkhout, B. (2001). In vitro evolution of a highly replicating, doxycycline-dependent HIV for applications in vaccine studies. Proc. Natl. Acad. Sci. USA 98: 6342-6347.

Marzio, G., M. Vink, K. Verhoef, A. de Ronde, and B. Berkhout. 2002. Efficient human immunodeficiency virus replication requires a fine-tuned level of transcription. J. Virol. 76:3084-3088.

Merritt, E. A., and Bacon, D. J. (1997). Raster3D: Photo-realistic molecular graphics. Methods Enzymol. 277: 505-524

Mikaelian, I., and Sergeant, A. (1992). A general and fast method to generate multiple site directed mutations. Nucleic Acids Res. 20: 376

Peden, K., M. Emerman, and L. Montagnier. 1991. Changes in growth properties on passage in tissue culture of viruses derived from infectious molecular clones of HIV-1LAI, HIV-1MAL, and HIV-1ELI. Virology 185:661-672.

Scholz, O., M. Kostner, M. Reich, S. Gastiger, and W. Hillen. 2003. Teaching TetR to recognize a new inducer. J. Mol. Biol. 329:217-227.

Smith, S. D., Shatsky, M., Cohen, P. S., Warnke, R., Link, M. P., and Glader, B. E. (1984). Monoclonal antibody and enzymatic profiles of human malignant T-lymphoid cells and derived cell lines. Cancer Res. 44: 5657-5660.

Urlinger, S., Baron, U., Thellmann, M , Hasan, M. T., Bujard, H., and Hillen, W. (2000). Exploring the sequence space for tetracycline-dependent transcriptional activators: novel mutations yield expanded range and sensitivity. Proc. Natl. Acad. Sci, USA 97 (14): 7963-7968.

Verhoef, K., G. Marzio, W. Hillen, H. Bujard, and B. Berkhout. 2001. Strict control of human immunodeficiency virus type 1 replication by a genetic switch: Tet for Tat. J. Virol. 75:979-987.

SEQUENCE LISTING

```
<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Primer tTA1

<400> SEQUENCE: 1

acagccatag cagtagctga g                                                21


<210> SEQ ID NO 2
<211> LENGTH: 23
<212> TYPE: DNA
<213> ORGANISM: Artificial Sequence
<220> FEATURE:
<223> OTHER INFORMATION: Primer tTA rev2

<400> SEQUENCE: 2

gatcaaggat atcttgtctt cgt                                              23


<210> SEQ ID NO 3
<211> LENGTH: 29
<212> TYPE: DNA
<213> ORGANISM: Artificial Sequence
<220> FEATURE:
<223> OTHER INFORMATION: Primer M tTA F67S

<400> SEQUENCE: 3

catacccact cctgcccccct ggaaggcga                                       29


<210> SEQ ID NO 4
<211> LENGTH: 29
```

<212> TYPE: DNA
<213> ORGANISM: Artificial Sequence
<220> FEATURE:
<223> OTHER INFORMATION: Primer tTA G138D

<400> SEQUENCE: 4 gtccgccgtg gaccacttta cactgggct 29

<210> SEQ ID NO 5
<211> LENGTH: 19
<212> TYPE: DNA
<213> ORGANISM: Artificial Sequence
<220> FEATURE:
<223> OTHER INFORMATION: Primer 1

<400> SEQUENCE: 5 tggagacgcc atccacgct 19

<210> SEQ ID NO 6
<211> LENGTH: 30
<212> TYPE: DNA
<213> ORGANISM: Artificial Sequence
<220> FEATURE:
<223> OTHER INFORMATION: Primer 2

<400> SEQUENCE: 6 tgaaatcgag tttctccagg ccacatatga 30

<210> SEQ ID NO 7
<211> LENGTH: 21
<212> TYPE: DNA
<213> ORGANISM: Artificial Sequence
<220> FEATURE:
<223> OTHER INFORMATION: Primer 3

<400> SEQUENCE: 7 tcactgcatt ctagttgtgg t 21

<210> SEQ ID NO 8
<211> LENGTH: 30
<212> TYPE: DNA
<213> ORGANISM: Artificial Sequence
<220> FEATURE:
<223> OTHER INFORMATION: Primer KV1

<400> SEQUENCE: 8 ccatcgatac cgtcgacata gcagaatagg 30

<210> SEQ ID NO 9
<211> LENGTH: 30
<212> TYPE: DNA
<213> ORGANISM: Artificial Sequence
<220> FEATURE:
<223> OTHER INFORMATION: Primer 3'TAT

<400> SEQUENCE: 9 cgggaattct tactgctttg atagagaaac 30

<210> SEQ ID NO 10
<211> LENGTH: 24
<212> TYPE: DNA
<213> ORGANISM: Artificial Sequence
<220> FEATURE:
<223> OTHER INFORMATION: Primer tTA-tet01

<400> SEQUENCE: 10 ctccccgggt aactaagtaa ggat 24

<210> SEQ ID NO 11
<211> LENGTH: 29
<212> TYPE: DNA
<213> ORGANISM: Artificial Sequence
<220> FEATURE:
<223> OTHER INFORMATION: Primer c(N1)

<400> SEQUENCE: 11 ggtctgaggg atctctagtt accagagtc 29

<210> SEQ ID NO 12
<211> LENGTH: 98
<212> TYPE: DNA
<213> ORGANISM: Artificial Sequence
<220> FEATURE:
<223> OTHER INFORMATION: Oligonucleotide G19

<400> SEQUENCE: 12 ataaccatgt ctagactgga caagagcaaa gtcataaact ctgctctgga attactcaat 60 ggtgtcggta tcgaaggcct gacgacaagg aaactcgc 98

<210> SEQ ID NO 13
<211> LENGTH: 91
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (45)..(47)
<223> OTHER INFORMATION: ATC, GAA, AAG, ATT, CTG, GCG or AGA

<400> SEQUENCE: 13 agcagggccc gcttgttctt cacgtgccag tacagggtag gctgctcaac tcccagcttt 60 tgagcgagtt tccttgtcgt caggccttcg a 91

<210> SEQ ID NO 14
<211> LENGTH: 85
<212> TYPE: DNA
<213> ORGANISM: Artificial Sequence
<220> FEATURE:
<223> OTHER INFORMATION: Primer Random rtTA-19
<220> FEATURE:
<221> NAME/KEY: variation
<222> LOCATION: (61)..(62)
<223> OTHER INFORMATION: a, c or g

<400> SEQUENCE: 14 ttcaccatgt ctagactgga caagagcaaa gtcataaact ctgctctgga attactcaat 60 ttkgtcggta tcgaaggcct gacga 85

<210> SEQ ID NO 15
<211> LENGTH: 21
<212> TYPE: DNA
<213> ORGANISM: Artificial Sequence
<220> FEATURE:
<223> OTHER INFORMATION: Primer CMV2

<400> SEQUENCE: 15 tcactgcatt ctagttgtgg t 21

<210> SEQ ID NO 16
<211> LENGTH: 19

<212> TYPE: DNA
<213> ORGANISM: Artificial Sequence
<220> FEATURE:
<223> OTHER INFORMATION: Primer CMV1

<400> SEQUENCE: 16 tggagacgcc atccacgct 19

<210> SEQ ID NO 17
<211> LENGTH: 67
<212> TYPE: DNA
<213> ORGANISM: Artificial Sequence
<220> FEATURE:
<223> OTHER INFORMATION: Primer random rtTA 37
<220> FEATURE:
<221> NAME/KEY: variation
<222> LOCATION: (46)..(47)
<223> OTHER INFORMATION: c, a or g

<400> SEQUENCE: 17 agcagggccc gcttgttctt cacgtgccag tacagggtag gctgmttaac tcccagcttt 60 tgagcga 67

<210> SEQ ID NO 18
<211> LENGTH: 45
<212> TYPE: DNA
<213> ORGANISM: Artificial Sequence
<220> FEATURE:
<223> OTHER INFORMATION: primer M scrtTA-V9I

<400> SEQUENCE: 18 ggctctagat ctcgtttaga taaaagtaaa atcattaaca gcgca 45

<210> SEQ ID NO 19
<211> LENGTH: 27
<212> TYPE: DNA
<213> ORGANISM: Artificial Sequence
<220> FEATURE:
<223> OTHER INFORMATION: Primer scrtTA-F67S

<400> SEQUENCE: 19 aggcaccata ctcactcttg cccttta 27

<210> SEQ ID NO 20
<211> LENGTH: 24
<212> TYPE: DNA
<213> ORGANISM: Artificial Sequence
<220> FEATURE:
<223> OTHER INFORMATION: Primer scrtTA-F86Y

<400> SEQUENCE: 20 aacgctaaaa gttatagatg tgct 24

<210> SEQ ID NO 21
<211> LENGTH: 25
<212> TYPE: DNA
<213> ORGANISM: Artificial Sequence
<220> FEATURE:
<223> OTHER INFORMATION: Primer scrtTA-G138D

<400> SEQUENCE: 21 cagcgctgtg gaccacttta cttta 25

<210> SEQ ID NO 22
<211> LENGTH: 22
<212> TYPE: DNA

<213> ORGANISM: Artificial Sequence
<220> FEATURE:
<223> OTHER INFORMATION: Primer 1 (page 59)

<400> SEQUENCE: 22 taatcatatg tggcctggag aa 22

<210> SEQ ID NO 23
<211> LENGTH: 31
<212> TYPE: DNA
<213> ORGANISM: Artificial Sequence
<220> FEATURE:
<223> OTHER INFORMATION: Primer 2 (page 59)

<400> SEQUENCE: 23 aggcgtattg atcaattcaa ggccgaataa g 31

<210> SEQ ID NO 24
<211> LENGTH: 21
<212> TYPE: DNA
<213> ORGANISM: Artificial Sequence
<220> FEATURE:
<223> OTHER INFORMATION: Primer 3 (page 59)

<400> SEQUENCE: 24 tcactgcatt ctagttgtgg t 21

<210> SEQ ID NO 25
<211> LENGTH: 46
<212> TYPE: DNA
<213> ORGANISM: Artificial Sequence
<220> FEATURE:
<223> OTHER INFORMATION: Primer rtTA-56
<220> FEATURE:
<221> NAME/KEY: variation
<222> LOCATION: (25)..(26)
<223> OTHER INFORMATION: a, c or g

<400> SEQUENCE: 25 aagcgggccc tgctcgatgc cctgttkatc gagatgctgg acaggc 46

<210> SEQ ID NO 26
<211> LENGTH: 747
<212> TYPE: DNA
<213> ORGANISM: Human immunodeficiency virus
<220> FEATURE:
<221> NAME/KEY: CDS
<222> LOCATION: (1)..(747)

<400> SEQUENCE: 26 atg tct aga ctg gac aag agc aaa gtc ata aac tct gct ctg gaa tta 48
Met Ser Arg Leu Asp Lys Ser Lys Val Ile Asn Ser Ala Leu Glu Leu
1 5 10 15 ctc aat gga gtc ggt atc gaa ggc ctg acg aca agg aaa ctc gct caa 96
Leu Asn Gly Val Gly Ile Glu Gly Leu Thr Thr Arg Lys Leu Ala Gln
20 25 30 aag ctg gga gtt gag cag cct acc ctg tac tgg cac gtg aag aac aag 144
Lys Leu Gly Val Glu Gln Pro Thr Leu Tyr Trp His Val Lys Asn Lys
35 40 45 cgg gcc ctg ctc gat gcc ctg cca atc gag atg ctg gac agg cat cat 192
Arg Ala Leu Leu Asp Ala Leu Pro Ile Glu Met Leu Asp Arg His His
50 55 60 acc cac ttc tgc ccc ctg gaa ggc gag tca tgg caa gac ttt ctg cgg 240
Thr His Phe Cys Pro Leu Glu Gly Glu Ser Trp Gln Asp Phe Leu Arg
65 70 75 80

```
aac aac gcc aag tca ttc cgc tgt gct ctc ctc tca cat cgc gac ggg      288
Asn Asn Ala Lys Ser Phe Arg Cys Ala Leu Leu Ser His Arg Asp Gly
                85                  90                  95

gct aaa gtg cat ctc ggc acc cgc cca aca gag aaa cag tac gaa acc      336
Ala Lys Val His Leu Gly Thr Arg Pro Thr Glu Lys Gln Tyr Glu Thr
            100                 105                 110

ctg gaa aat cag ctc gcg ttc ctg tgt cag caa ggc ttc tcc ctg gag      384
Leu Glu Asn Gln Leu Ala Phe Leu Cys Gln Gln Gly Phe Ser Leu Glu
        115                 120                 125

aac gca ctg tac gct ctg tcc gcc gtg ggc cac ttt aca ctg ggc tgc      432
Asn Ala Leu Tyr Ala Leu Ser Ala Val Gly His Phe Thr Leu Gly Cys
    130                 135                 140

gta ttg gag gaa cag gag cat caa gta gca aaa gag gaa aga gag aca      480
Val Leu Glu Glu Gln Glu His Gln Val Ala Lys Glu Glu Arg Glu Thr
145                 150                 155                 160

cct acc acc gat tct atg ccc cca ctt ctg aga caa gca att gag ctg      528
Pro Thr Thr Asp Ser Met Pro Pro Leu Leu Arg Gln Ala Ile Glu Leu
                165                 170                 175

ttc gac cgg cag gga gcc gaa cct gcc ttc ctt ttc ggc ctg gaa cta      576
Phe Asp Arg Gln Gly Ala Glu Pro Ala Phe Leu Phe Gly Leu Glu Leu
            180                 185                 190

atc ata tgt ggc ctg gag aaa cag cta aag tgc gaa agc ggc ggg ccg      624
Ile Ile Cys Gly Leu Glu Lys Gln Leu Lys Cys Glu Ser Gly Gly Pro
        195                 200                 205

gcc gac gcc ctt gac gat ttt gac tta gac atg ctc cca gcc gat gcc      672
Ala Asp Ala Leu Asp Asp Phe Asp Leu Asp Met Leu Pro Ala Asp Ala
    210                 215                 220

ctt gac gac ttt gac ctt gat atg ctg cct gct gac gct ctt gac gat      720
Leu Asp Asp Phe Asp Leu Asp Met Leu Pro Ala Asp Ala Leu Asp Asp
225                 230                 235                 240

ttt gac ctt gac atg ctc ccc ggg taa                                  747
Phe Asp Leu Asp Met Leu Pro Gly
                245


<210> SEQ ID NO 27
<211> LENGTH: 248
<212> TYPE: PRT
<213> ORGANISM: Artificial sequence
<220> FEATURE:
<223> OTHER INFORMATION: Fusion protein

<400> SEQUENCE: 27

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
```

```
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Ala Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245


<210> SEQ ID NO 28
<211> LENGTH: 747
<212> TYPE: DNA
<213> ORGANISM: Artificial sequence
<220> FEATURE:
<223> OTHER INFORMATION: Hybrid gene

<400> SEQUENCE: 28

atgtctagac tggacaagag caaagtcata aactctgctc tggaattact caatggagtc     60

ggtatcgaag gcctgacgac aaggaaactc gctcaaaagc tgggagttga gcagcctacc    120

ctgtactggc acgtgaagaa caagcgggcc ctgctcgatg ccctgccaat cgagatgctg    180

gacaggcatc atacccactc ctgccccctg gaaggcgagt catggcaaga ctttctgcgg    240

aacaacgcca agtcataccg ctgtgctctc ctctcacatc gcgacggggc taaagtgcat    300

ctcggcaccc gcccaacaga gaaacagtac gaaaccctgg aaaatcagct cgcgttcctg    360

tgtcagcaag gcttctccct ggagaacgca ctgtacgctc tgtccgccgt gggccacttt    420

acactgggct gcgtattgga ggaacaggag catcaagtag caaaagagga aagagagaca    480

cctaccaccg attctatgcc cccacttctg aaacaagcaa ttgagctgtt cgaccggcag    540

ggagccgaac ctgccttcct tttcggcctg gaactaatca tatgtggcct ggagaaacag    600

ctaaagtgcg aaagcggcgg gccgaccgac gcccttgacg attttgactt agacatgctc    660

ccagccgatg cccttgacga ctttgacctt gatatgctgc ctgctgacgc tcttgacgat    720

tttgaccttg acatgctccc cgggtaa                                        747


<210> SEQ ID NO 29
<211> LENGTH: 248
<212> TYPE: PRT
<213> ORGANISM: Artificial sequence
<220> FEATURE:
<223> OTHER INFORMATION: Fusion protein

<400> SEQUENCE: 29

Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
```

-continued

```
    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245
```

The invention claimed is:

1. A method for inducibly expressing a nucleic acid sequence of interest, the method comprising:

providing a nucleic acid construct comprising said nucleic acid sequence of interest operably linked to an inducible gene expression system that comprises a reverse tetracycline-controlled transactivator (rtTA) encoding nucleic acid sequence and/or a single chain rtTA encoding nucleic acid sequence, said rtTA encoding nucleic acid sequence and/or single chain rtTA encoding nucleic acid sequence comprising a mutation in a codon at rtTA amino acid position 9, and/or 19, and/or 37, and/or 56, and/or 67, and/or 68, and/or 138, and/or 157, and/or 171, and/or 177, and/or 195;

introducing said nucleic acid construct to a suitable expression system; and allowing for inducible expression of said nucleic acid sequence of interest.

2. The method according to claim 1, wherein said rtTA encoding nucleic acid sequence and/or single chain rtTA encoding nucleic acid sequence further comprise a mutation in a codon at rtTA amino acid position 12, and/or 86, and/or 209.

3. The method according to claim 1, wherein said rtTA encoding nucleic acid sequence and/or single chain rtTA encoding nucleic acid sequence comprises a codon at rtTA amino acid position 19 that differs in at least two nucleotides from a glutamate codon, and/or a codon at rtTA position 37 that differs in at least two nucleotides from an alanine, a lysine or a serine codon, and/or a glutamine or lysine codon at rtTA amino acid position 56.

4. The method according to claim 1, wherein said rtTA encoding nucleic acid sequence and/or single chain rtTA encoding nucleic acid sequence comprise a glycine codon at rtTA amino acid position 19 that differs in at least two nucleotides from a glutamate codon.

5. The method according to claim 1, wherein said rtTA encoding nucleic acid sequence and/or single chain rtTA encoding nucleic acid sequence comprise an alanine, cysteine, phenylalanine, histidine, isoleucine, leucine, methionine, asparagine, arginine, serine, threonine, valine, tryptophan or tyrosine codon at rtTA amino acid position 19 that differs in at least two nucleotides from a glutamate codon.

6. The method according to claim 1, wherein said rtTA encoding nucleic acid sequence and/or single chain rtTA encoding nucleic acid sequence comprise a histidine, a leucine or an arginine codon at rtTA amino acid position 37 that differs in at least two nucleotides from an alanine, a lysine or a serine codon.

7. The method according to claim 1, wherein said rtTA encoding nucleic acid sequence and/or single chain rtTA encoding nucleic acid sequence comprises a codon at rtTA amino acid position 9 encoding isoleucine, and/or a codon at rtTA amino acid position 19 encoding alanine, cysteine, aspartate, phenylalanine, histidine, isoleucine, lysine, leucine, methionine, asparagine, glutamine, arginine, serine, threonine, valine, tryptophan or tyrosine, and/or a codon at rtTA amino acid position 37 encoding cysteine, methionine, glutamine, threonine, histidine, leucine or arginine, and/or a codon at rtTA amino acid position 56 encoding lysine or glutamine, and/or a codon at rtTA amino acid position 67 encoding serine, and/or a codon at rtTA amino acid position 68 encoding arginine, and/or a codon at rtTA amino acid position 86 encoding tyrosine, and/or a codon at rtTA amino acid position 138 encoding aspartate or serine, and/or a codon at rtTA amino acid position 157 encoding lysine, and/or a codon at rtTA amino acid position 171 encoding lysine, and/or a codon at rtTA amino acid position 177 encoding leucine, and/or a codon at rtTA amino acid position 195 encoding serine, and/or a codon at rtTA amino acid position 209 encoding threonine.

8. The method according to claim 1, wherein said rtTA encoding nucleic acid sequence and/or single chain rtTA encoding nucleic acid sequence comprise at least one mutation as depicted in FIG. 14B or FIG. 14C.

9. The method according to claim 1, wherein said rtTA encoding nucleic acid sequence and/or single chain rtTA encoding nucleic acid sequence comprise at least one codon mutation as compared to a rtTA encoding nucleic acid sequence depicted in FIG. 19.

10. The method according to claim 1, wherein said nucleic acid of interest is expressed in a higher eukaryotic expression system.

11. The method according to claim 10, wherein said nucleic acid of interest is expressed in a mammalian cell.

12. The method according to claim 1, wherein said nucleic acid of interest comprises a viral sequence essential for replication.

13. The method according to claim 1, wherein said nucleic acid of interest comprises at least part of an HIV genome essential for replication.

14. A synthetic or recombinant nucleic acid sequence comprising a rtTA encoding nucleic acid sequence and/or a single chain rtTA encoding nucleic acid sequence, which rtTA encoding nucleic acid sequence and/or single chain rtTA encoding nucleic acid sequence comprises a mutated codon at rtTA amino acid position 9, and/or 19, and/or 37, and/or 56, and/or 67, and/or 68, and/or 138, and/or 157, and/or 171, and/or 177, and/or 195.

15. The synthetic or recombinant nucleic acid sequence according to claim 14, wherein said rtTA encoding nucleic acid sequence and/or single chain rtTA encoding nucleic acid sequence further comprises a mutation in a codon at rtTA amino acid position 12, and/or 86, and/or 209.

16. The synthetic or recombinant nucleic acid sequence according to claim 14, wherein said rtTA encoding nucleic acid sequence and/or single chain rtTA encoding nucleic acid sequence comprises a codon at rtTA amino acid position 19 that differs in at least two nucleotides from a glutamate codon and/or a codon at rtTA position 37 that differs in at least two nucleotides from an alanine, a lysine or a serine codon, and/or a glutamine or lysine codon at rtTA amino acid position 56.

17. The synthetic or recombinant nucleic acid sequence according to claim 14, wherein said rtTA encoding nucleic acid sequence and/or single chain rtTA encoding nucleic acid sequence comprises a glycine codon at rtTA amino acid position 19 that differs in at least two nucleotides from a glutamate codon.

18. The synthetic or recombinant nucleic acid sequence according to claim 14, wherein said rtTA encoding nucleic acid sequence and/or single chain rtTA encoding nucleic acid sequence comprises an alanine, cysteine, phenylalanine, histidine, isoleucine, leucine, methionine, asparagine, arginine, serine, threonine, valine, tryptophan or tyrosine codon at rtTA amino acid position 19 that differs in at least two nucleotides from a glutamate codon.

19. The synthetic or recombinant nucleic acid sequence according to claim 14, wherein said rtTA encoding nucleic acid sequence and/or single chain rtTA encoding nucleic acid sequence comprises a histidine, a leucine or an arginine codon at rtTA amino acid position 37 that differs in at least two nucleotides from an alanine, a lysine or a serine codon.

20. The synthetic or recombinant nucleic acid sequence according to claim 14, wherein said rtTA encoding nucleic acid sequence and/or single chain rtTA encoding nucleic acid sequence comprises a codon at rtTA amino acid position 9 encoding isoleucine, and/or a codon at rtTA amino acid position 19 encoding alanine, cysteine, aspartate, phenylalanine, histidine, isoleucine, lysine, leucine, methionine, asparagine, glutamine, arginine, serine, threonine, valine, tryptophan or tyrosine, and/or a codon at rtTA amino acid position 37 encoding cysteine, methionine, glutamine, threonine, histidine, leucine or arginine, and/or a codon at rtTA amino acid position 56 encoding lysine or glutamine, and/or a codon at rtTA amino acid position 67 encoding serine, and/or a codon at rtTA amino acid position 68 encoding arginine, and/or a codon at rtTA amino acid position 86 encoding tyrosine, and/or a codon at rtTA amino acid position 138 encoding aspartate or serine, and/or a codon at rtTA amino acid position 157 encoding lysine, and/or a codon at rtTA amino acid position 171 encoding lysine, and/or a codon at rtTA amino acid position 177 encoding leucine, and/or a codon at rtTA amino acid position 195 encoding serine, and/or a codon at rtTA amino acid position 209 encoding threonine.

21. The synthetic or recombinant nucleic acid sequence according to claim 14, wherein said rtTA encoding nucleic acid sequence and/or single chain rtTA encoding nucleic acid sequence comprises at least one mutation as depicted in FIG. 14B or FIG. 14C.

22. The synthetic or recombinant nucleic acid sequence according to claim 14, wherein said rtTA encoding nucleic acid sequence and/or single chain rtTA encoding nucleic acid sequence comprises at least one mutation as compared to an rtTA encoding nucleic acid sequence depicted in FIG. 19.

23. A synthetic or recombinant amino acid sequence encoded by the nucleic acid sequence according to claim 14.

24. A synthetic or recombinant amino acid sequence comprising a rtTA sequence and/or a single chain rtTA sequence, which rtTA sequence and/or single chain rtTA sequence comprises an isoleucine at position 9, and/or an alanine, cysteine, aspartate, phenylalanine, histidine, isoleucine, lysine, leucine, methionine, asparagine, glutamine, arginine, serine, threonine, valine, tryptophan or tyrosine at position 19, and/or a cysteine, methionine, glutamine, threonine, histidine, leucine or arginine at position 37, and/or a lysine or glutamine at position 56, and/or a serine at position 67, and/or an arginine at position 68, and/or a tyrosine at position 86, and/or an aspartate or serine at position 138, and/or a lysine at position 157, and/or a lysine at position 171, and/or a leucine at position 177, and/or a serine at position 195, and/or a threonine at position 209.

25. In a method of inducing expression of a nucleic acid sequence of interest, the improvement comprising:

utilizing the synthetic or recombinant nucleic acid sequence of claim 14 for inducible expression of a nucleic acid sequence of interest.

26. In a method of inducing expression of a nucleic acid sequence of interest, the improvement comprising:

utilizing the amino acid sequence encoded by any one of the nucleic acid sequences of claim 24 for inducible expression of a nucleic acid sequence of interest.

27. In a method of tetracycline-inducible and/or minocycline-inducible expression of a nucleic acid sequence of interest, the improvement comprising:

utilizing the recombinant nucleic acid sequence comprising an rtTA encoding nucleic acid sequence and/or a single chain rtTA encoding nucleic acid sequence, which rtTA encoding nucleic acid sequence and/or single chain rtTA encoding nucleic acid sequence comprises a mutation or a combination of mutations as depicted in FIG. 15, except for the wild type rtTA and the F86Y A209T variant, for tetracycline-inducible and/or minocycline-inducible expression of a nucleic acid of interest.

28. A vector comprising the nucleic acid sequence of claim 14.

29. An inducible viral replicon, comprising:

the nucleic acid sequence of claim 14, and at least one viral sequence that is essential for replication under direct or indirect control of said nucleic acid sequence.

30. The inducible viral replicon according to claim 29, comprising all viral sequences essential for replication under direct or indirect control of said nucleic acid sequence.

31. The inducible viral replicon according to claim 29, which is derived from a human immunodeficiency virus.

32. The inducible viral replicon of claim 29, wherein the nucleic acid sequence is inserted into the nef gene.

33. The inducible viral replicon of claim 29, further comprising at least one tetO motif in at least one functional LTR.

34. The inducible viral replicon of claim 33, further comprising at least 2, 4, 6, or 8 such elements in at least one functional LTR.

35. The inducible viral replicon of claim 29, wherein at least one LTR is modified to avoid reversion to wild type virus.

36. A method for producing a virus dependent upon an inducing agent for replication, the method comprising:

providing a permissive cell with the inducible viral replicon of claim 29, culturing said cell in the presence of said inducing agent, and harvesting said dependent virus from said culture.

37. The method according to claim 36, in which said dependent virus is a human immunodeficiency virus.

38. The method according to claim 36, in which said virus is an attenuated virus.

39. A virus dependent on an inducing agent for replication obtainable by the method according to claim 36.

40. The virus according to claim 39, which is a human immunodeficiency virus.

41. A method for the controlled replication of a virus or a viral replicon, the method comprising:

providing a permissive cell with the inducible viral replicon of claim 29;

culturing said cell in the presence of said inducing agent; and manipulating the amount of inducing agent present.

42. An isolated cell comprising the nucleic acid sequence of claim 14.

*43. A method for inducibly expressing a nucleic acid sequence of interest, the method comprising the steps of:*

*providing a nucleic acid construct comprising said nucleic acid sequence of interest operably linked to an inducible gene expression system that comprises a reverse tetracycline-controlled transactivator (rtTA) encoding nucleic acid sequence and/or a single chain rtTA encoding nucleic acid sequence, said rtTA encoding nucleic acid sequence and/or single chain rtTA encoding nucleic acid sequence comprising a mutation in a codon at rtTA amino acid position 67, optionally with one or more additional mutations in a codon at rtTA amino acid position 9, 12, 19, 37, 56, 68, 86, 138, 157, 171, 177, 195 or 209;*

*introducing said nucleic acid construct to a suitable expression system; and*

*allowing for inducible expression of said nucleic acid sequence of interest.*

*44. The method according to claim 43, wherein said rtTA encoding nucleic acid sequence and/or single chain rtTA encoding nucleic acid sequence comprises a codon at rtTA amino acid position 19 that differs in at least two nucleotides from a glutamate codon, and/or a codon at rtTA position 37 that differs in at least two nucleotides from an alanine, a lysine or a serine codon, and/or a glutamine or lysine codon at rtTA amino acid position 56.*

*45. The method according to claim 43, wherein said rtTA encoding nucleic acid sequence and/or single chain rtTA encoding nucleic acid sequence comprises a glycine codon at rtTA amino acid position 19 that differs in at least two nucleotides from a glutamate codon.*

*46. The method according to claim 43, wherein said rtTA encoding nucleic acid sequence and/or single chain rtTA encoding nucleic acid sequence comprises an alanine, cysteine, phenylalanine, histidine, isoleucine, leucine, methionine, asparagine, arginine, serine, threonine, valine, tryptophan or tyrosine codon at rtTA amino acid position 19 that differs in at least two nucleotides from a glutamate codon.*

*47. The method according to claim 43, wherein said rtTA encoding nucleic acid sequence and/or single chain rtTA encoding nucleic acid sequence comprises a histidine, a leucine or an arginine codon at rtTA amino acid position 37 that differs in at least two nucleotides from an alanine, a lysine or a serine codon.*

*48. The method according to claim 43, wherein said rtTA encoding nucleic acid sequence and/or single chain rtTA encoding nucleic acid sequence comprises a codon at rtTA amino acid position 9 encoding isoleucine, and/or a codon at rtTA amino acid position 19 encoding alanine, cysteine, aspartate, phenylalanine, histidine, isoleucine, lysine, leucine, methionine, asparagine, glutamine, arginine, serine, threonine, valine, tryptophan or tyrosine, and/or a codon at rtTA amino acid position 37 encoding cysteine, methionine, glutamine, threonine, histidine, leucine or arginine, and/or a codon at rtTA amino acid position 56 encoding lysine or glutamine, and/or a codon at rtTA amino acid position 67 encoding serine, and/or a codon at rtTA amino acid position 68 encoding arginine, and/or a codon at rtTA amino acid position 86 encoding tyrosine, and/or a codon at rtTA amino acid position 138 encoding aspartate or serine, and/or a codon at rtTA amino acid position 157 encoding lysine, and/or a codon at rtTA amino acid position 171 encoding lysine, and/or a codon at rtTA amino acid position 177 encoding leucine, and/or a codon at rtTA amino acid position 195 encoding serine, and/or a codon at rtTA amino acid position 209 encoding threonine.*

*49. The method according to claim 43, wherein said rtTA encoding nucleic acid sequence and/or single chain rtTA encoding nucleic acid sequence comprises at least one mutation as depicted in FIG. 14B or FIG. 14C.*

*50. The method according to claim 43, wherein said rtTA encoding nucleic acid sequence and/or single chain rtTA encoding nucleic acid sequence comprises at least one codon mutation as compared to a rtTA encoding nucleic acid sequence depicted in FIG. 19.*

*51. The method according to claim 43, wherein said nucleic acid of interest is expressed in a higher eukaryotic expression system.*

52. The method according to claim 51, wherein said nucleic acid of interest is expressed in a mammalian cell.

53. The method according to claim 43, wherein said nucleic acid of interest comprises a viral sequence essential for replication.

54. The method according to claim 43, wherein said nucleic acid of interest comprises at least part of an HIV genome essential for replication.

55. A synthetic or recombinant nucleic acid sequence comprising a rtTA encoding nucleic acid sequence and/or a single chain rtTA encoding nucleic acid sequence, which rtTA encoding nucleic acid sequence and/or single chain rtTA encoding nucleic acid sequence comprises a mutated codon at rtTA amino acid position 67, optionally with one or more additional mutations in a codon at rtTA amino acid position 9, 12, 19, 37, 56, 68, 86, 138, 157, 171, 177, 195 or 209.

56. The synthetic or recombinant nucleic acid sequence according to claim 55, wherein said rtTA encoding nucleic acid sequence and/or single chain rtTA encoding nucleic acid sequence comprises a codon at rtTA amino acid position 19 that differs in at least two nucleotides from a glutamate codon and/or a codon at rtTA position 37 that differs in at least two nucleotides from an alanine, a lysine or a serine codon, and/or a glutamine or lysine codon at rtTA amino acid position 56.

57. The synthetic or recombinant nucleic acid sequence according to claim 55, wherein said rtTA encoding nucleic acid sequence and/or single chain rtTA encoding nucleic acid sequence comprises a glycine codon at rtTA amino acid position 19 that differs in at least two nucleotides from a glutamate codon.

58. The synthetic or recombinant nucleic acid sequence according to claim 55, wherein said rtTA encoding nucleic acid sequence and/or single chain rtTA encoding nucleic acid sequence comprises an alanine, cysteine, phenylalanine, histidine, isoleucine, leucine, methionine, asparagine, arginine, serine, threonine, valine, tryptophan or tyrosine codon at rtTA amino acid position 19 that differs in at least two nucleotides from a glutamate codon.

59. The synthetic or recombinant nucleic acid sequence according to claim 55, wherein said rtTA encoding nucleic acid sequence and/or single chain rtTA encoding nucleic acid sequence comprises a histidine, a leucine or an arginine codon at rtTA amino acid position 37 that differs in at least two nucleotides from an alanine, a lysine or a serine codon.

60. The synthetic or recombinant nucleic acid sequence according to claim 55, wherein said rtTA encoding nucleic acid sequence and/or single chain rtTA encoding nucleic acid sequence comprises a codon at rtTA amino acid position 9 encoding isoleucine, and/or a codon at rtTA amino acid position 19 encoding alanine, cysteine, aspartate, phenylalanine, histidine, isoleucine, lysine, leucine, methionine, asparagine, glutamine, arginine, serine, threonine, valine, tryptophan or tyrosine, and/or a codon at rtTA amino acid position 37 encoding cysteine, methionine, glutamine, threonine, histidine, leucine or arginine, and/or a codon at rtTA amino acid position 56 encoding lysine or glutamine, and/or a codon at rtTA amino acid position 67 encoding serine, and/or a codon at rtTA amino acid position 68 encoding arginine, and/or a codon at rtTA amino acid position 86 encoding tyrosine, and/or a codon at rtTA amino acid position 138 encoding aspartate or serine, and/or a codon at rtTA amino acid position 157 encoding lysine, and/or a codon at rtTA amino acid position 171 encoding lysine, and/or a codon at rtTA amino acid position 177 encoding leucine, and/or a codon at rtTA amino acid position 195 encoding serine, and/or a codon at rtTA amino acid position 209 encoding threonine.

61. The synthetic or recombinant nucleic acid sequence according to claim 55, wherein said rtTA encoding nucleic acid sequence and/or single chain rtTA encoding nucleic acid sequence comprises at least one mutation as depicted in FIG. 14B or FIG. 14C.

62. The synthetic or recombinant nucleic acid sequence according to claim 55, wherein said rtTA encoding nucleic acid sequence and/or single chain rtTA encoding nucleic acid sequence comprises at least one mutation as compared to an rtTA encoding nucleic acid sequence depicted in FIG. 19.

63. A synthetic or recombinant amino acid sequence encoded by the nucleic acid sequence according to claim 55.

64. In a method of inducing expression of a nucleic acid sequence of interest, the improvement comprising: utilizing the synthetic or recombinant nucleic acid sequence of claim 55 for inducible expression of a nucleic acid sequence of interest.

65. A vector comprising the nucleic acid sequence of claim 55.

66. An inducible viral replicon, comprising: the nucleic acid sequence of claim 55, and at least one viral sequence that is essential for replication under direct or indirect control of said nucleic acid sequence.

67. The inducible viral replicon according to claim 66, comprising all viral sequences essential for replication under direct or indirect control of said nucleic acid sequence.

68. The inducible viral replicon according to claim 66, which is derived from a human immunodeficiency virus.

69. The inducible viral replicon of claim 66, wherein the nucleic acid sequence is inserted into the nef gene.

70. The inducible viral replicon of claim 66, further comprising at least one tetO motif in at least one functional LTR.

71. The inducible viral replicon of claim 70, further comprising at least 2, 4, 6, or 8 such elements in at least one functional LTR.

72. The inducible viral replicon of claim 66, wherein at least one LTR is modified to avoid reversion to wild type virus.

73. A method for producing a virus dependent upon an inducing agent for replication, the method comprising: providing a permissive cell with the inducible viral replicon of claim 66, culturing said cell in the presence of said inducing agent, and harvesting said dependent virus from said culture.

74. The method according to claim 73, in which said dependent virus is a human immunodeficiency virus.

75. The method according to claim 73, in which said virus is an attenuated virus.

76. A virus dependent on an inducing agent for replication obtainable by the method according to claim 73.

77. The virus according to claim 76, which is a human immunodeficiency virus.

78. A method for the controlled replication of a virus or a viral replicon, the method comprising: providing a permissive cell with the inducible viral replicon of claim 66; culturing said cell in the presence of said inducing agent and manipulating the amount of inducing agent present.

79. An isolated cell comprising the nucleic acid sequence of claim 55.

*80. A transactivator, having the DNA sequence (5'- 3' orientation):*

(*SEQ ID NO: 28*)

```
atgtctagactggacaagagcaaagtcataaactctgctctggaattact
caatggagtcggtatcgaaggcctgacgacaaggaaactcgctcaaaagc
tgggagttgagcagcctaccctgtactggcacgtgaagaacaagcgggcc
ctgctcgatgccctgccaatcgagatgctggacaggcatcatacccactc
ctgccccctggaaggcgagtcatggcaagactttctgcggaacaacgcca
agtcataccgctgtgctctcctctcacatcgcgacggggctaaagtgcat
ctcggcacccgcccaacagagaaacagtacgaaaccctggaaaatcagct
cgcgttcctgtgtcagcaaggcttctccctggagaacgcactgtacgctc
tgtccgccgtgggccactttacactgggctgcgtattggaggaacaggag
catcaagtagcaaaagaggaaagagagacacctaccaccgattctatgcc
cccacttctgaaacaagcaattgagctgttcgaccggcagggagccgaac
ctgccttccttttcggcctggaactaatcatatgtggcctggagaaacag
ctaaagtgcgaaagcggcgggccgaccgacgeccttgacgattttgactt
agacatgctcccagccgatgcccttgacgactttgaccttgatatgctgc
ctgctgacgctcttgacgattttgaccttgacatgctccccgggtaa.
```

*81. A transactivator, having the amino acid sequence: MSRLDKSKVINSALELLNGVGIEGLTTRKLAQKL-GVEQPTLYWHVKNKRALLDALPIEML DRHHTH-SCPLEGESWQDFLRNNAKSYRCALLSHRDGAKVH-LGTRPTEKQYETLENQLAFL CQQGFSLENALYAL-SAVGHFTLGCVLEEQEHQVAKEERETPTTDSMP-PLLKQAIELFDRQ GAEPAFLFGLELIICGLEKQL-KCESGGPTDALDDFDLDMLPADALDDFDLDML-PADALDDFDLDMLPG*(SEQ ID NO: 29).*

*82. A method for inducibly expressing a nucleic acid sequence of interest, the method comprising the steps of:*

*providing a nucleic acid construct comprising said nucleic acid sequence of interest operably linked to an inducible gene expression system that comprises a reverse tetracycline-controlled transactivator (rtTA) encoding nucleic acid sequence and/or a single chain rtTA encoding nucleic acid sequence, said rtTA encoding nucleic acid sequence and/or single chain rtTA encoding nucleic acid sequence comprising a mutation in a codon at rtTA amino acid position 67;*

*introducing said nucleic acid construct to a suitable expression system; and*

*allowing for inducible expression of said nucleic acid sequence of interest.*

*83. A synthetic or recombinant nucleic acid sequence comprising a rtTA encoding nucleic acid sequence and/or a single chain rtTA encoding nucleic acid sequence, which rtTA encoding nucleic acid sequence and/or single chain rtTA encoding nucleic acid sequence comprises a mutated codon at rtTA amino acid position 67.*

* * * * *